(12) United States Patent
McMurray et al.

(10) Patent No.: US 12,251,497 B2
(45) Date of Patent: Mar. 18, 2025

(54) INDICATOR MARKING TECHNOLOGY FOR TEXTILES

(71) Applicant: Atex Technologies, Inc., Pinebluff, NC (US)

(72) Inventors: Brian McMurray, Aberdeen, NC (US); Mark Wesley Jessup, Whispering Pines, NC (US); Tim Warner, Whispering Pines, NC (US); Gary Webb Broussard, Jr., Carthage, NC (US); David B. Carroll, Pinehurst, NC (US); Morgan Gwaltney, Pinehurst, NC (US)

(73) Assignee: ATEX Technologies, Inc., Pinebluff, NC (US)

( * ) Notice: Subject to any disclaimer, the term of this patent is extended or adjusted under 35 U.S.C. 154(b) by 701 days.

(21) Appl. No.: 17/471,835

(22) Filed: Sep. 10, 2021

(65) Prior Publication Data

US 2022/0056634 A1 Feb. 24, 2022

Related U.S. Application Data

(63) Continuation of application No. PCT/US2020/022796, filed on Mar. 13, 2020.

(Continued)

(51) Int. Cl.
 *A61L 27/50* (2006.01)
 *D03D 3/02* (2006.01)
(Continued)

(52) U.S. Cl.
 CPC ............. *A61L 27/507* (2013.01); *D03D 3/02* (2013.01); *D03D 15/283* (2021.01); *D03D 15/41* (2021.01);
(Continued)

(58) Field of Classification Search
 CPC .... A61L 27/507; D03D 15/283; D03D 15/41; D03D 3/02; D10B 2321/0211; D10B 2331/04; D10B 2509/00; D06Q 1/00; D06M 10/001; D06M 10/005; D04C 1/02; D04B 21/16; D04B 1/16
See application file for complete search history.

(56) References Cited

U.S. PATENT DOCUMENTS

| | | |
|---|---|---|
| 3,805,301 A | 4/1974 | Liebig |
| 6,994,724 B2 | 2/2006 | Schmitt |

(Continued)

FOREIGN PATENT DOCUMENTS

| | | |
|---|---|---|
| EP | 1682356 B1 | 7/2006 |
| WO | 20080109019 A1 | 9/2008 |

OTHER PUBLICATIONS

European Patent Office, Supplementary European (EP) Search Report For EP Appl. No. 20769993.5, dated May 23, 2022, pp. 1-12, Munich, DE.

(Continued)

*Primary Examiner* — Catherine A. Simone
(74) *Attorney, Agent, or Firm* — BrainSpark Associates, LLC

(57) ABSTRACT

Improved methods, designs and/or systems for incorporating markings and/or other visual and/or tactilely identifiable indicia on woven, knitted, nonwoven, braided and/or felted textiles used for medical textile implants and prostheses, including medical graft prostheses that would not affect the overall mechanical performance of the textile.

19 Claims, 43 Drawing Sheets

Related U.S. Application Data

(60) Provisional application No. 62/818,099, filed on Mar. 13, 2019.

(51) Int. Cl.
| | | |
|---|---|---|
| *D03D 15/283* | (2021.01) | |
| *D03D 15/41* | (2021.01) | |
| *D04B 1/16* | (2006.01) | |
| *D04B 21/16* | (2006.01) | |
| *D04C 1/02* | (2006.01) | |
| *D06M 10/00* | (2006.01) | |
| *D06M 101/18* | (2006.01) | |
| *D06M 101/32* | (2006.01) | |
| *D06Q 1/00* | (2006.01) | |

(52) U.S. Cl.
CPC ............... *D04B 1/16* (2013.01); *D04B 21/16* (2013.01); *D04C 1/02* (2013.01); *D06M 10/001* (2013.01); *D06M 10/005* (2013.01); *D06Q 1/00* (2013.01); *D06M 2101/18* (2013.01); *D06M 2101/32* (2013.01); *D10B 2321/0211* (2013.01); *D10B 2331/04* (2013.01); *D10B 2509/00* (2013.01)

(56) References Cited

U.S. PATENT DOCUMENTS

| | | |
|---|---|---|
| 7,921,678 B2 | 4/2011 | Norris et al. |
| 8,961,560 B2 | 2/2015 | Avelar et al. |
| 9,862,219 B2 | 1/2018 | Klein |
| RE46,779 E | 4/2018 | Norris et al. |
| 10,364,518 B2 | 7/2019 | Van Hulle et al. |
| 2005/0240261 A1 | 10/2005 | Rakos et al. |
| 2013/0158571 A1 | 6/2013 | Meneghin et al. |
| 2014/0364878 A1 | 12/2014 | Ladet et al. |
| 2016/0106530 A1 | 4/2016 | Schneidereit et al. |
| 2016/0166437 A1 | 6/2016 | Lundh et al. |
| 2018/0243067 A1 | 8/2018 | Ladet et al. |
| 2018/0303596 A1 | 10/2018 | Du |

OTHER PUBLICATIONS

United States International Search Authority, International Search Report and Written Opinion, Jul. 28, 2020, pp. 1-13.

| Option # | Option Name | Option Description |
|---|---|---|
| 1 | UV Laser Marking | UV Laser, Cold Marking |
| 2 | Embossing | Add raised features to textile using mandrels |
| 3 | Stamping / crimping | Add recessed features to textile using mandrels |
| 4 | Ultrasonic Marking | Design custom welder and sonotrode |
| 5 | Printing | Medical Grade VI Ink |
| 6 | Weaving / Braiding / Knitting | Weave, braid or knit parts and add stripes |

|   | A | B | C | D | E | F | G |
|---|---|---|---|---|---|---|---|
| 1 |   |   |   |   |   |   |   |
| 2 | X |   |   |   |   |   |   |
| 3 | X | X | X | X |   |   |   |
| 4 | X | X | X | X |   |   |   |
| 5 |   | X | X | X |   |   |   |
| 6 |   |   | X | X | X |   |   |
| 7 |   |   |   | X | X | X | X |
| 8 |   |   |   | X | X | X | X |

FIG. 5B

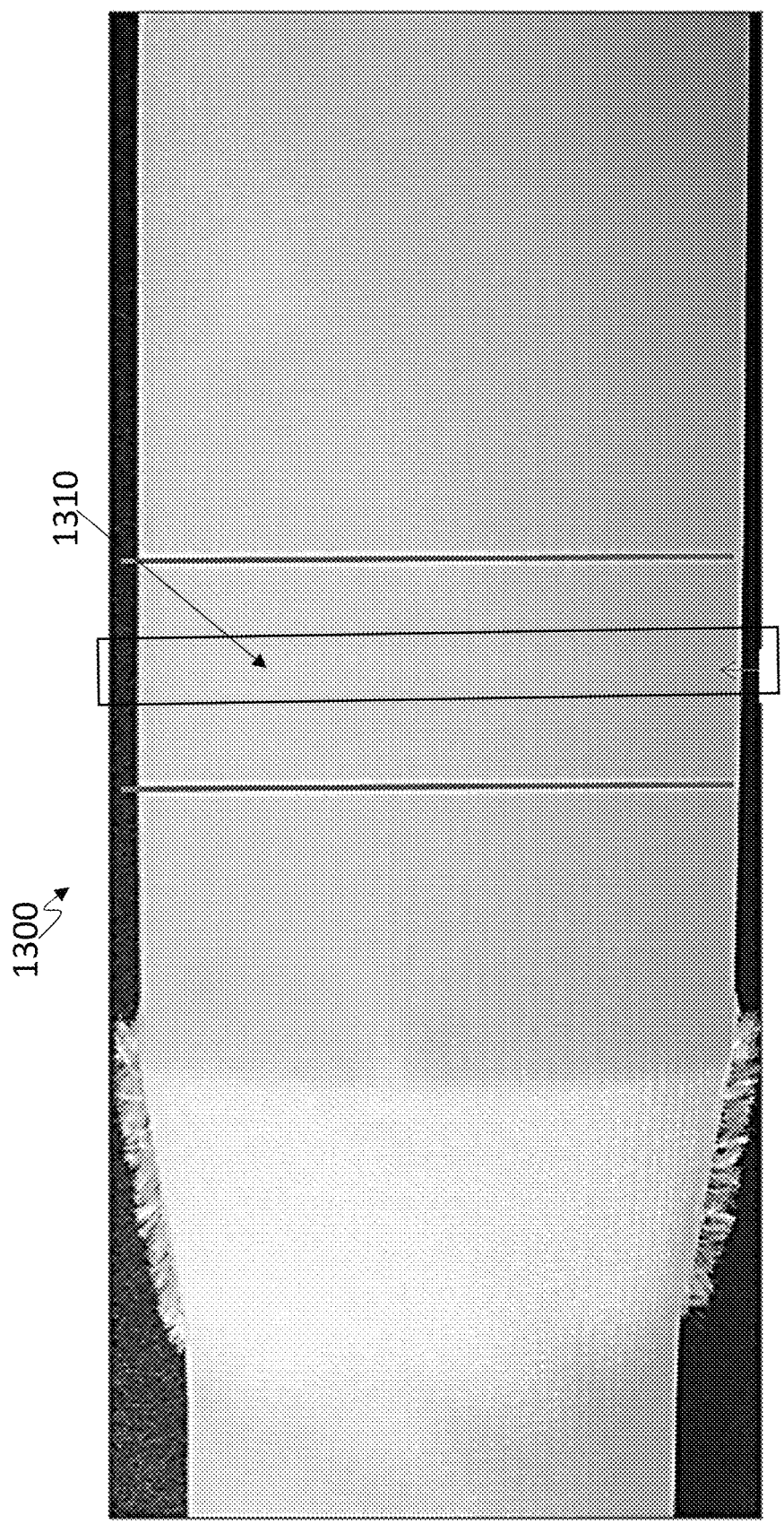

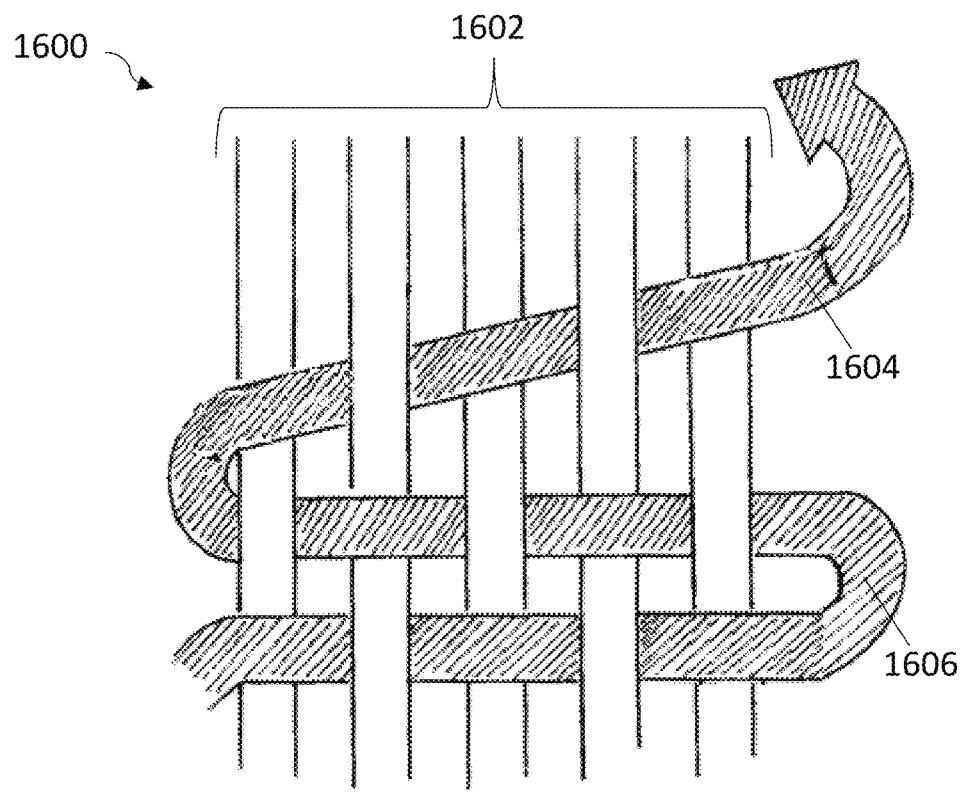
FIG. 16
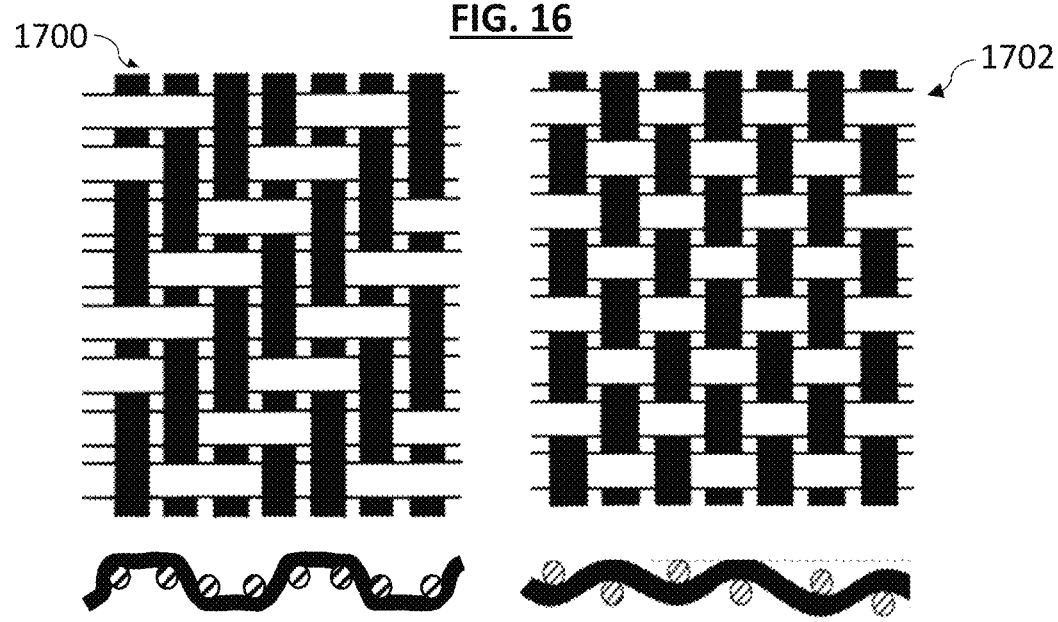
FIG. 17A  FIG. 17B

1900 ↘
@, !
FIG. 19A
1902 ↘
1, 2, 3...
FIG. 19B
1904 ↘
A, B, C...
FIG. 19C
1906 ↘
A1B2C3...
FIG. 19D
1908 ↘
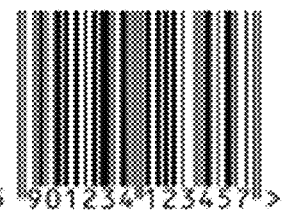
FIG. 19E
1910 ↘
FIG. 19F
1912 ↘
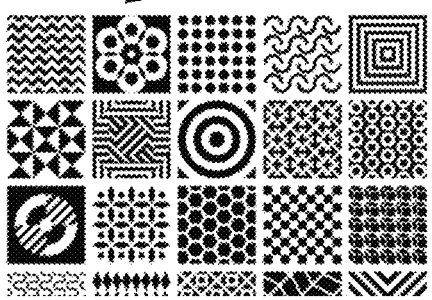
FIG. 19G
1914 ↘
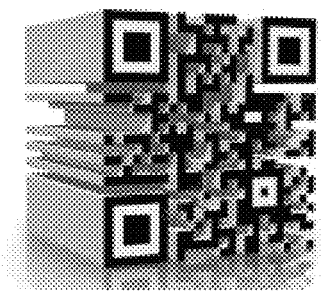
FIG. 19H

| | # of Samples | Average of Burst strength (lbf) | StdDev of Burst strength (lbf) |
|---|---|---|---|
| 0.5% | 35 | 53.4 | 6.14 |
| 45 deg | 5 | 49.7 | 1.46 |
| Warp | 15 | 48.5 | 2.64 |
| Weft | 15 | 59.5 | 3.75 |
| 2.0% | 20 | 47.0 | 4.67 |
| 45 deg | 5 | 43.0 | 2.38 |
| Warp | 10 | 45.7 | 2.64 |
| Weft | 5 | 53.5 | 2.02 |
| 8.0% | 15 | 40.7 | 5.67 |
| 45 deg | 5 | 37.1 | 3.39 |
| Warp | 5 | 38.8 | 3.00 |
| Weft | 5 | 46.2 | 5.77 |
| Unmarked | 15 | 58.7 | 2.36 |
| Unmarked | 15 | 58.7 | 2.36 |

| | # of Samples | Average of Burst Strength (lbf) | StdDev of Burst Strength (lbf) |
|---|---|---|---|
| 1mm Spacing | 35 | 41.1 | 17.84 |
| 0.005mm | 15 | 59.4 | 3.75 |
| 0.05mm | 5 | 40.6 | 2.69 |
| 0.1mm | 5 | 28.2 | 2.27 |
| 0.25mm | 5 | 25.9 | 1.16 |
| 0.5mm | 5 | 14.5 | 1.00 |

| | # of Samples | Average of Burst Strength (lbf) | StdDev of Burst Strength (lbf) |
|---|---|---|---|
| 0.5% | 15 | 27.4 | 6.40 |
| 45deg | 5 | 22.7 | 1.09 |
| Warp | 5 | 35.8 | 2.17 |
| Weft | 5 | 23.5 | 1.58 |
| 2% | 15 | 19.9 | 3.564 |
| 45deg | 5 | 19.2 | 1.39 |
| Warp | 5 | 24.2 | 1.57 |
| Weft | 5 | 16.3 | 0.86 |
| Unmarked | 5 | 39.5 | 1.22 |
| Unmarked | 5 | 39.5 | 1.22 |

| Row Labels | # of Samples | Average of Burst Strength (lbf) | StdDev of Burst Strength (lbf) |
|---|---|---|---|
| 0.5% | 10 | 103.6 | 3.00 |
| Warp | 5 | 101.2 | 0.82 |
| Weft | 5 | 106.0 | 2.28 |
| 2% | 10 | 99.5 | 5.30 |
| Warp | 5 | 95.0 | 3.25 |
| Weft | 5 | 103.9 | 1.71 |
| Unmarked | 4 | 109.6 | 3.70 |
| Unmarked | 4 | 109.6 | 3.70 |

| | # of Samples | Average of Burst Strength (PSI) | StdDev of Burst Strength (PSI) |
|---|---|---|---|
| 0.5% | 15 | 82.5 | 2.32 |
| 45deg | 5 | 82.6 | 2.27 |
| Course | 5 | 81.7 | 3.11 |
| Wale | 5 | 83.1 | 1.66 |
| 2.0% | 15 | 79.8 | 3.19 |
| 45deg | 5 | 79.7 | 0.82 |
| Course | 5 | 78.3 | 5.25 |
| Wale | 5 | 81.3 | 1.31 |
| 8.0% | 15 | 66.6 | 2.54 |
| 45deg | 5 | 65.6 | 2.37 |
| Course | 5 | 67.7 | 1.99 |
| Wale | 5 | 66.6 | 3.19 |
| Unmarked | 6 | 83.5 | 5.09 |
| Unmarked | 6 | 83.5 | 5.09 |

| | # of Samples | Average of Burst Strength (PSI) | StdDev of Burst Strength (PSI) |
|---|---|---|---|
| 0.5% | 15 | 67.1 | 2.18 |
| 45deg | 5 | 66.0 | 2.44 |
| Course | 5 | 68.2 | 2.39 |
| Wale | 5 | 67.0 | 1.33 |
| 2.0% | 15 | 67.0 | 2.35 |
| 45deg | 5 | 68.7 | 0.63 |
| Course | 5 | 66.6 | 3.07 |
| Wale | 5 | 65.7 | 1.89 |
| Unmarked | 4 | 63.9 | 1.61 |
| Unmarked | 4 | 63.9 | 1.61 |

| | # of Samples | Average of Burst strength (lbf) | StdDev of Burst strength (lbf) |
|---|---|---|---|
| 0.5% | 8 | 279.9 | 20.40 |
| Warp | 4 | 270.7 | 27.12 |
| Weft | 4 | 289.1 | 3.03 |
| 2% | 8 | 275.8 | 17.10 |
| Warp | 4 | 283.5 | 9.80 |
| Weft | 4 | 268.0 | 20.64 |
| 8% | 8 | 273.5 | 16.77 |
| Warp | 4 | 276.9 | 12.79 |
| Weft | 4 | 270.1 | 21.48 |
| Unmarked | 4 | 270.0 | 29.08 |
| Unmarked | 4 | 270.0 | 29.08 |

| | # of Samples | Average of Tensile Strength (lbf) | StdDev of Tensile Strength (lbf) |
|---|---|---|---|
| 0.5% | 6 | 45.7 | 0.45 |
| Horizontal | 3 | 45.6 | 0.57 |
| Vertical | 3 | 45.8 | 0.39 |
| 2.0% | 6 | 43.4 | 0.35 |
| Horizontal | 3 | 43.3 | 0.32 |
| Vertical | 3 | 43.5 | 0.42 |
| 8.0% | 6 | 40.1 | 0.36 |
| Horizontal | 3 | 40.0 | 0.19 |
| Vertical | 3 | 40.1 | 0.52 |
| Unmarked | 3 | 46.7 | 0.12 |
| Unmarked | 3 | 46.7 | 0.12 |

INDICATOR MARKING TECHNOLOGY FOR TEXTILES

CROSS-REFERENCE TO RELATED APPLICATIONS

This application is a continuation of International PCT Application No. PCT/US2020/022796 filed on Mar. 13, 2020, entitled "Indicator Marking Technology for Textiles," which claims the benefit of U.S. Provisional Application No. 62/818,099 entitled "Indicator Marking Technology for Textiles," filed Mar. 13, 2019, the disclosures of which are incorporated by reference herein in their entireties.

TECHNICAL FIELD

The invention relates to improved indicator marking for textiles, as well as related methods, designs, systems and models. More specifically, disclosed herein are improved methods, designs and/or systems for incorporating markings and/or other visual and/or tactilely identifiable indicia on woven, knitted, nonwoven, braided and/or felted textiles used for medical textile, including implants, prostheses, and medical grafts.

BACKGROUND OF THE INVENTION

In many cases, it is desirous for a manufacturer to provide markings or other indicators on medical textiles, including implant devices and prostheses, that can assist with further processing and/or use of the device. While different colored threads and/or pigments might be incorporated into the device to provide various markings thereon by weaving, knitting, braiding etc., one challenge presented when using textiles is that the fibers of the textile often distort and/or skew during subsequent processing, which can change or otherwise alter the position and/or alignment of the markings. For example, in vascular grafts, the individual strands and/or portions of the graft tend to distort and/or skew during the three-dimensional "opening" process, especially in areas of the graft that are tapered or conical (in 3-dimensions). In general, the distortion and/or skewing movements can significantly disrupt the position and/or alignment of the markings or other indicators placed into the textile in the 2-dimensional state. In addition, the use of imbedded colorants and/or different fiber types during textile manufacture will often significantly affect the strength, flexibility, performance and/or durability of the resulting prosthesis.

Currently, a wide variety of inks are used to provide externally visible indicator and/or alignment marks on textile prosthesis. However, using pigments, inks and/or other supplementary marking materials (as well as colorant additives to polymers) have many disadvantages, including requiring costly additional equipment to accomplish, the ink marking(s) may be skewed or shifted from an intended location depending upon the inking technology selected, the pigment and/or inks may elute from the implant during use, and/or the process allows for the use of simple and large sized marks. In addition, ink markings may be negatively affected or altered by subsequent manufacturing processes and/or may require additional biocompatibility testing for the final product, all of which can be undesirable. The overall print quality is poor, and limiting the amount of information that can be marked.

Another marking method currently in use with medical textiles is physical stamping and/or crimping of individual fibers and/or fiber bundles to provide externally-viewable indicia and/or markings. Aside from the additional expense and equipment needed for such activities, the physical alteration and/or compression of various fibers within a given textile might be undesirable in some applications, as it may also alter the desired shape and/or mechanical performance of the textile.

Furthermore, other techniques such as infrared lasers also have its disadvantages. Laser marking is a non-contact method that involves either producing a color change on a surface or within the bulk of the material, or a change in surface relief (e.g. engraving) or texture that is easily visible. Laser marking usually employs ($CO_2$, solid state, or fiber) lasers operating in the infrared. The marking process itself is a thermal interaction; material is heated until it bleaches, carbonizes or ablates in order to produce a color contrast. However, this heating can alter the chemical structure of the material in the heat-affected zone (HAZ) such as charring, and also produces some surface relief. This texture can offer a place for bacteria to settle and grow, and may be difficult to clean. Laser engraving to limited to specific materials due to its thermal interaction affecting the shape and/or mechanical performance of the materials.

In many cases, it remains desirous for a manufacturer to provide markings or other indicators on medical textiles that can assist with further processing and/or use of the medical textile and/or implant and do not introduce additional material(s) and/or adversely compromise the mechanical and/or material properties to a significant degree.

BRIEF DESCRIPTION OF THE SEVERAL VIEWS OF THE DRAWINGS

FIG. 1 illustrates a table listing the different embodiments of marking indicator techniques;

FIG. 5A-5B illustrates a graphical representation of one embodiment of UV power settings grid;

FIG. 13 depicts a magnified view of a medical textile with emboss marking;

FIG. 16 depicts a front view of one embodiment of a woven textile;

FIGS. 17A-17E depicts front views of different patterns of a woven textile;

FIGS. 19A-19H depicts different embodiments of types of marking indicators;

BRIEF SUMMARY OF THE INVENTION

Figure 2:
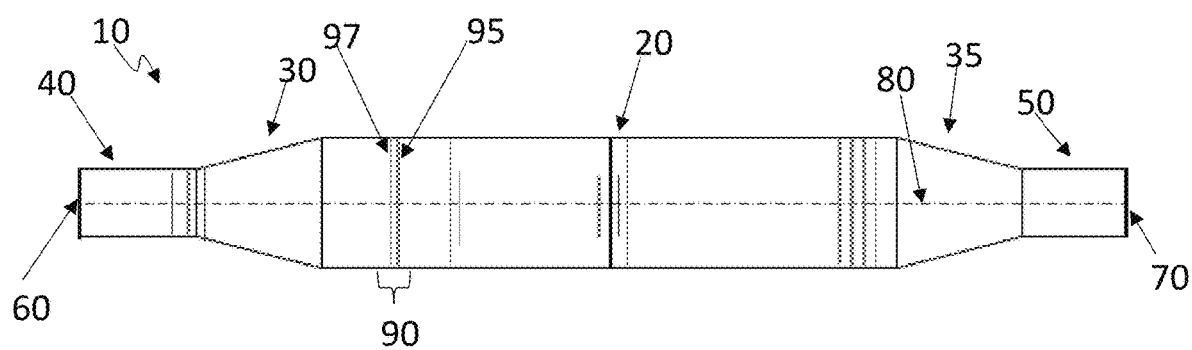
FIG. 2 depicts an exemplary embodiment of a vascular medical textile with marking indicators.

The inventions disclosed herein include the realization of a need for improved marking and/or other techniques for providing visual or other indicators and/or alignment markings on and/or into medical textiles, prosthesis and/or implantable devices that do not affect the overall mechanical performance of the medical textile. In various embodiments, the disclosed concepts can include markings and/or other indicators that may be integrated into the manufacture of the graft in a 2-dimensional state, while in other embodiments markings and/or other indicators may be applied and/or integrated into the medical textile in a 3-dimensional state, while still other embodiments may apply and/or integrate markings and/or other indicators to the medical textile in both 2-dimensional and 3-dimensional states at various steps along the medical textile manufacturing and assembly process. Accordingly, the material characteristics or the material properties of the medical textile may be modified and/or adapted to ensure that the overall mechanical performance of the medical textile is conserved and/or preserved after the medical textile is marked with preferred marking indicator technique. The material characteristics or properties may comprise modifying the yarn (e.g., the yarn material, yarn texture, yarn denier, yarn twists-per-inch (TPI), one or more yarn filaments, filament diameter, ends-per-inch (PPI), picks-per-inch (PP), the direction of the marking indicator technique, and/or any combination thereof.

In various embodiments, the integration and/or application of markings and/or other indicators will desirably have little to no effect on the structural integrity, flexibility and/or mechanical performance of the textile device and/or individual fibers or filaments thereof (i.e., "minimal marking techniques"). For example, various embodiments can include the use of "cold" UV laser marking and/or ultrasonic marking of portions of individual threads and/or fibers of the textile, while other embodiments can further include techniques involving various methods of inking, colorizing, physically stamping, crimping and/or embossing of individual fibers and/or fiber bundles to provide externally-viewable indicia and/or markings.

In one embodiment, a marked medical textile comprises a woven medical textile; the woven medical textile including a warp and a weft; and a marking indicator, the marking indicator being aligned with the weft direction of the woven medical textile to preserve strength and flexibility. The marking indicator comprises a marking from a UV laser. The woven medical textile comprises a plain weave wherein the woven medical textile comprises polyethylene terephthalate (PET). The marking indicator comprises characters or graphics, the characters comprises a symbol, alphabet letters, shapes, numbers, alphanumeric, and/or any combination thereof and/or the graphics comprises a logo, a photo, an image, patterns, 2D barcodes, 3D barcodes and/or any combination thereof. the marking indicator comprises a size, the size is a range between 0.001% to 100% of total area of textile.

In another embodiment, the method of marking a surface of a medical textile without significantly affecting the strength or flexibility of the medical textile comprising the steps of creating a woven medical textile, the woven medical textile having a weft and a warp; marking at least a portion of the surface of the medical textile using an Ultra Violet (UV) laser beam; and aligning the marking in the weft direction. The woven medical textile comprises a plain weave. The woven medical textile comprises polyethylene terephthalate (PET). The marking comprises characters or graphics, the characters comprises a symbol, alphabet letters, numbers, and/or any combination thereof. The marking indicators comprises a size, the size is a range between 0.001% to 100% of total area of textile.

In other embodiments, various other textile marking techniques can be used in combination with the disclosed minimal marking techniques to provide a hybrid marking strategy, such as where medical grade inks and/or other colorants can be utilized to provide some of them markings and/or other indicators on the textile device. In some embodiments, the colorants and/or inks can be applied to one or more external surfaces of the textile and/or textile fibers in the 2-dimensional and/or 3-dimensional state, while in other embodiments the colorants and/or inks can be formulated and processed into the various fibers. In still other embodiments, the use of colorants and/or inks may be less desirous, especially where such substances may be required to undergo additional biocompatibility testing and/or where a patient may be unduly sensitive to such substances.

In various embodiments, one or more individual "marker" threads incorporating a colorant and/or other differentiating feature (i.e., a different surface texture and/or different material characteristics) can be woven, knitted, braided and/or felted into a medical textile, wherein the marker threads can provide an indicator and/or other externally visible and/or tactilely identifiable markings on the textile material that facilitate the further processing and/or use of the material structure. In some embodiments, the marker thread can comprise longitudinally extending markers, which may experience minimal disruption and/or mal-alignment during the 2-dimensional to 3-dimensional "opening" process.

The various embodiments disclosed herein can include methods for determining appropriate marking method(s) for a given implantable textile device and/or textile device manufacturing method. For example, a given textile device manufacturing method and/or prothesis design may be particularly prone to distortion in one or more areas of the device, which may preclude the inclusion of woven markers in those locations during the 2-dimensional manufacturing process, which may predispose the inclusion of such markers using a method suitable for application/integration after the medical textile has reached its 3-dimensional state. Desirably, the pattern and manufacturing techniques for the various markings and/or other indicators will desirably minimize the opportunity for skewing and/or other distortion of the markings during the various manufacturing and/or assembly processes.

In various embodiments, the markings and/or other externally visible indicators on the medical textile may be integrated and/or applied using a combination of the previously disclosed techniques. For example, one or more longitudinally extending marker threads may be woven into an implantable textile device, and the woven marker threads can subsequently be utilized (i.e., for graft alignment on a mandrel or other tooling) to assist with the alignment and application/integration of additional markers, such as by ink application and/or physical stamping, crimping and/or embossing of individual fibers and/or fiber bundles to provide the additional externally-viewable indicia and/or markings—circumferential ring markings on the textile, for example. In another exemplary embodiment, a UV sensitive colorant (which potentially changes colors in the presence of applied UV light) or other substance(s) may be initially formulated into one or more threads of the implant, with one or more of these threads used for weaving and/or knitting the implant, and/or a cold UV laser (or other marking device) could be utilized to alter the coloration or other characteristic to "mark" portions of individual threads and/or fibers of the implant.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

In many instances, it would be highly desirous for a manufacturer to provide markings or other indicators on a medical textile product that can assist in various ways with further processing and/or use of the textile and/or subsequently manufactured device. Such marking could include highly durable indicators, which may be visible on the finished textile prosthesis, as well as less durable markings which might fade, be concealed and/or be removed during subsequent processing. In general, a highly desirable marking technique for a medical textile product would provide such marking(s) without significantly affecting the strength, durability, flexibility and/or performance of the textile prosthesis, and more desirably not require additional biocompatibility testing.

Medical Textiles

A wide variety of medical textiles, including implantable textiles and/or devices incorporating medical textiles, may benefit from the various marking techniques described herein. Such products can include, but should not be limited to, implantable medical textiles, non-implantable medical textiles, extracorporeal medical textiles and/or healthcare and hygienic medical textiles such as cardiovascular and vascular grafts and implants, artificial ligaments and tendons, sutures, soft tissue implants, dialysis devices, artificial livers, mechanical lungs, ophthalmologic materials, dental materials, gauzes, crepe bandages, bed linens, surgical masks, etc. The medical textiles may comprise woven textiles, knit textiles, braided textiles and/or non-woven textiles. Such textiles may be manufactured with standard methods known in the art. More specifically, the textiles may be manufactured according to U.S. Pat. Nos. 6,994,724; 7,921,678; 10,364,518; R46779 and WO2008109019, all of which the disclosures are incorporated by reference herein in their entireties.

Each medical textile may comprise one or more material properties. The one or more material properties can be modified and/or adapted to ensure that the overall mechanical performance of the medical textile is conserved and/or preserved after the medical textile is marked with the preferred marking indicator technique, as well as using the marking indicator technique that produces the least amount of textile damage. The modifying of the one or more material characteristics or properties may comprise a yarn material, yarn texture, yarn denier, yarn twists-per-inch (TPI), one or more yarn filaments, one or more yarn diameter, filament diameter, ends-per-inch (PPI), picks-per-inch (PPI), the yarn material, filament or textile density, the direction of the marking indicator technique, and/or any combination thereof.

In one embodiment, the medical textile comprises a plurality of yarns. Yarn, as used herein is a strand of textile fiber made up of one or more filaments or one or more fibers. Each yarn may include a single filament (monofilament), multiple or plurality of filaments (multifilament), staple fibers, wire and/or any other material capable of being woven or knitted. The plurality of yarns may be textured or flat, and may be of any opacity, including bright, semi-dull, full-dull and/or any combination thereof. The plurality of yarns may comprise resorbable yarn material, non-absorbable yarn material and/or a combination thereof.

The one or more filaments may be non-twisted (e.g. zero twists or zero TPI) or non-interlaced. Alternatively, the one or more filaments may comprise one or more twists or one or more interlacing. A twist is the spiral arrangement of filaments around the yarn's axis, and it is specified by number of turns per unit length—otherwise known as turns per inch (TPI). In one embodiment, the one or more twists may include a range of 1 twist to 20 twists; the range may include 1 twist to 15 twists; the range may include 1 twist to 10 twists; the range may include 1 twist to 5 twists; the range may include 5 twists to 15 twists. In a preferred embodiment, the twists may include 6.5 TPI to 12 TPI, and/or at least one twist. The S or Z direction of the twist refer to a specific spiral direction. The S twist refers to the direction of the twist or spiral of the filaments is parallel to the center bar of the letter "S." The Z twist refers to the direction to the twist or spiral of the filaments is parallel to the center bar of the letter "Z.".

The plurality of yarns may comprise a linear density. The linear density includes 40 denier (44 decitex) or higher, less than 40 denier, 30 denier or less, 20 denier or less. More specifically, the linear density includes 5 denier to 1000 denier. More specifically, the linear density may include 10 denier to 60 denier or 10 denier to 100 denier. Denier is the weight in grams of 9,000 meters of yarn. The thickness of the woven textile may be about 25 mil or less, about 21 mil or less, about 17 mil or less, about 10 mil or less, about 7 mil or less, about 6 mil to about 3 mil, about 4 mil or less, about 4.3 mil to about 5.5 mil, about 4.0 mil, or about 3.2 mil or less, or about 2 mil or less. A mil is a unit of length, in which 1 mil is equal to 0.001 inch. The thickness of the textile may be measured by standard tests (ISO 7198). The textile may have a number of threads per unit area of greater than or equal to about 10 yarns per $cm^2$, greater than or equal to about 100 yarns per $cm^2$, greater than or equal to about 150 yarns per $cm^2$, or greater than about 177 yarns per $cm^2$, greater than or equal to about 250 yarns per $cm^2$. The number of yarns is calculated by adding the number of warp yarns and the number of weft yarns in a unit area, for an example area is $cm^2$.

The plurality of yarns may comprise a one or more filaments. The one or more filaments may comprise a diameter, the diameter may include a range of 30 μm to 400 μm, the diameter may include a range of 30 μm to 210 μm. The diameter may also include a range of 30 μm to 175 μm, the diameter may include a range of 30 μm to 150 μm, the diameter may include a range of 30 μm to 125 μm, the diameter may include a range of 30 μm to 100 μm, the diameter may include a range of 30 μm to 75 μm, and/or the diameter may include a range of 30 μm to 50 μm. In a preferred embodiment, the diameter may include a range of 45 μm to 90 μm.

In one embodiment, the medical textile comprises a textile structure, the textile structures include a woven medical textile, a knitted medical textile and/a braided medical textile. In a preferred embodiment, the medical textile comprises a woven medical textile 1600 as shown in FIG. 16. A woven textile involves the interlacing of two or more yarns to create a fabric or fabric textile. The woven medical textile 1600 includes a primary yarn and a secondary yarn. The primary yarn may comprise a warp 1602 and/or weft 1604. The secondary yarn may comprise a warp 1602 and/or weft 1604. The warp 1602 and/or weft 1604 used in weaving to turn thread or yarn into fabric as shown in FIG. 16 and are used to describe the direction of the yarn compared to the loom. The warp yarns 1602 are positioned vertically, lengthwise or longitudinally and are held stationary in tension on a frame or loom—they act as the beam or center that the weft 1604 is interlaced through. The weft 1604 is positioned horizontal, latitudinally or transverse and is drawn through and inserted over-and-under the warp in a variety of weave patterns. The warp 1604 must be a strong material to be held under high tension during the weaving process, unlike the weft 1604 which carries almost no tension. Accordingly, the weft or woof 1604 crosses the warp 1602, binding the warp threads at either side to form the selvage 1606. The warp 1602 does not have to be stretched on a loom the way the weft 1604 is because of the crossing or looping, so it can generally be less strong. The primary yarn and the secondary yarn may be the same materials, and/or the primary yarn and the secondary yarn may be different materials.

Examples of the weave patterns may comprise plain weave 1702, twill weave 1700, satin weaves 1704, 1706, cross twill weave 1708, and/or any combination thereof as shown in FIGS. 17A-17E. The plain weave 1702, also known as calico, tabby, taffeta, or homespun weaves, the weft passes over alternate warp threads, requiring two harnesses only. The relatively simple construction suits it to cheap fabrics, heavy yarns, and printed designs. Variations are produced by the use of groups of yarns, as in basket weave and monk's cloth, or by alternating fine and coarse yarns to make ribbed and corded fabrics, as the warp-ribbed Bedford cord, piqué, and dimity and the weft-ribbed poplin, rep, and grosgrain. The second primary weave, twill weave 1600, shows a diagonal design made by causing weft threads to interlace two to four warp threads, moving a step to right or left on each pick and capable of variations, such as herringbone and corkscrew designs. The satin weaves 1704, 1706 has floating or overshot warp threads on the surface which reflect light, giving a characteristic luster. When the uncrossed threads are in the weft, the weave is called sateen. The satin weaves 1704, 1706 may further comprise satin weave 1/7 1704 or satin weave 1/4 1706. Other weave patterns may be contemplated, including rib weave, basket weave, leno weave, oxford weave, waffle weave, pile weave, crepe weave, lappet weave, tapestry weave, checkered weave, and/or any combination thereof.

In another embodiment, the woven medical textile comprises ends-per-inch (EPI). EPI is the number of warp threads per inch of a woven textile. In general, the higher the ends per inch, the finer the fabric. The EPI includes a range of 80 EPI to 450 EPI; the EPI may include a range of 80 EPI to 400 EPI; the EPI may include a range of 80 EPI to 350 EPI; the EPI may include a range of 80 EPI to 300 EPI, the EPI may include a range of 80 EPI to 250 EPI; the EPI may include a range of 80 EPI to 200 EPI; the EPI may include a range of 80 EPI to 150 EPI; the EPI may include a range of 150 EPI to 400 EPI. In a preferred embodiment, the EPI may include a range of 150 to 350 EPI.

In another embodiment, the woven medical textile comprises picks-per-inch (PPI). PPI is the number of weft threads per inch of a woven textile. In general, the higher the PPI, the finer the fabric. The PPI includes a range of 10 PPI to 450 PPI; the PPI may include a range of 40 PPI to 400 PPI; the PPI may include a range of 80 PPI to 350 PPI; the PPI may include a range of 80 PPI to 300 PPI, the PPI may include a range of 80 PPI to 250 PPI; the PPI may include a range of 80 PPI to 200 PPI; the PPI may include a range of 80 PPI to 150 PPI. In a preferred embodiment, the PPI may include a range of 100 to 250 PPI.

In another embodiment, the medical textile comprises a non-woven textile. A non-woven textile comprises a fabric-like material made from staple fiber (short) and long fibers (continuous long), bonded together by chemical, mechanical, heat or solvent treatment. Accordingly, non-woven fabrics are broadly defined as sheet or web structures bonded together by entangling fiber or filaments (and by perforating films) mechanically, thermally or chemically. They are flat or tufted porous sheets that are made directly from separate fibers, molten plastic or plastic film. They are not made by weaving or knitting and do not require converting the fibers to yarn.

Figure 18A:
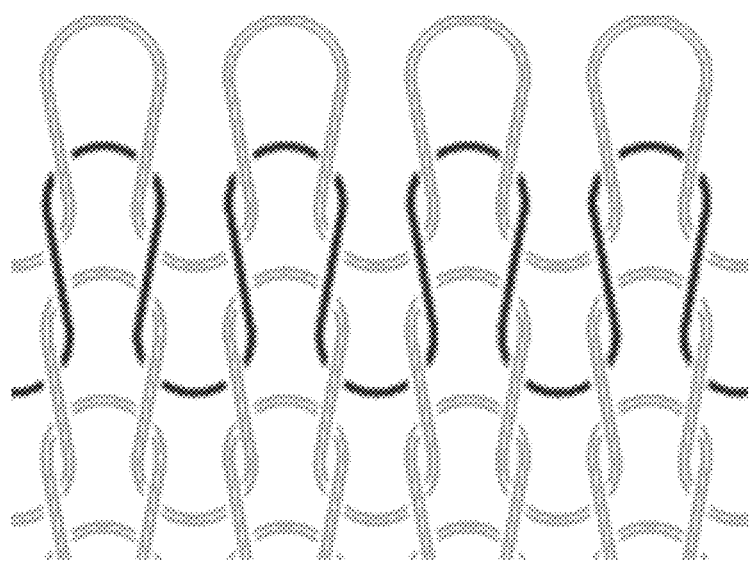
FIGS. 18A-18B depicts front views of knitted textiles.
Figure 18B:
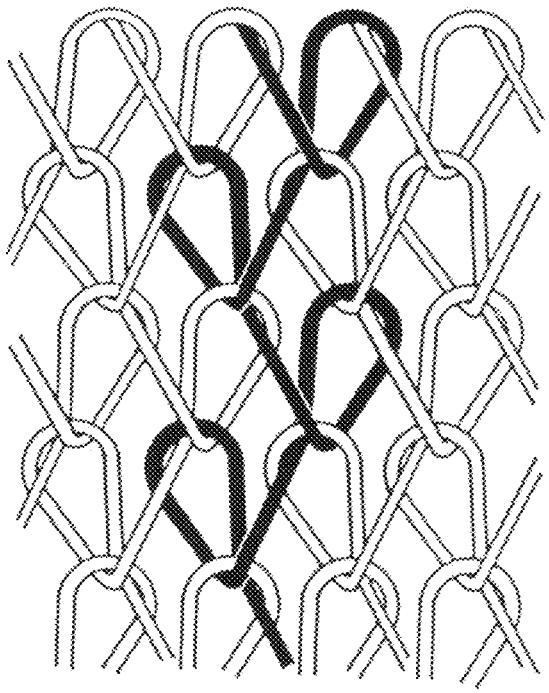

In another embodiment, the medical textile comprises a knitted textile 1800, 1802 as shown in FIGS. 18A-18B. Knitted textiles 1800, 1802 are fabrics made by one continuous thread or yarn. Knitted textiles are created by a single thread or yarn to create interlocking loops by use of needles, instead of the multiple warp yarns used in woven fabrics. The knitted textile 1800, 1802 comprises a primary yarn, the primary yarn forming a primary plurality of loops, the primary plurality of loops is positioned vertically or longitudinally in repeating rows, the primary plurality of loops are ribs or wales. The knitted textile 1800, 1802 may further comprise a secondary yarn, the secondary yarn forming a secondary plurality of loops, the secondary plurality of loops is positioned horizontally or latitudinally in repeating rows, the secondary plurality of loops are courses. In one exemplary embodiment, the knitted textile 1800, 1802 comprises a primary yarn and a secondary yarn. Alternatively, the knitted textile 1800, 1802 comprises at least one yarn. The primary yarn and the secondary yarn comprise the same yarns or different yarns.

Furthermore, the knitted fabric 1800, 1802 comprises a weft knit 1800, a warp knit 1802, a specialized weft knit (not shown). Weft or filling knits 1800 are constructed from at least one yarn and/or a primary or secondary yarn that is fed into knitting machine in a horizontal direction to create a plurality of loops in the horizontal or latitudinal direction. Warp knits 1802 are constructed from at least one yarn and/or a primary or secondary yarn that is fed into a knitting machine in a vertical or longitudinal direction to create loops in the vertical or longitudinal direction. The weft knits 1800 may comprise single weft knits or double weft knits. The single weft knits may comprise single Jersey or Lacoste. The double weft knits may comprise rib knit, purl knit, interlock knit, cable fabric, Bird's Eye, Cardigans, Milano Ribs, Pointelle and/or any combination thereof. The specialized weft knits comprise Intarsia knit, Jacquard Jersey knit, Knitted Terry knit, Knitted Velour, Sliver Knit, Fleece, and/or any combination thereof. The warp knits comprise Tricot, Raschel and/or any combination thereof.

In another embodiment, the medical textile comprises a braided textile (not shown). The braiding interlaces three or more yarns or bias-cut textile strips in such a way that they cross one another and are laid together in diagonal formation, forming a narrow strip of flat or tubular fabric. The braided textile includes a flat braid, a soutache braid, circular/round braids, a three-dimensional braid, and/or any combination thereof. The braided architecture of provides high strength, stiffness, and structural integrity, making them suitable for a wide array of applications.

In another embodiment, the medical textile, the one or more yarns, and/or the one or more filaments comprises a material. The material comprising polyethylene terephthalate (PET), polyurethane (PU), polytetrafluoroethylene (PTFE), expanded polytetrafluoroethylene (PTFE), polycarbonates ("PC"), ABS, polypropylene (PP), polystyrene, polyethylene (PE), polyester, polyacetal, elastomers, thermoplastic polyurethane ("TPU"), nylon, ionomers, polyvinyl chloride ("PVC") and/or any combination thereof, as well as other medical grade materials known by those of ordinary skill in the textile art. The polyethylene (PE) comprises ultra-high molecular weight polyethylene (UHMWPE), low density polyethylene (LDPE), medium density polyethylene (MDPE) and/or any combination thereof.

In another embodiment, the medical textile may have a continuous textile structure or material properties throughout the length of the textile and/or different textile structures or material properties throughout the length of the textile. Accordingly, the medical textile may include at least one textile structures. The medical textile may comprise a length and a longitudinal axis. The medical textile may further comprise at least one textile structure, the textile structure may be the same at least one textile structure along the length of the medical textile, and/or the same textile structure along the longitudinal axis of the medical textile. Alternatively, the medical textile may comprise a plurality of textile structures. Each of the plurality of textile structure may include different textile structures and/or the plurality of textile structures may include different textile structures. The textile structures may comprise woven, non-woven, knitted, braided and/or any combination thereof. In addition, the medical textile may comprise a first textile structure and a second textile structure. The first and the second textile structure comprises the same textile structure and/or the first and the second textile structure comprises different textile structures.

Alternatively, the medical textile may comprise a first region and a second region. The first region comprises a first textile structure and a first one or more material properties, and the second region comprises a second textile structure and a second one or more material properties. The first region textile structure and the second region textile structure may comprise the same textile structures and/or the different textile structures. The first region one or more material properties and the second region one or more material properties may comprise the same textile material properties or different textile material properties. Accordingly, the first region or the second region may comprise a marking indicator. At least a portion of the first region and at least a portion of the second region may comprise at least a portion of the marking indicator. For example, the medical textile comprises a first region and a second region. The first region including the same textile structure as the second region. The first region including different material properties than the second region. The first region including a first burst strength and the second region including a second burst strength. The first region comprising an indicator marking, the first burst strength being greater than the second burst strength. Of course, the first and second regions may be used interchangeably. The textile structures comprise woven, non-woven, braided, knitted and/or any combination thereof. The marking indicator may align with preferred direction of at least one yarn (or a primary yarn or a secondary yarn), the preferred direction includes a horizontal direction, a vertical direction and/or an oblique direction. The preferred direction may correspond to a course, a wale, a weft and/or weave. The one or more material properties of the first region may be the same or different than the one or more material properties of the second region. The one or more material properties comprises at least 5 twists-per-inch (TPI), higher density filaments and/or yarns, a denier of at least 20 denier to 60 denier, high strength material, having balanced ends, where PPI is substantially equal to EPI and/or any combination thereof.

Marking Identifier or Marking Indicator Techniques

FIG. 1 depicts a table of various exemplary techniques for incorporating visually and/or tactilely identifiable markings and/or other indicia into/onto a medical textile implantable device in the 2-dimensional and/or 3-dimensional state, and/or various combinations thereof. These techniques include (1) UV Laser Marking/Cold Marking, (2) Embossing, (3) Stamping/Crimping, (4) Ultrasonic Marking, (5) Printing, and (6) Weaving/Knitting/Braiding. In addition, a variety of other techniques could be utilized to provide such marking and/or other indicia, including (1) physical marking (i.e., pencil, pen, markers, paint), (2) sewing stripes, no thread and/or punching, (3) etching, (4) pattern changes and/or yarn removal, (5) coating, UV curing to make stripes, utilizing masking agents, (6) utilizing polarized light to view markings, (7) shadow marking (i.e., inverse stencil or masking agent marking), (8) laser cutting holes or stripes into medical textile material, (9) dyeing parts—with or without masking agent, (10) using a removable sheath with stripe placement, (11) bruising the medical textile (i.e., ref stamping), (12) utilizing stickers or adhesive materials, and/or (13) incorporating a physical change in density to the fabric (i.e., spreading the fabric manually), and/or any combination thereof. If desired, one or more of any of the techniques described herein could be utilized on the textile implantable device in the 2-dimensional and/or 3-dimensional state, and/or could be utilized in any combinations thereof.

Any of the marking indicator techniques may be used to mark a medical textile, known herein as a "marked" medical textile. The "marked" medical textile comprises a medical textile, and a marking indicator. The medical textile comprises a primary yarn and a secondary yarn. Alternatively, the medical textile comprises a primary yarn with a primary direction and a secondary yarn with a secondary direction. The primary yarn may comprise a warp, weft, course, and/or wale. The secondary yarn may comprise a warp, weft, course and/or wale. The primary yarn and the secondary yarn may comprise a same material. The primary yarn and the secondary yarn may comprise different materials. The marking indicator aligns with the primary or secondary yarn. Alternatively, the marking indicator aligns with and/or is parallel to the primary yarn in a primary direction and/or the marking indicator aligns with and/or is parallel to the secondary yarn in a secondary direction. Accordingly, the marking indicator aligns or is disposed in 45 degree angle relative to the primary yarn and the secondary yarn. In another embodiment, the marking indicator aligns or is disposed in 30 degree angle relative to the primary yarn and the secondary yarn, or 60 degree angle relative to the primary yarn and the secondary yarn, or 15 degree angle relative to the primary yarn and the secondary yarn, or any angle between 1 degree to 180 degree relative to the primary yarn and the secondary yarn.

FIG. 2 depicts an exemplary embodiment of a vascular medical textile 10 that can be manufactured in a 2-dimensional shape on a Dobby or Jacquard type loom (or other loom or manufacturing equipment types already developed and/or that may be developed in the future), such as is described in U.S. Pat. No. 5,127,919, the disclosure of which is expressly incorporated herein by reference. In this embodiment, the medical textile 10 includes a central region 20, a first tapered section 30, a second tapered section 35, a first end section 40, a second end section 50, with a first proximal end 60 and a second distal end 70. The medical textile 10 further desirably includes one or more oblique markers, one or more longitudinal markers 80, and one or more circumferential markers 90. In the disclosed embodiment, the circumferential markers 90 can include directional indicators comprising a thick line 95 paired with a thin line 97 (or various other line sizes, colors, thickness and/or line combinations), which can desirably provide an index and/or indicator to a manufacturing technician and/or physician as to the direction of manufacturing or other medical textile characteristics (i.e., top down or bottom up) for various reasons, including proper medical textile alignment during implantation. The one or more oblique markers include marking indicators that are disposed obliquely across the primary and secondary yarn, the oblique markers comprise a range of 1 degrees to 180 degrees; the range may further comprise 15 degrees to 75 degrees, the range may further comprise 30 degrees to 60 degrees, the range may further comprise 45 degrees to 60 degrees. In another embodiment, the one or more oblique markers including marking indicators disposed obliquely across a medical textile including a first region and a second region. The first region and the second region of the medical textile comprising a textile structure and one or more material properties. The textile structure of the first region may be the same as the second region, and/or the textile structure of the first region is different than the textile structure of the second region. The textile structure comprising woven, non-woven, braided, knitted, and/or any combination thereof. The one or more material properties of the first region may be the same or different than the one or more material properties of the second region. The one or more material properties comprises at least 3 twists-per-inch (TPI), higher density filaments and/or yarns, a denier of at least 20 denier to 60 denier, high strength material, having balanced ends, where PPI is substantially equal to EPI and/or any combination thereof.

Figure 3:
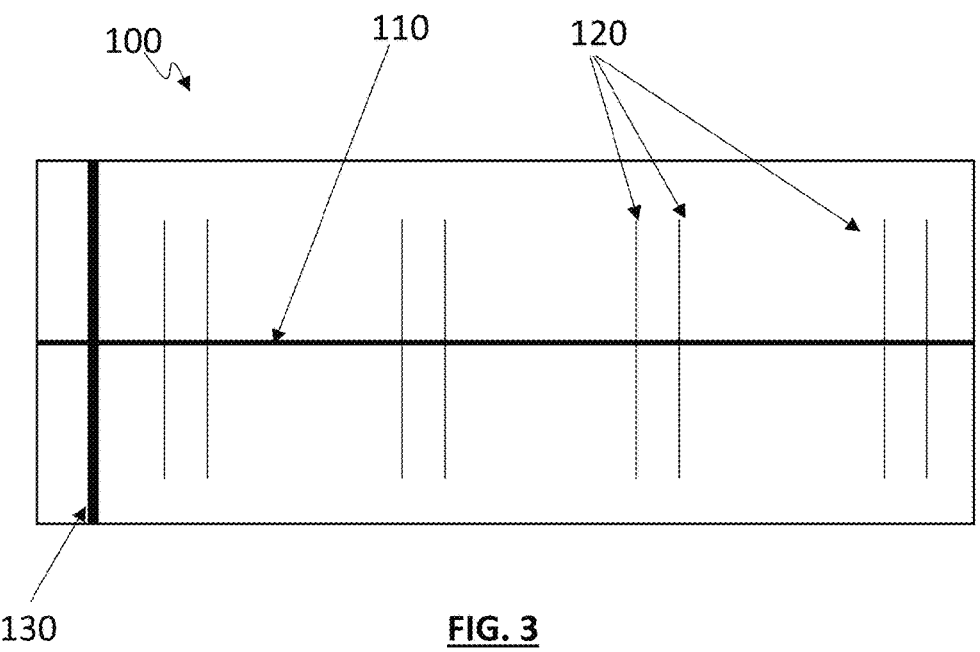
FIG. 3 depicts a magnified view of one embodiment of a vascular medical textile with marking indicators.

FIG. 3 depicts a portion of one exemplary embodiment of a medical textile 100 incorporating markings and/or other indicators as disclosed herein. The medical textile 100 can include one or more longitudinal markers 110, with one or a series of circumferential makers 120 that can be created using a UV laser marking device. Also depicted is a circumferential marker 130 created using a physical embossing or "flattening" process, which desirably creates a slightly flattened line on the surface of the medical textile which can be visually and/or tacitly identified. If desired, the medical textile could be placed on a mandrel with raised features that transfer to the fabric during compression and/or heat set processes. Similar procedures could be performed on flat sheets with a plate or other device that the fabric can be placed on. During manufacture, the medical textile 100 can incorporate a longitudinal marker 110 as an additional textile thread during the manufacturing processes (i.e., during weaving, non-weaving assembly, knitting, braiding, laser welding, embossing, other manufacturing techniques, etc.), and the various circumferential markers 120 and 130 can be added to the medical textile after the medical textile is "opened" to a 3-dimensional state, with the longitudinal marker 110 optionally utilized to align the medical textile (i.e., using a mandrel and/or other alignment techniques) to assist with further marking.

In various embodiments, medical textiles were marked using a support mandrel, but in many embodiments a mandrel may not be required for the disclosed markings technologies to properly function. For example, flat fabrics might be marked without using a mandrel or similar holder. With regards to UV laser marking, the marking laser could comprise one or more individual laser beams that originate from a single laser light generator and/or a fixed point, with the one or more laser beams being reflected and/or otherwise angled as the marking works around the part to be marked. In one exemplary embodiment the wavelength of the UV laser can be at or near 355 nanometer, with textile exposure times of fractions of a second.

In various embodiments, an indicator or other marking could comprise a straight line, a non-straight line, a line or figure at virtually any angle for the weave angle and/or from an edge of the textile or implant (i.e., 90 degrees from end of device, 45 degrees, 30 degrees, etc.), a dashed line or solid line, a shape, including geometric shapes (i.e., dot, square, circle, triangle, star, others), patterns of shapes, patterns of dots and/or markings, a rounded, sharp or blurred line, a thick or thin line, one or multiple lines, any combination thereof, and/or other markings. For a non-limiting example, patterns of dots for placement of suture holes.

Figure 4A:
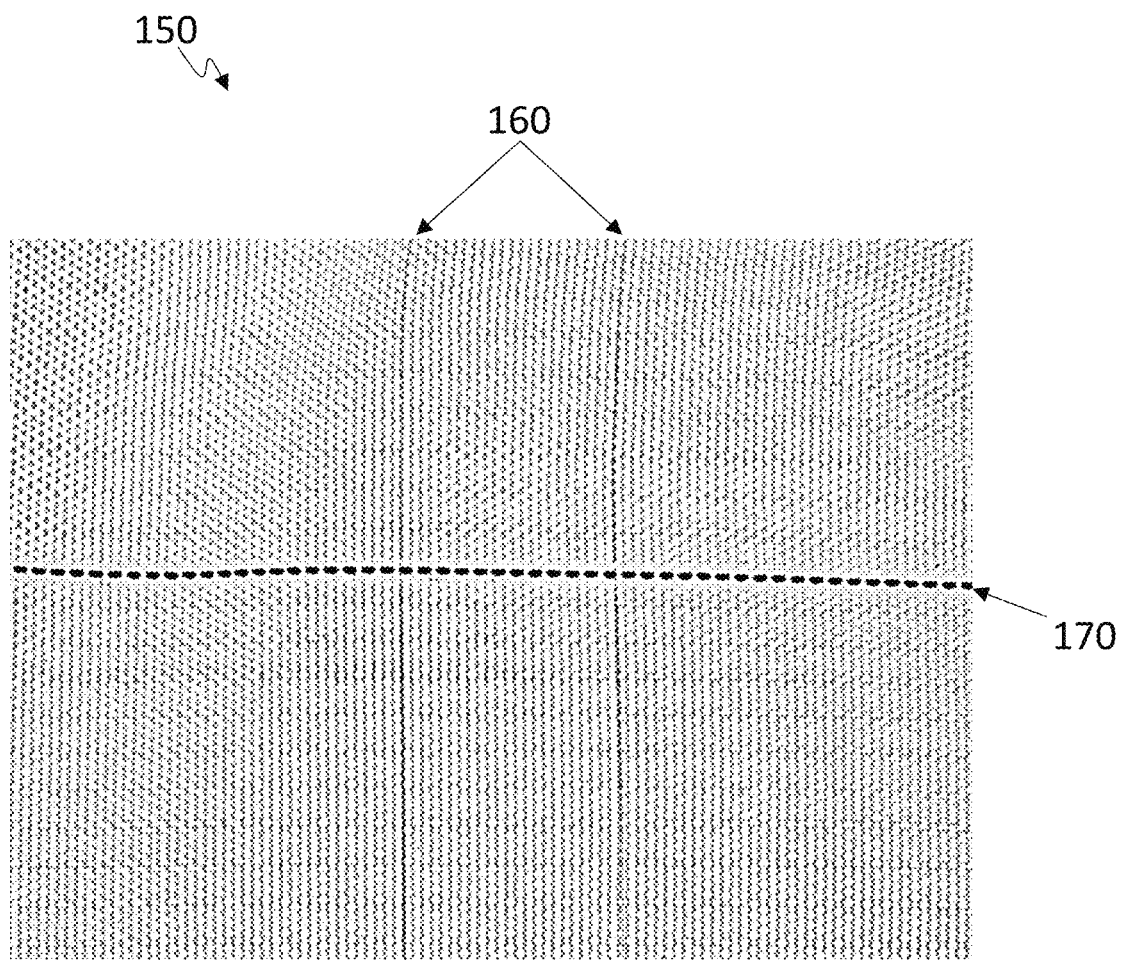
FIGS. 4A-4D depicts a front view of one embodiment of a medical textile with UV marking indicator(s)

FIG. 4A depicts a medical textile comprising polyester Terephthalate (PET) 150 incorporating two UV laser marker lines 160. Using a UV laser to mark medical textiles is advantageous. UV light is absorbed more strongly than longer wavelengths by most materials. Moreover, the laser photons directly break interatomic bonds within the materials causing a cold, photochemical interaction with any fillers or pigments, thus eliminating any heat affected zone (HAZ) or changes to the surrounding material. This produces highly legible mark within the material, rather than at the surface. the higher absorption in the UV means that material can be processed with lower laser power (or pulse energy). Finally, since UV light can be more tightly focused than IR, ultraviolet lasers support complex, high-resolution marks, such as 2D barcodes.

The UV laser marking lines or marking indicator lines 160 that are positioned generally perpendicular to a longitudinal black marker warp yarn 170. The UV laser marking lines or marking indicator lines 160 can be aligned with the weft to ensure the best mechanical performance and integrity of the textile. Accordingly, UV laser marking lines or marking indicator lines 160 can be aligned with the weft does not affect or minimally affects burst strength of the medical textile. In this embodiment, the warp yarn 170 was incorporated into the fabric during initial fabric manufacture, with the laser lines added the finished fabric after manufacture.

While many of the embodiments disclosed herein describe marking techniques on PET and UHMWPE fabrics, it should be understood that the same and/or similar marking techniques and/or technique combinations could be performed on a variety of medical materials and/or fabrics, including high strength and/or enhanced thermal medical fabrics comprising polyethylene terephthalate (PET), or aliphatic polyesters, aromatic polyesters, semi aromatic polyesters, polyurethane, polycarbonates ("PC"), ABS, polypropylene ("PP"), polystyrene, polyethylene ("PE"), polyester, polyacetyl, elastomers, thermoplastic polyurethane ("TPU"), nylon, ionomers, polyvinyl chloride ("PVC"), polytetrafluoroethylene (PTFE), expanded polytetrafluoroethylene (ePTFE), and/or other medical grade materials known by those of ordinary skill in the textile art.

Figure 4B:
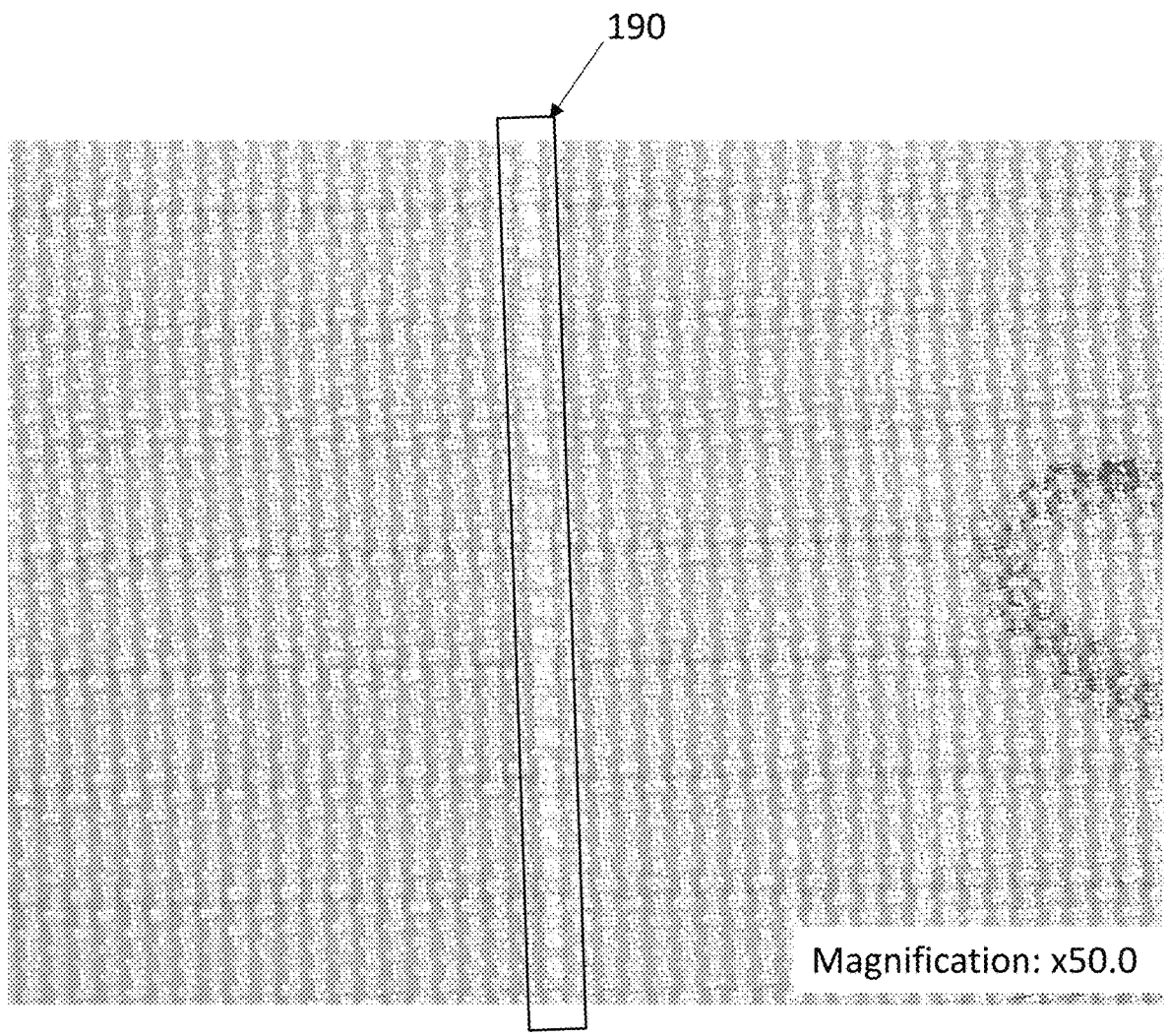
Figure 4C:
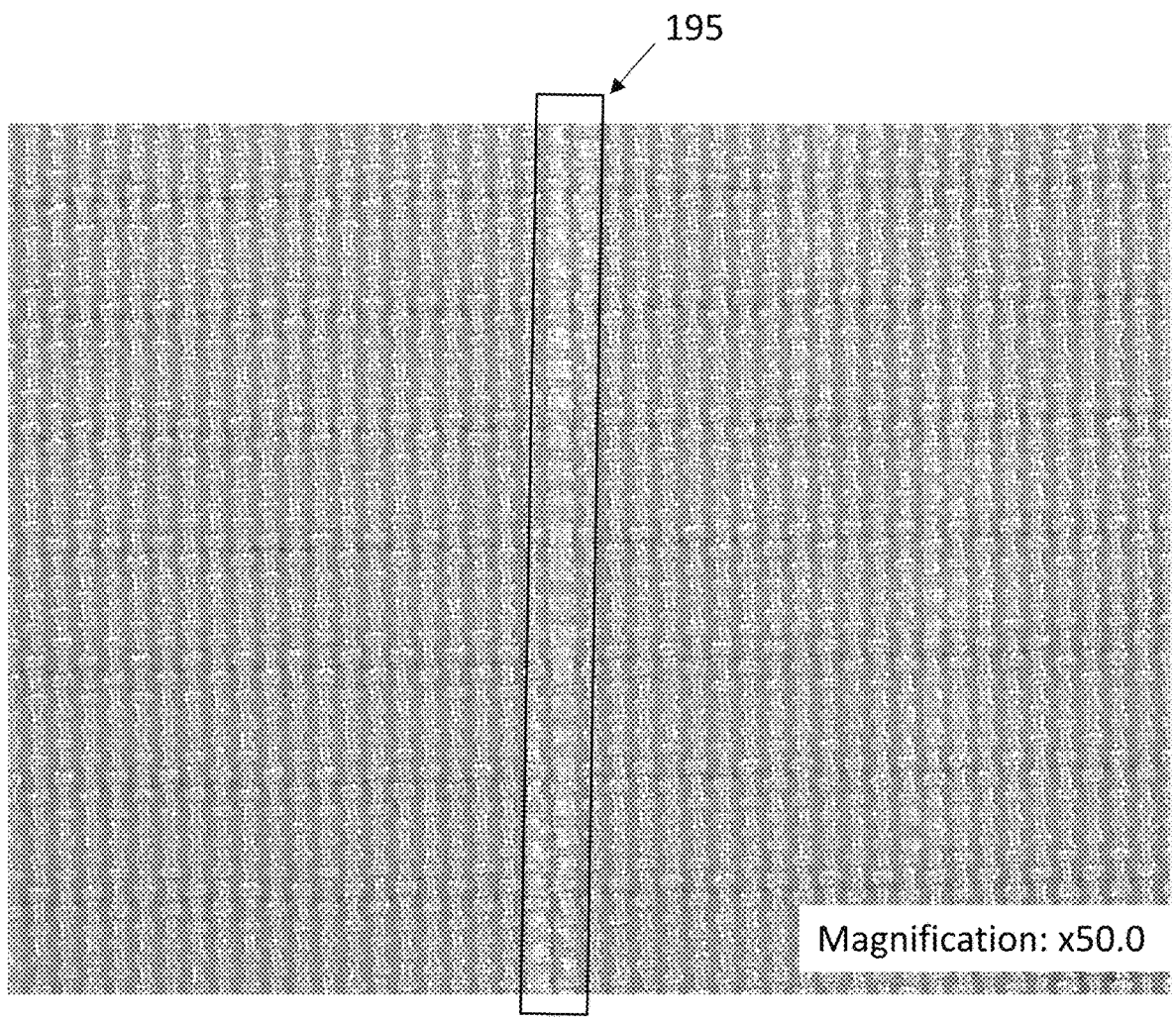
Figure 4D:
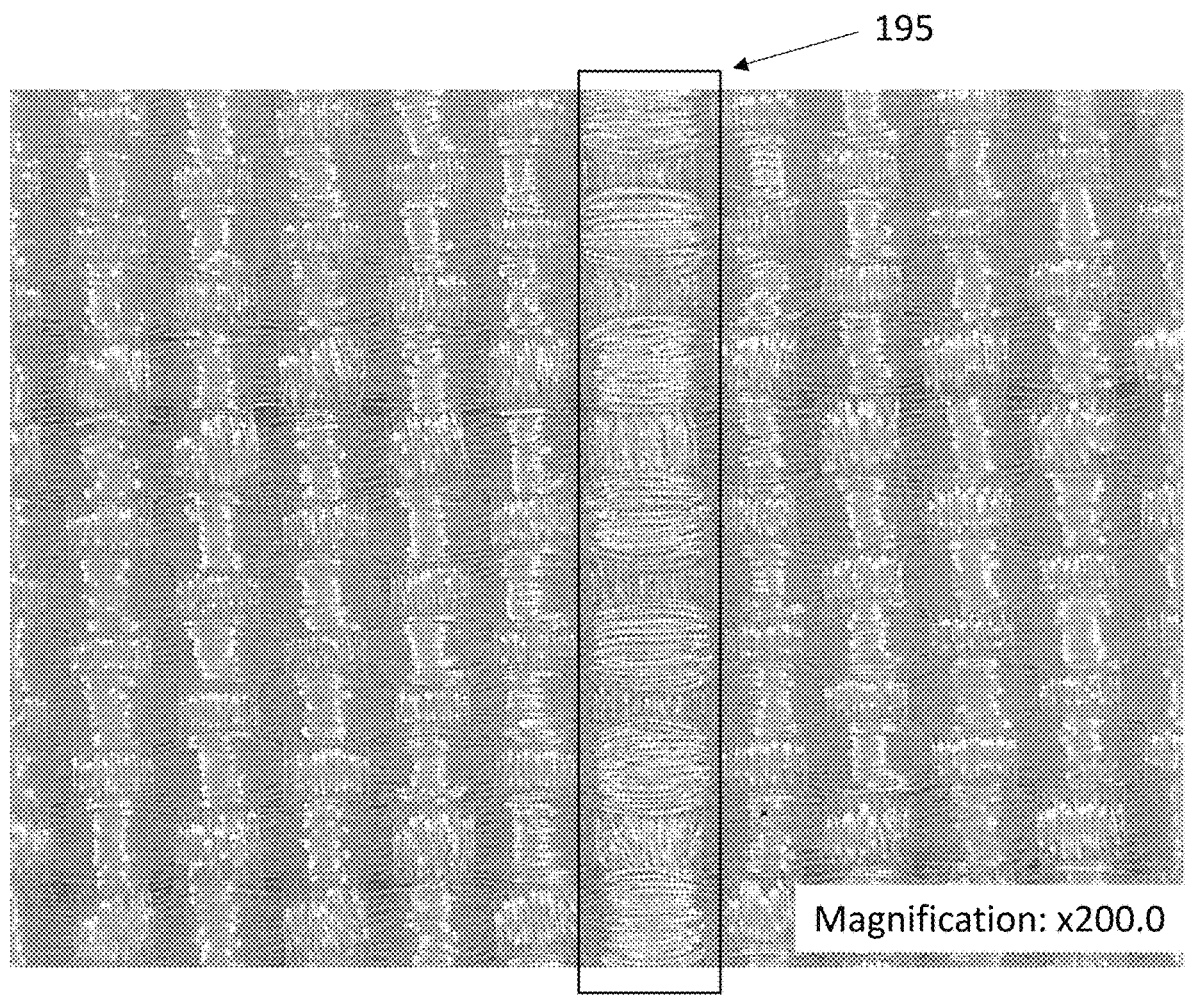

FIGS. 4B through 4D depict another Polyester Terephthalate (PET) textile incorporating a single ultrasonic (US) marker line 190. The marker is easily visible on the front side of the fabric, as shown in FIG. 4B, and can also been easily seen on a back side of the fabric, as shown in FIG. 4C, which both FIGS. 4B and 4C are 50× magnification. FIG. 4D depicts the back side of the fabric of FIG. 4C at 200× magnification, where a slight bulging of the fabric in the marked location can be seen, but with little to no alteration of the mechanical strength of the fabric (i.e. no broken, cut or compromised filaments, fibers or yarns). In still other embodiments, an extremely thin fabric or film may be marked using various of the techniques described herein.

In various embodiments, the marked textile could comprise a fabric having a thickness of approximately 0.12 mm, although a variety of fabric thicknesses could be utilized depending upon the material selection and/or medical application. In various embodiments, a fabric having a thickness of from 0.05 mm to 0.244 mm may be desirable, while in other embodiments a fabric having a thickness of from 0.01 mm to 0.6 mm may be more desirable, while in still other embodiments a fabric having a thickness of from 25 microns to 1 inch may be suitable for various of the marking methods described herein.

Figure 5A:
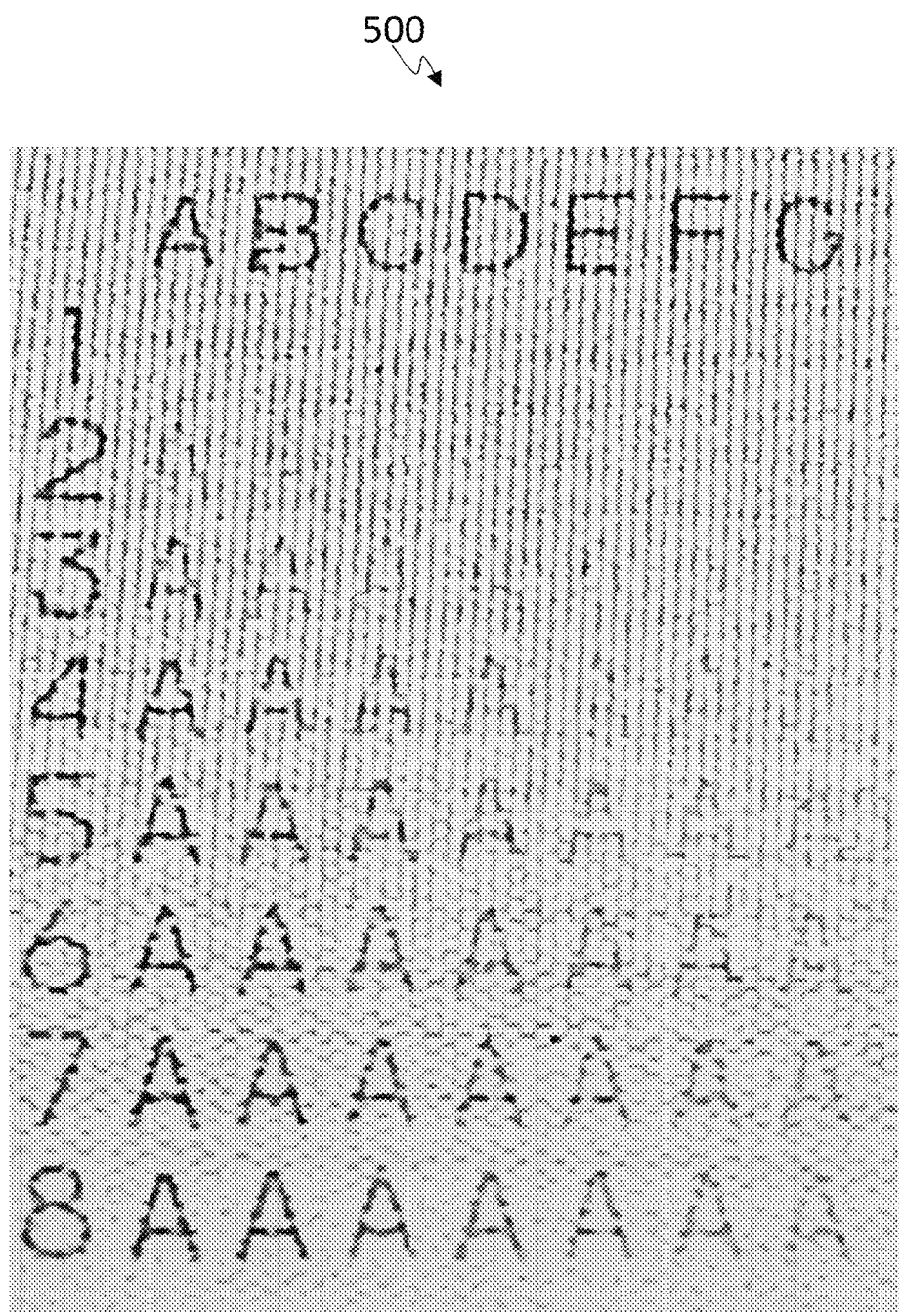

FIG. 5A depicts a marking grid 500 with various markings created on a thin polyester PET fabric 210 utilizing an ultra-violet (UV) laser for marking the fabric at various combinations of different laser power settings ("1"—10% power to "8"—80% power) and different speed settings ("A" at a slowest speed of 2000 mm/sec up to "G" at a fastest speed of 4000 mm/sec), with a pulse frequency of 40 kHz and Spot Variable of −40. In this embodiment, the position 1G on the grid represents the lowest power laser at the fastest transit speed along the fabric, while position 8A represents the highest power laser at the slowest transit speed along the fabric.

FIG. 5B provides a tabular assessment 502 of the various markings of FIG. 5A relative to mechanical performance and integrity. The marking lines or marking indicator lines were assessed based on visibility and/or potential damage to the strength, flexibility and/or durability of the marked textile. The darkest regions in this table (i.e., areas such as 5A, 8A, 8C and similar shaded regions) were assessed as having physical damage to the underlying textile fibers under 60× magnification, but the physical damage did not significantly affect the mechanical performance—the mechanical performance is within manufacturer's or customer's specifications. The lightly shaded regions in this table (i.e., areas such as 3A, 4A, 8E, 8F and similar shaded regions) were assessed as having little to no apparent physical damage under 60× magnification but were likely to have significant damage and/or disruption of the fibers on a molecular level. The unshaded regions in this table (i.e., areas such as 2A, 4C, 8F, 8G and similar unshaded regions) were assessed as having little to no physical damage to the underlying textile fibers under 60× magnification, and little to no damage and/or disruption of the fibers on a molecular level. Where an individual unshaded region included a reasonably visible marker, that region was deemed to be a desirable setting for marking of the given textile—in this instance regions 4C and 8F were identified as desirable (depicted as "X" in FIG. 5B). However, any of the UV settings may be desirable once the yarn and/or the medical textile is modified and/or adapted to achieve the least amount of physical damage that would preserve the expected mechanical performance.

Figure 6A:
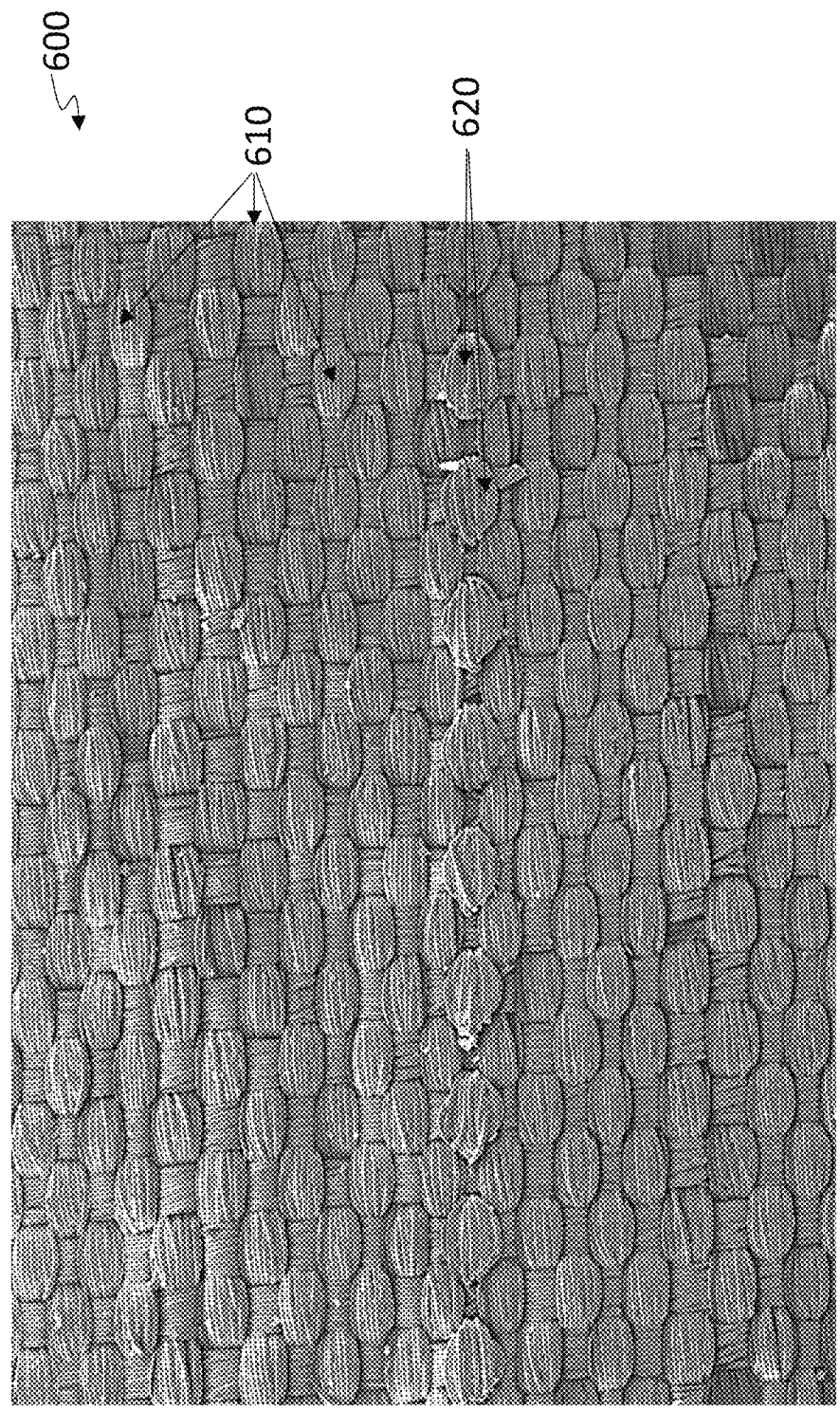
FIGS. 6A-6B depicts magnified views of a medical textile with UV marking indicator(s)
Figure 6B:
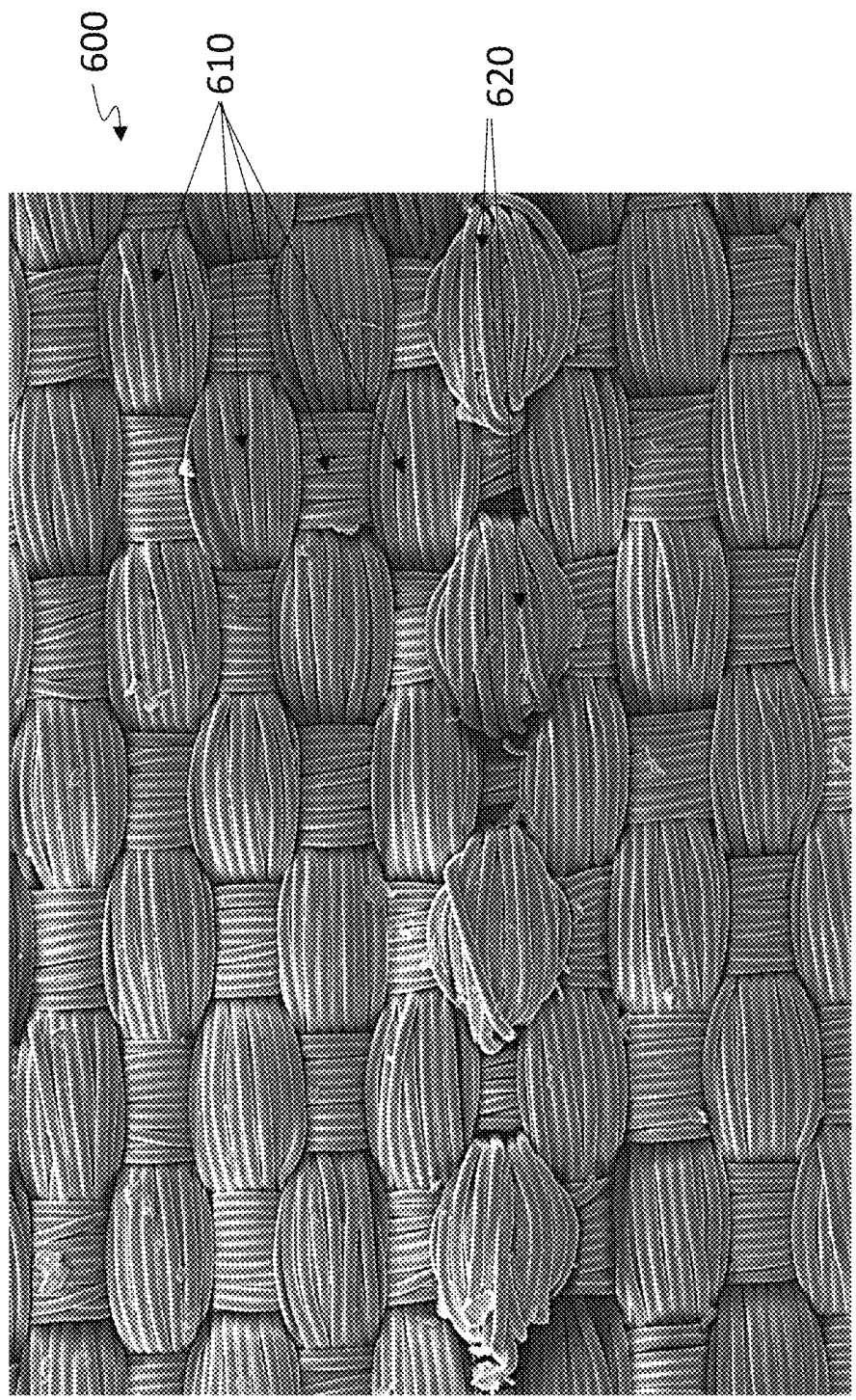

FIG. 6A depicts a scanning electronic microscope (SEM) image of an unmarked portion of one embodiment of a PET) textile 600 at 40× magnification. In this embodiment, vertical and horizontal interwoven PET threads 610 are shown, with warp yarns positioned in the horizontal direction. A single thread of black marker warp yarn 620 (which can be seen is slightly raised from the remaining threads) is shown interwoven horizontally into the textile 600. FIG. 6B depicts a scanning electronic microscope (SEM) image of the unmarked portion of the PET textile 600 at 100× magnification, showing the vertical and horizontal interwoven PET threads and the single raised thread of black marker warp yarn 620. The black mark warp yarn 620 may be raised relative to unmarked areas of the medical textile. Alternatively, the black mark warp yarn 620 may be equal height relative to unmarked areas of the medical textile. In addition, the black mark warp yarn 620 may be below the height of the unmarked areas of the medical textile.

Figure 7A:
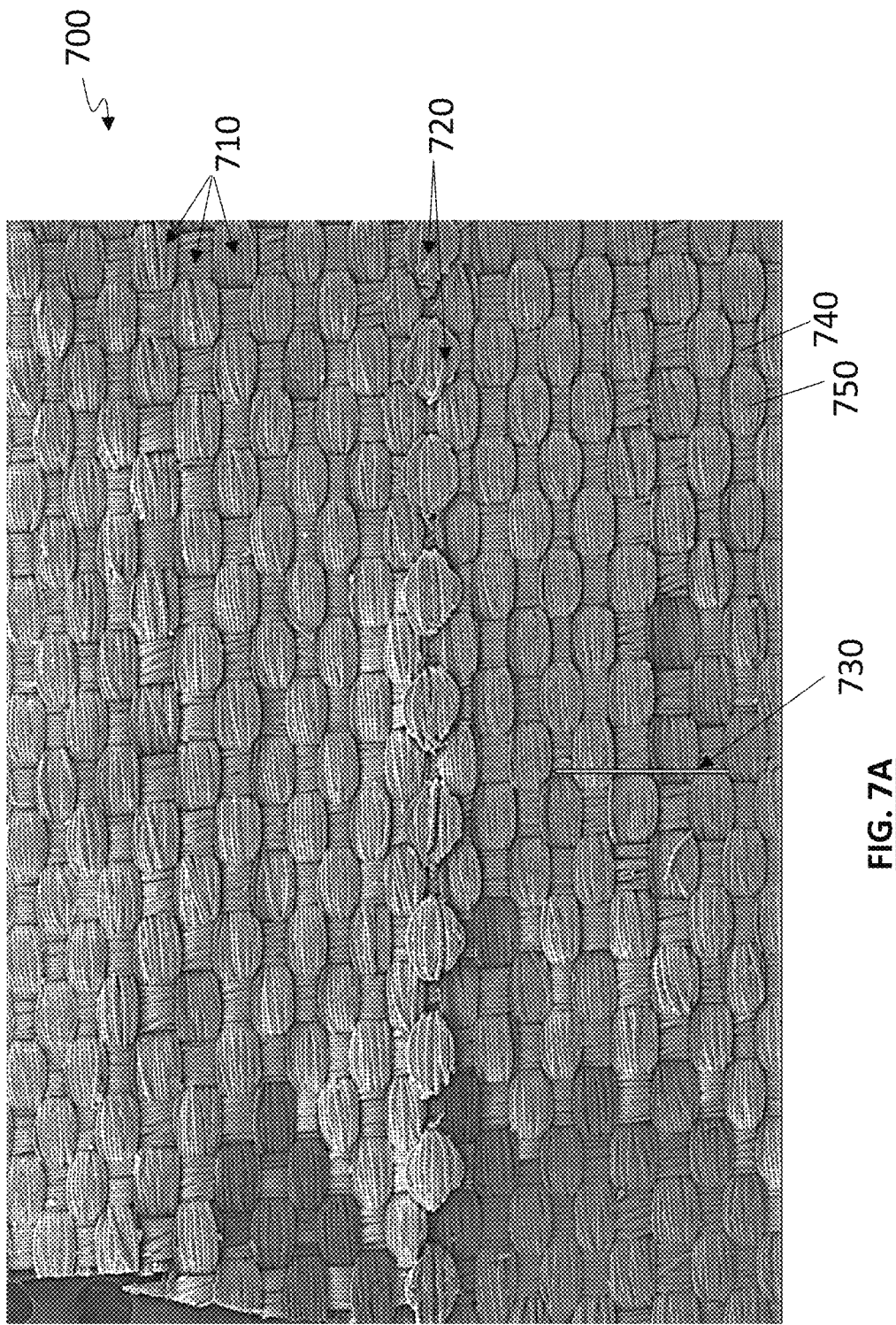
FIGS. 7A-7B depicts magnified views of an alternate embodiment of a medical textile with UV marking indicator(s)
Figure 7B:
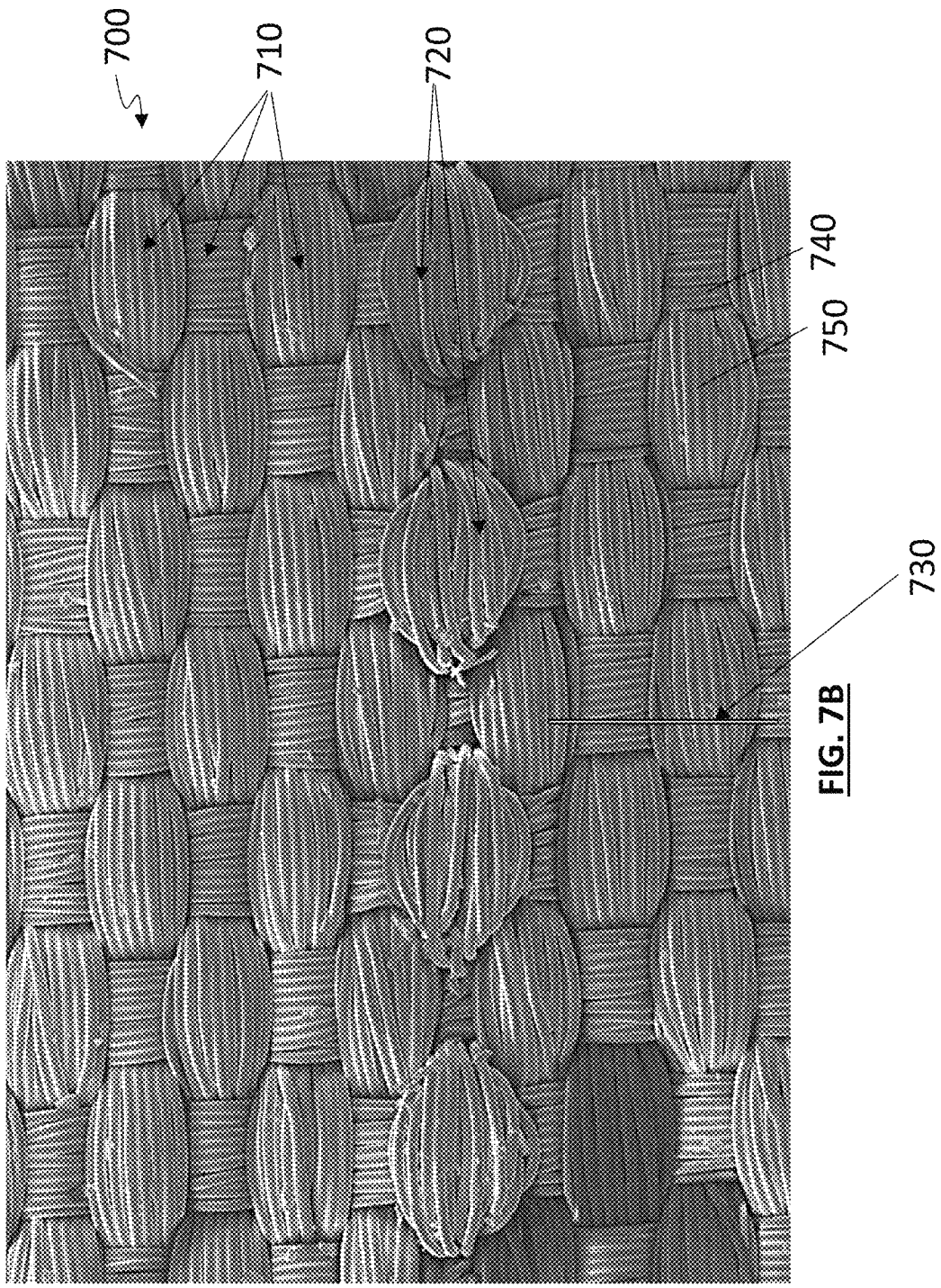

FIGS. 7A and 7B depict SEM images of a marked portion using at least two marking techniques onto one embodiment of a PET textile 700, at 40× and 100× magnification, respectively. The two techniques may comprise black marker warp yarn and/or UV laser marking. In this embodiment, a woven medical textile comprising a vertical and horizontal interwoven PET threads 710 are shown, with warp yarns positioned in the horizontal direction 750, the weft yarns positioned in the longitudinal or axial direction 740 and a single thread of black marker warp yarn 720 (which can be seen is slightly raised from the remaining threads) is shown interwoven horizontally into the textile 700. In this embodiment, the Power/Speed settings for the UV marking laser were set at 4C (see FIGS. 5A and 5B), with a UV marking indicator 730 that aligns with the weft yarn 740. The UV marking indicator 730 is raised relative to the unmarked portion of the PET textile 700. Accordingly, the UV marking indicators can be parallel to the direction of the weft yarn 740 to preserve mechanical performance and/or integrity of the medical textile. As can be seen from these FIGS. 7A-7B, no damage to the fibers of the marker yarn was apparent. The UV marking indicators may be raised relative to unmarked areas of the medical textile. Alternatively, the UV marking indicators may be equal height relative to unmarked areas of the medical textile. In addition, the UV marking indicators may be below the height of the unmarked areas of the medical textile.

Figure 8:
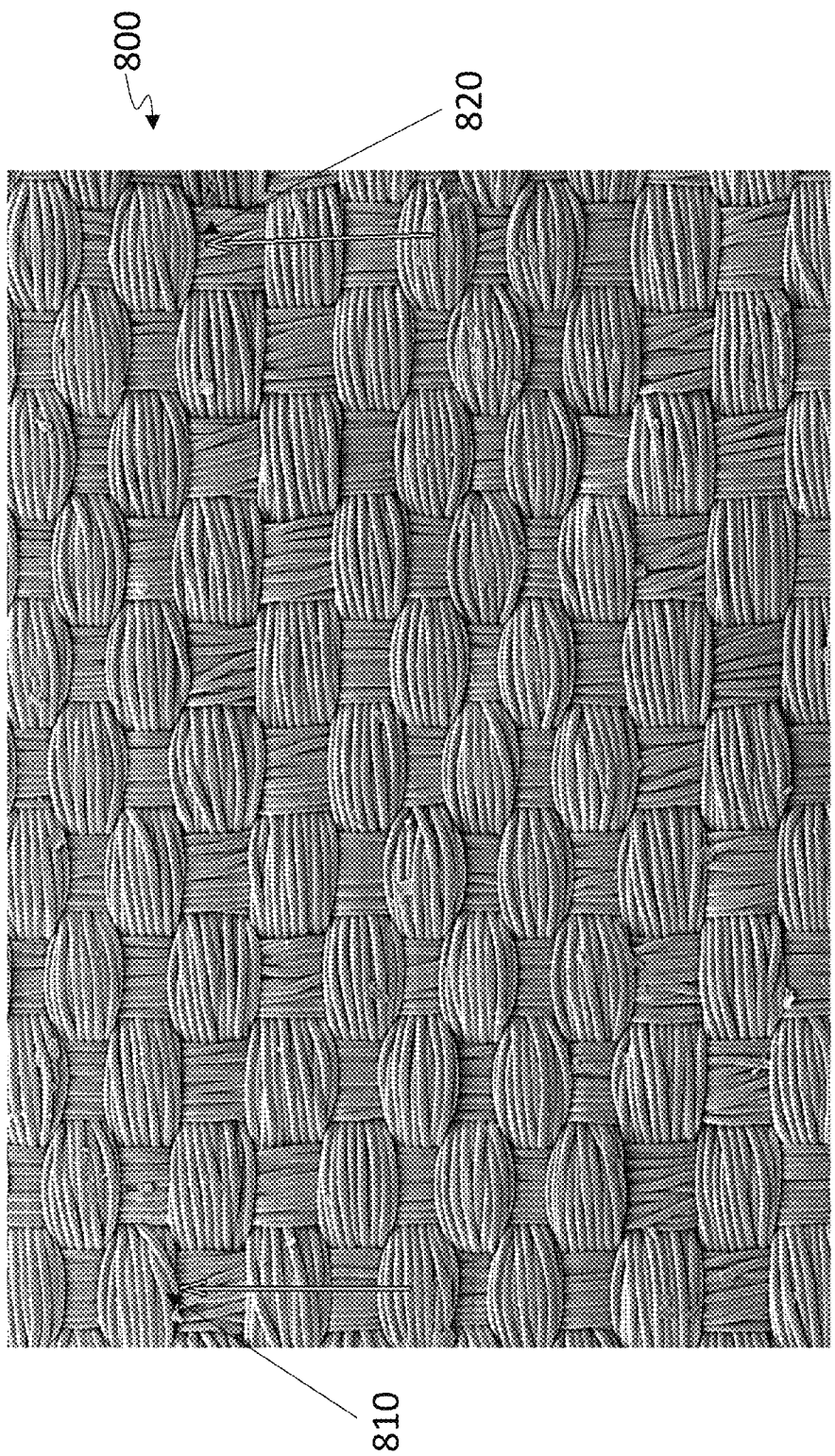
FIG. 8 depicts magnified view of a medical textile with UV marking indicator(s)

FIG. 8 depicts an SEM image of a medical textile 800 comprising UV marking indicators 810, 820. The SEM image is at 70× magnification and the UV marking indicators 810, 820 were created using different settings (see marking grid 200 of FIG. 5A). In this embodiment, the UV power settings comprise marking grid locations 8D and 8E are depicted as arrow locations 810 and 820, respectively. Neither of these locations depicts any apparent gross physical damage at this magnification.

Figure 9:
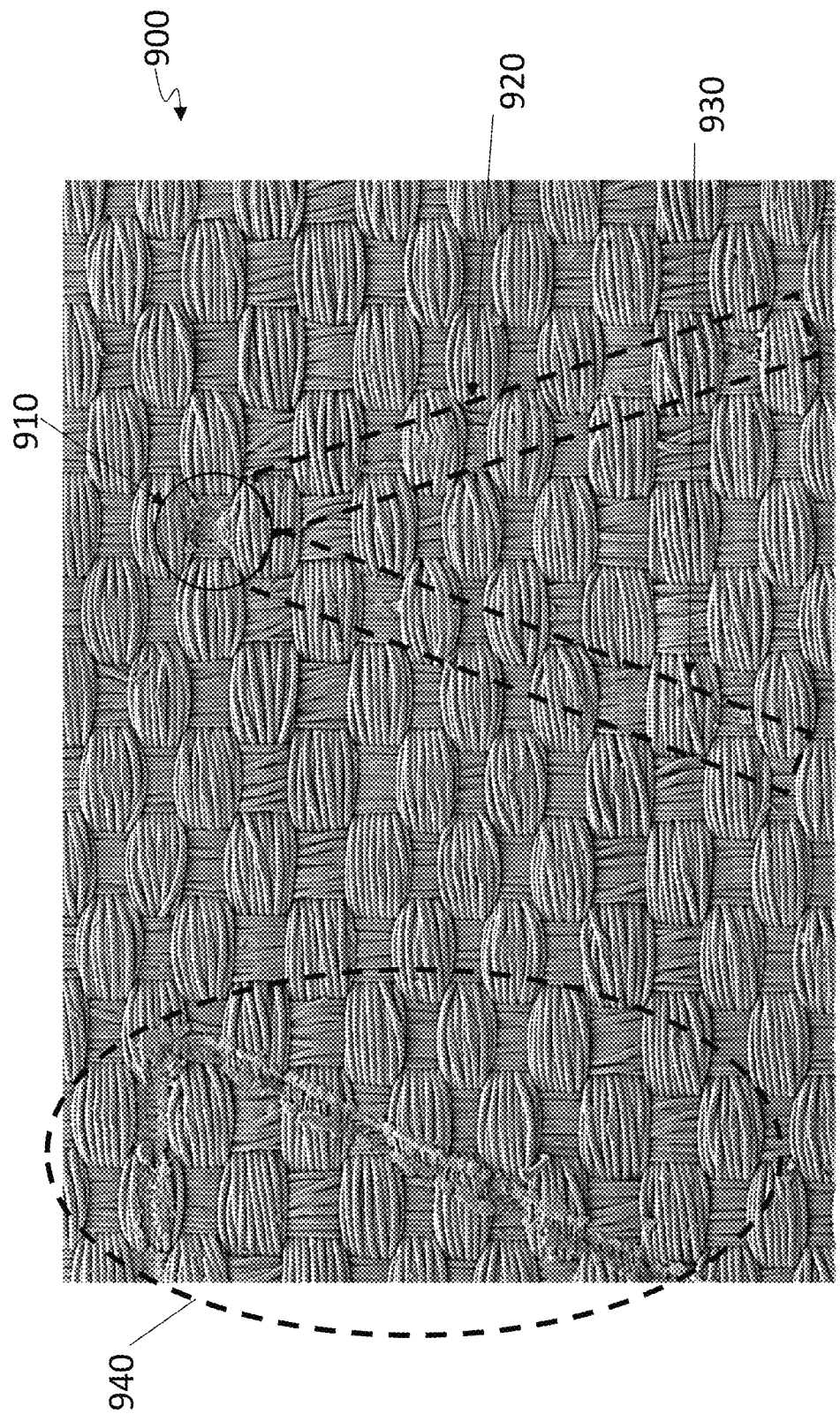
FIG. 9 depicts magnified views of a medical textile with UV marking indicator(s)

FIG. 9 depicts a medical textile 900 comprising UV marking indicators 910, 920, 930, 940. This figure is an SEM image of the medical textile 900 at 60× magnification using different UV settings (see marking grid 200 of FIG. 5A). In this embodiment, the top of the "A" uses UV settings comprising a grid location 7A (see FIG. 5A) is depicted as circled location 910, with shadow lines 920 and 930 representing the legs of the "A" extending downward and to each side of location 910. In addition, a portion of the UV laser etched marking indicator 940 of a "7" that was created using UV laser setting 7A as shown in the UV settings marking grid 200 of FIGS. 5A-5B. While these have little gross physical damage along the shadow lines 920 and 930, the location 910 has significantly damage, most likely from an undesirable amount of laser dwell time at the apex point of the figure "A". At the apex point, the UV marking indicator has a plurality of overlapping UV beams that may affect the overall mechanical performance. However, the medical textile structure and/or the material properties may be optimized or modified to preserve the mechanical performance of marked medical textile relative to an unmarked medical textile. Such modification and/or optimization may eliminate or reduce any damage caused by overlapping of UV beams.

Figure 10A:
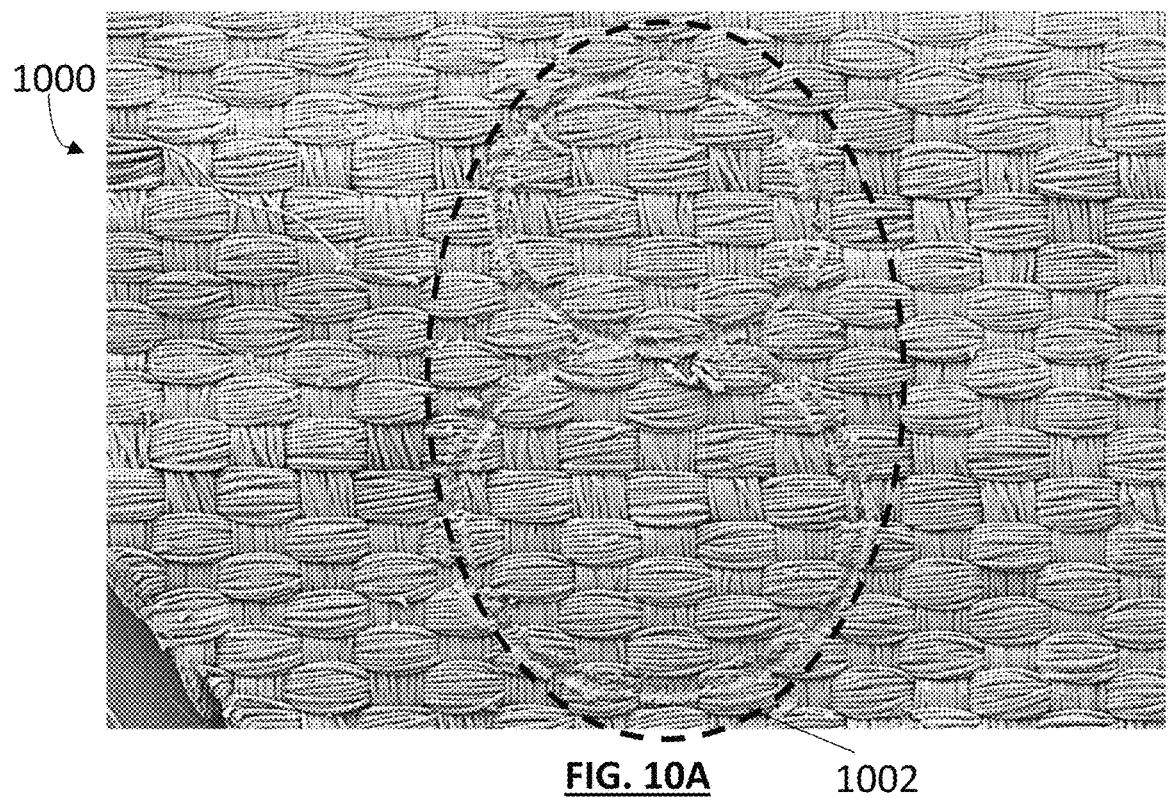
FIGS. 10A-10E depicts magnified views of an alternate embodiment of a medical textile with UV marking indicator(s)
Figure 10B:
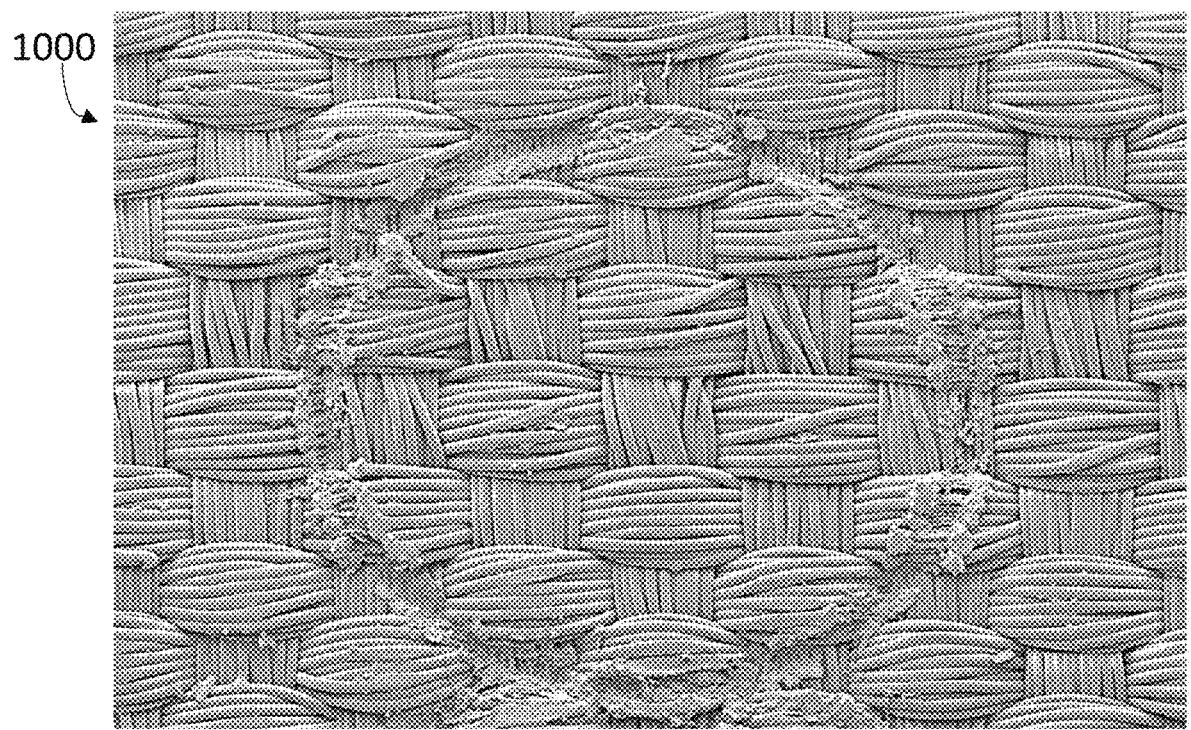

FIG. 10A depicts a SEM image of a medical textile 1000 at 50× magnification comprising UV laser marking indicators 1002 using different UV laser settings. The UV laser settings correspond to the lower left portion of the marking grid 200 of FIG. 5A—representing the highest laser power and slower transit time in the current test series. In this embodiment, a UV laser was used to mark a circle, non-straight line, on PET. As can be seen from FIG. 10A-10B, many of the fibers and/or threads of the fabric have been moved, melted, cut, burned and/or otherwise disrupted by the marking laser, including the ejection of significant amounts of material from the marked locations that have redeposited on other portions of the fabric. An extra magnified view at 100× magnification of an upper portion of this figure "8" is depicted in FIG. 10B, which shows additional melt and reconsolidation areas at the edges of the laser marks in the fibers of the textile material.

Figure 10C:
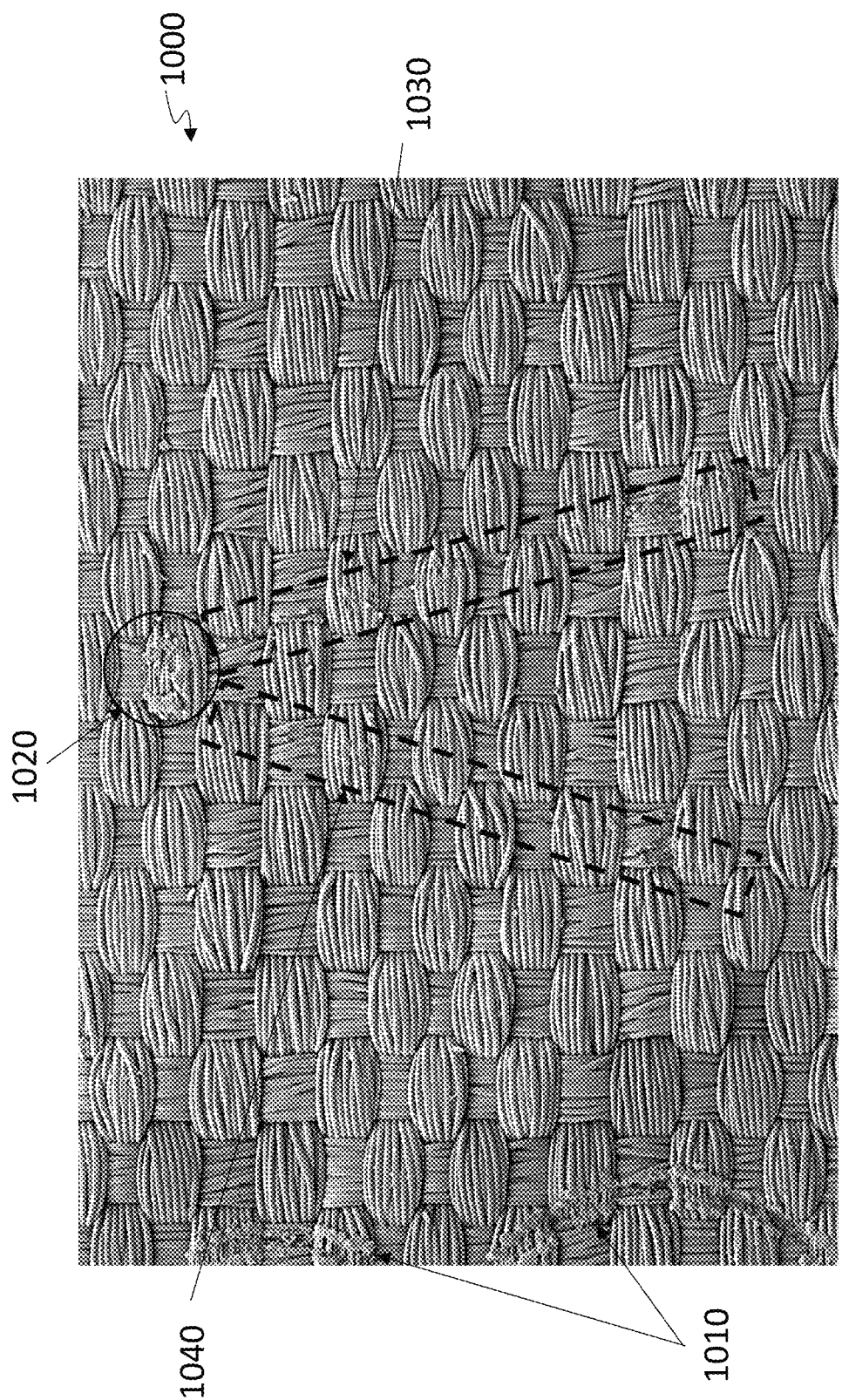
Figure 10D:
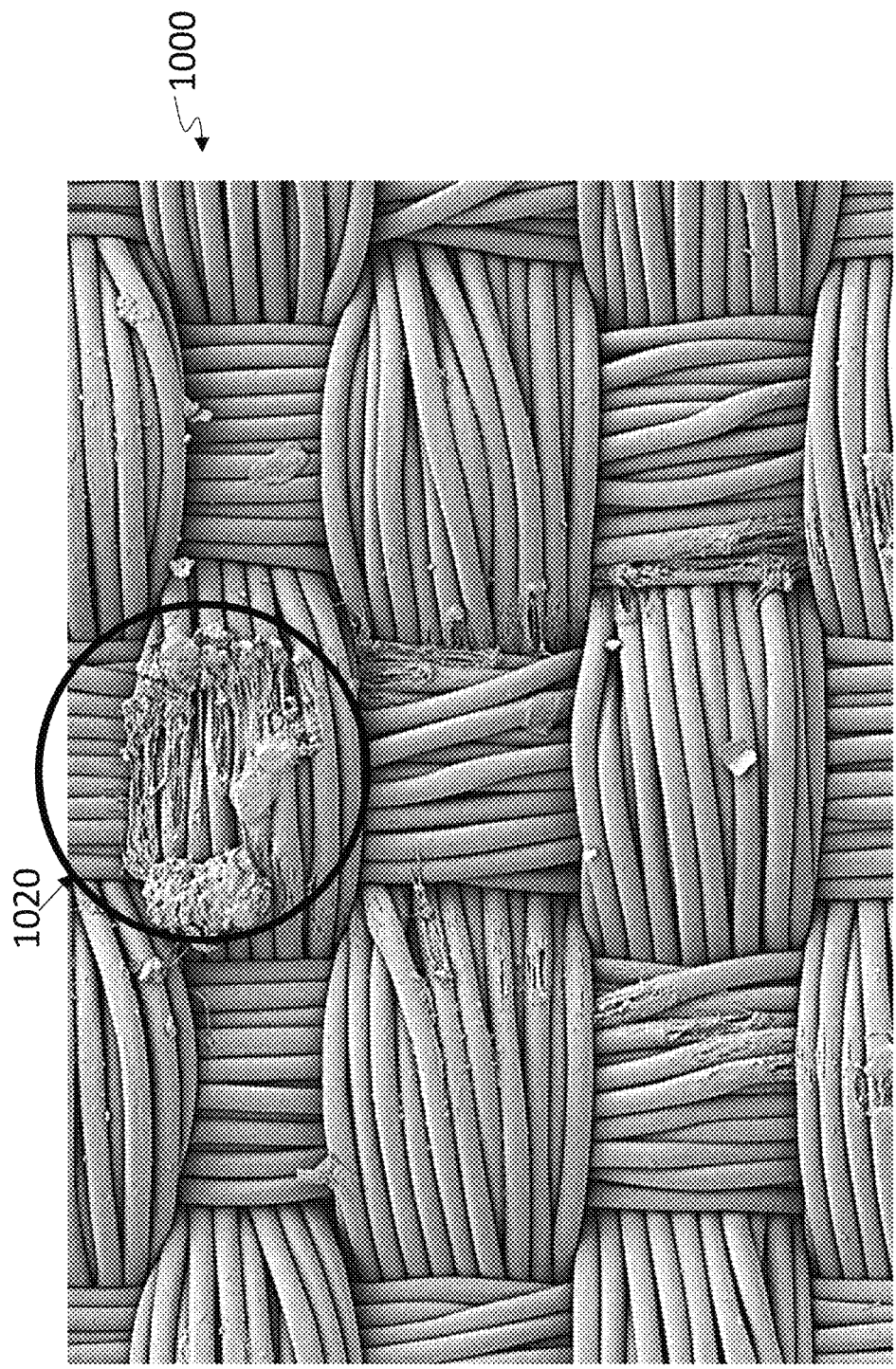

FIG. 10C depicts a SEM image of a different region of the medical textile 1000 comprising UV laser marking with different UV laser settings at 60× magnification. The UV laser settings comprises a grid location 8A of the marking grid 200 of FIG. 5A. A portion 1010 of the laser etched "8" from the grid index can be seen at the left of the picture. In addition, the top of the "A" using UV laser settings comprising a grid location 8A is depicted as circled location 1020, with shadow lines 1030 and 1040 representing the legs of the "A" extending downward and to each side of location 1020. Another magnified view at 200× magnification of the location 1020 of this figure "A" is depicted in FIG. 10D, which shows additional melt, cut and reconsolidation areas at the edges of the UV laser marking indicators in the fibers of the textile material.

Figure 10E:
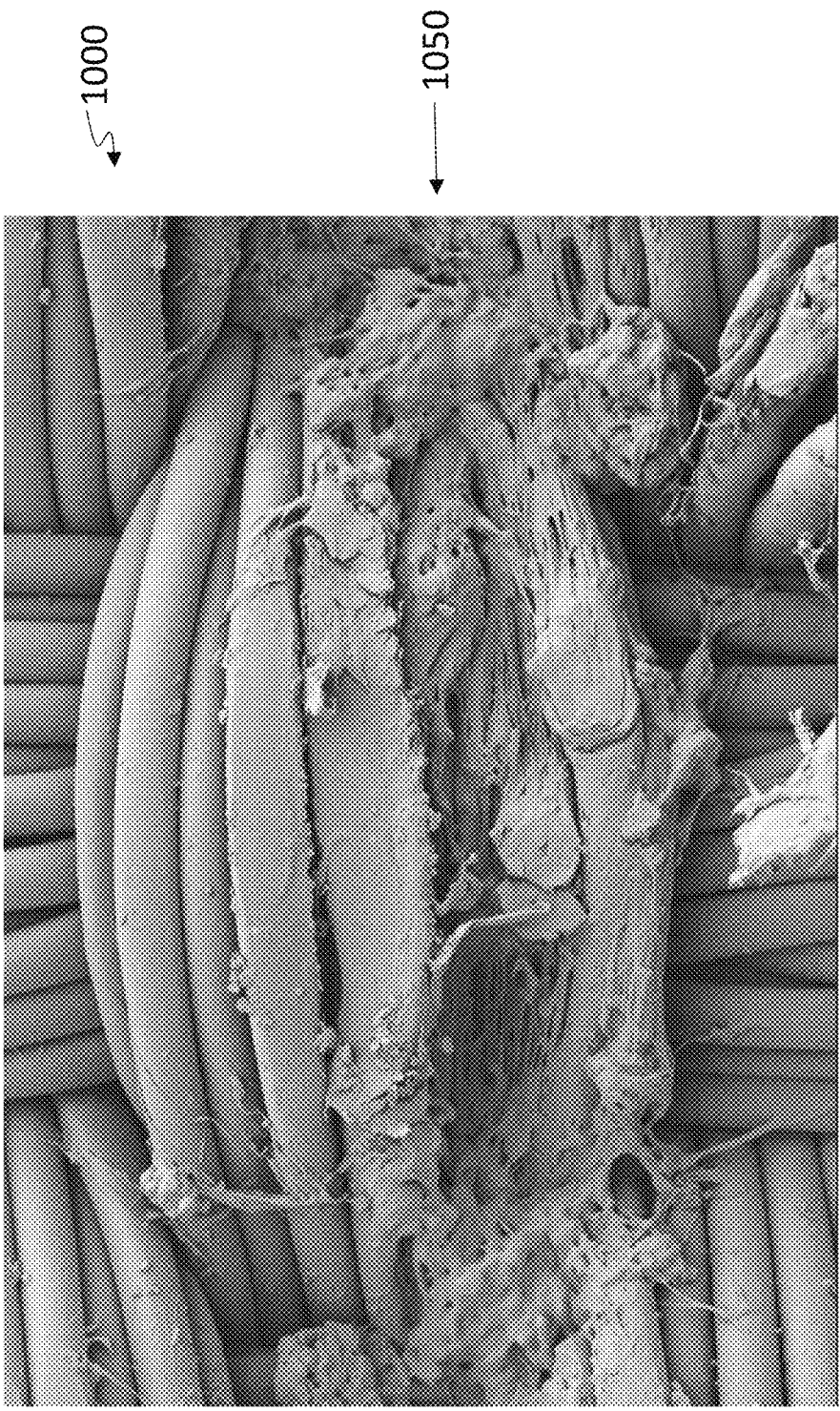

FIG. 10E depicts a central region 1050 of the laser etched "8" from the grid index on the marking grid 200 of FIG. 5A, at 500× magnification. Significant damage to the underlying textile structure is apparent, which may be due to the highest laser setting at the slowest speed, as well as the occurrence of laser marking overlap as each circle of the "8" was marked on the textile. In order to avoid such damage in the future, markings should be planned and executed to avoid laser mark overlap within an individual figure (which would desirably avoid causing the extent of damage shown on this SEM image).

Figure 11:
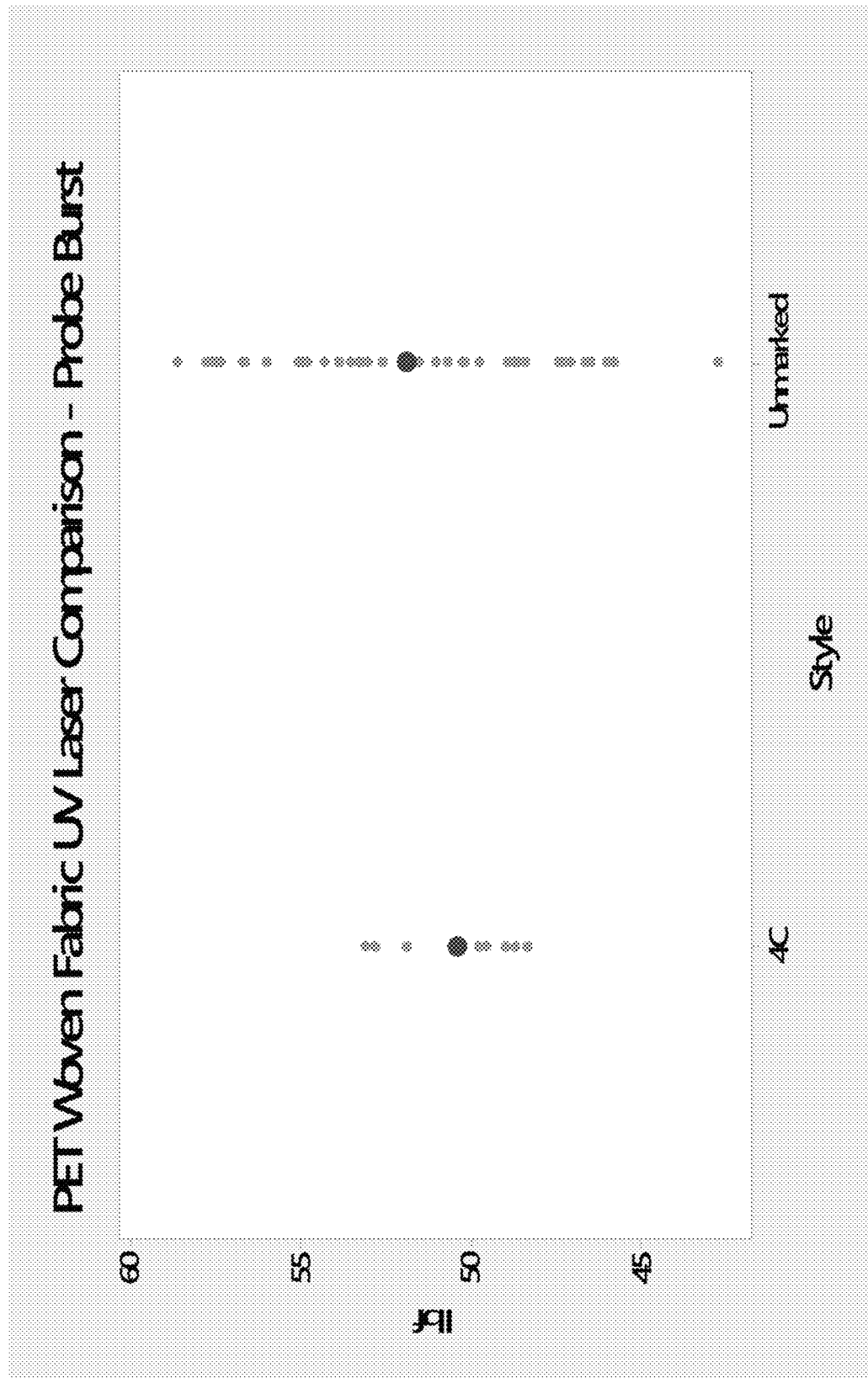
FIG. 11 depicts a graph burst test for a medical textile with UV marking indicator(s)

FIG. 11 depicts a graphical representation of a probe burst test on a medical textile comprising UV laser marking indicators. The probe burst test was conducted per ISO 7198 procedures (International Organization for Standardization procedure 7198—the disclosure of which is incorporated by reference herein). This test involved localized tensile strength testing by pressing a ⅜" probe through the fabric. The medical textile comprising UV laser marking indicators used UV laser settings comprising a grid location of 4C as seen in FIG. 5B. The medical textile included a PET woven textile. The test results showed no practical difference in probe burst strength between unmarked fabrics and marked fabrics (using the "4C" power/speed setting of FIG. 5B), which suggests that the marked graft is not physically compromised or its integrity affected by the presence of UV laser marking to any significant degree.

Figure 12A:
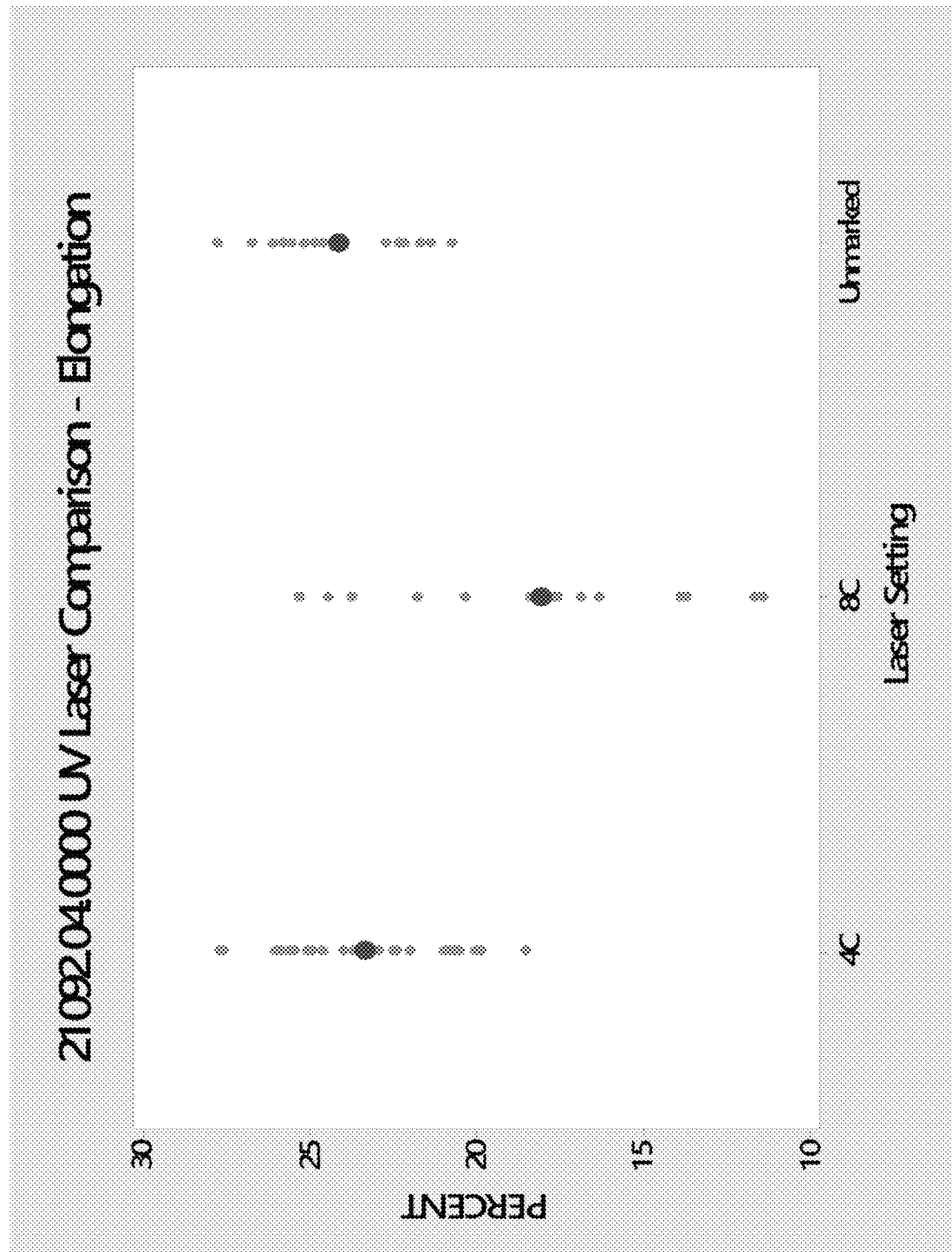
FIGS. 12A-12C depicts various graph mechanical testing for a yarn with UV marking indicator(s)
Figure 12B:
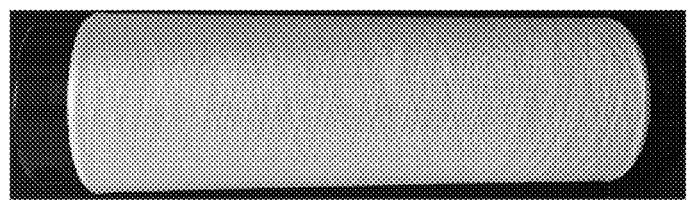

FIG. 12A depicts a graphical representation of elongation testing on a medical yarn comprising UV laser marking indicators. The elongation tests were conducted using ASTM D2256-02 as a reference for procedures (American Society for Testing and Materials procedure D2256-02—the disclosure of which is incorporated by reference herein). The test yarn was PET manufactured at 40 Denier, 27 filaments, textured, 12 twists per inch. The test was performed on yarn that was UV marked while on a spool/bobbin/package such as depicted in FIG. 12B. The elongation test compared medical yarns using UV laser settings comprising grid location 4C and 8C, and unmarked medical yarn. The test results showed that the UV laser substantially degraded the polymer at 8C UV laser settings, but did not degraded the polymer at 4C UV laser settings, which were reflected by the significant drop in elongation for the 8C test specimens.

Figure 12C:
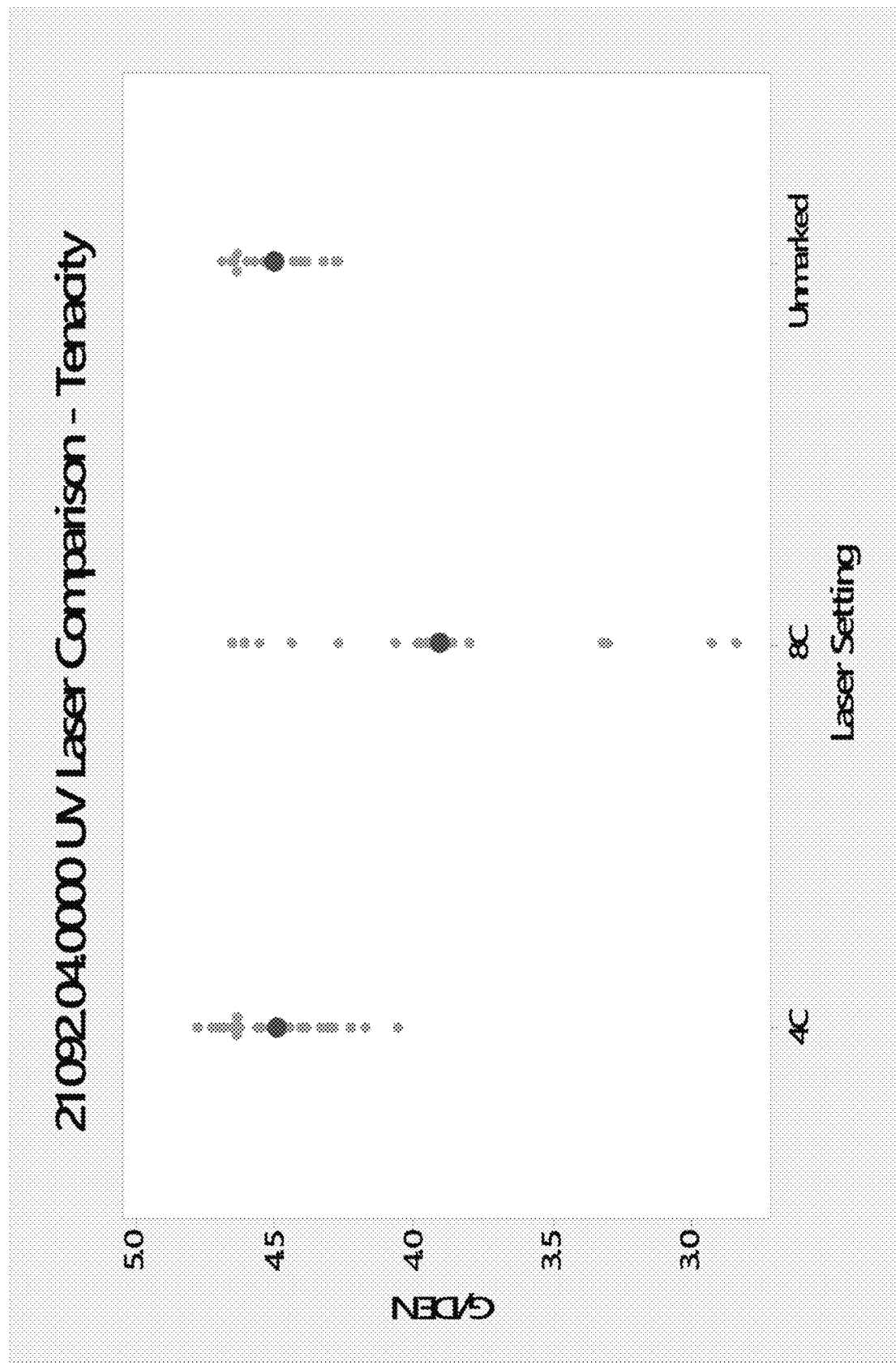

In addition, FIG. 12C depicts a graphical representation of tenacity testing on a medical textile comprising UV laser marking indicators. The tenacity test compares medical textiles using UV laser settings comprising grid location 4C and 8C (see FIG. 5B), and unmarked medical textile. The tenacity test shows that the UV laser degrades the polymer substantially at the 8C settings (~25%), but not at the 4C settings as reflected by the drop in Tenacity as compared to the unmarked medical textiles.

Figures 33A, 33B:
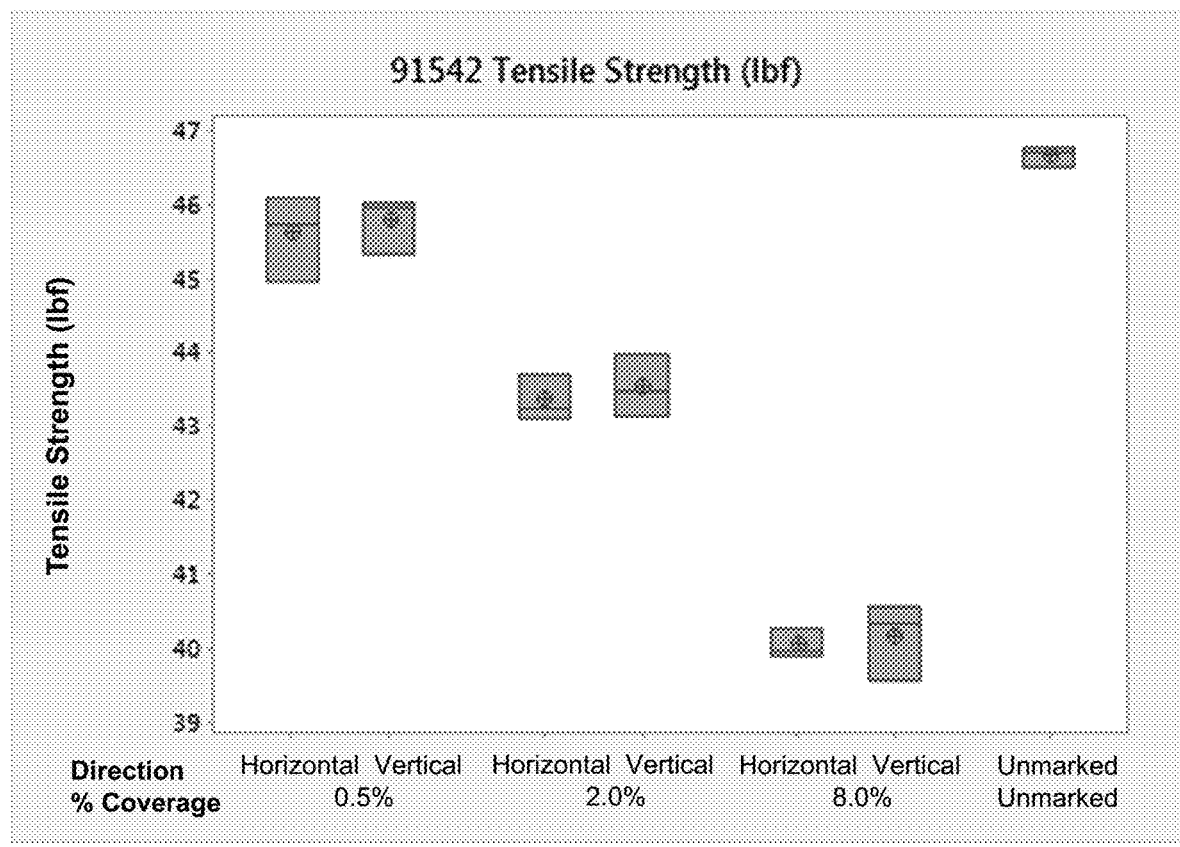
FIGS. 33A-33B depicts a graphical representation of burst strength testing for a braided textile with UV marking indicators.
Figure 33C:
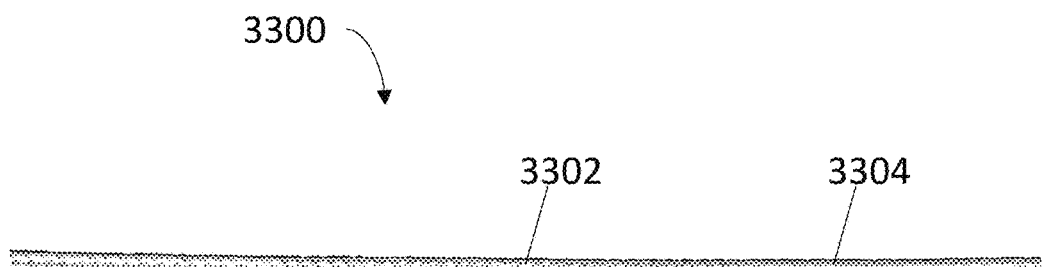
FIGS. 33C-33D depicts a standard and magnified view of one embodiment of a braided textile with UV marking indicators.
Figure 33D:
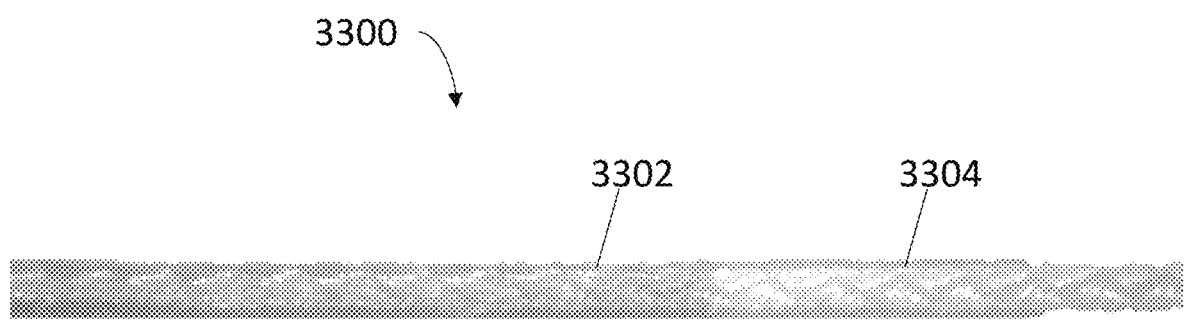

FIGS. 33C-33D depicts a standard and magnified view of a marked medical textile comprising braiding 3300, or known as a marked braided medical textile 3300 using UV laser marking technique. The marked braided textile 3300 comprises a marking indicator 3302 and non-marked portion 3304. The braided medical textile comprises PET having a 1×2 diamond full, 27 pics-per-inch (PPI), the yarn denier is 100 and 3 twists-per-inch (TPI). The UV laser settings were at 3C as depicted within the UV marking grid of FIGS. 5A-5B. The UV laser altered the original color of the material from white to grey, a discoloration, but did not physically degrade the polymer.

FIG. 13 depicts a medical textile 1300 comprising an embossing marking indicator 1310 that can be identified visible and/or tactilely. Embossing is a technique in which images and/or patterns can be created on a surface of a fabric through the application of heat and/or pressure. Desirably, the embossing will create one or more raised and/or lowered surfaces, but without significantly changing the nature of the underlying material on which it is performed. Various embossing techniques may be suitable for a variety of medical textiles and/or marking types, including Blind Emboss (in which the embossed image and the fabric surface image are the same), Tint Emboss (where a pastel foil or pearl may be used), Single-Level Emboss (where a marking may be raised to one flat level), Multi-Level Emboss (where various markings may be raised to different levels, potentially giving a depth to the markings), Printed Emboss (where the embossed part may include a printed image, directions and/or manufacturer's logo on the medical textile), Registered Emboss (where a printed image may be embossed to give a raised look), Glazing (where an embossed marker may be formed to give a shine to the fabric surface), as well as Blind Printing and/or Relief Printing. In various embodiments, embossing techniques may be utilized to desirably raise and/or lower various threads and/or fabric portions of the medical textile.

In various embodiments disclosed herein, the employment of embossing and/or other disclosed techniques for marking a medical textile may be useful for a variety of technical reasons. Unlike traditional embossing of fabrics, which is typically used for decorative and/or aesthetic purposes, the embossing of medical fabrics can include markings and/or other features that would be useful during a variety of processing steps and/or manufacturing operations, such as alignment markings, measurement indicators, folding and/or cutting lines, labels and/or source identifiers, indicators for engineering purposes, safety features and/or use instructions. By minimizing the structural and/or biological impact(s) a given marking technique and/or technique combination has on a medical textile, the disclosed methods and/or techniques can greatly enhance the usability and/or performance of a medical textile and the products manufactured therefrom.

Figure 14A:
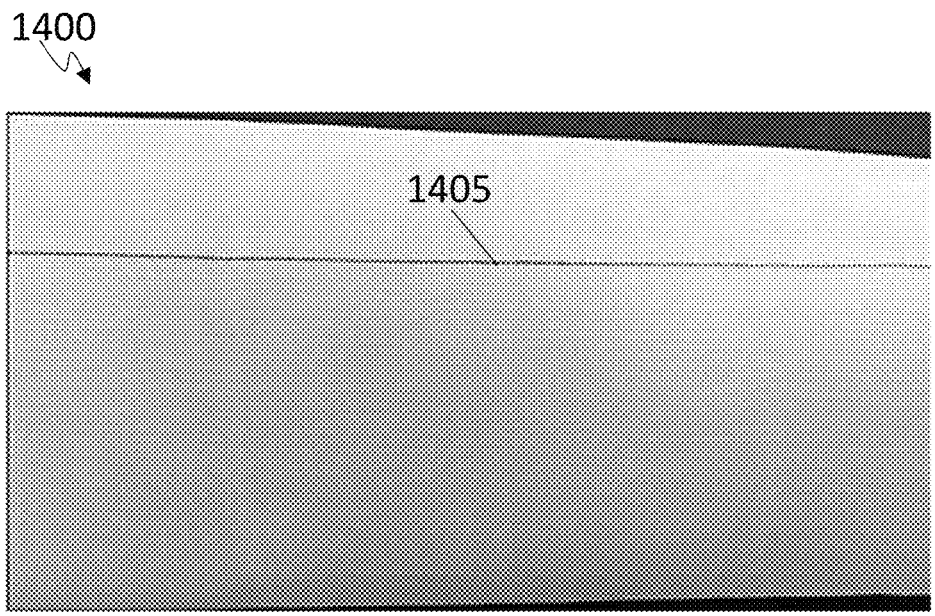
FIGS. 14A-14B depicts magnified view of a medical textile with stamping and crimping marking indicator(s), respectively.
Figure 14B:
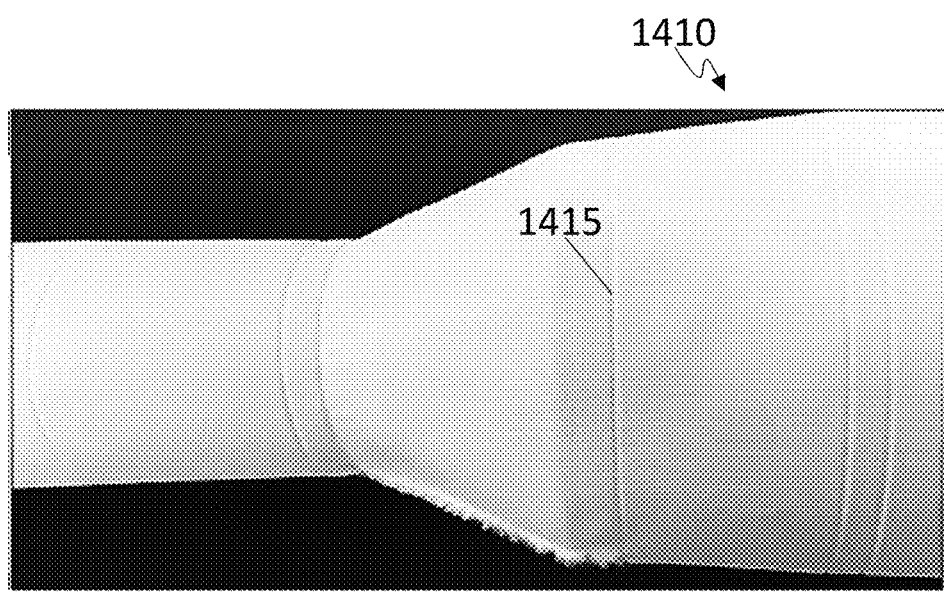

FIGS. 14A and 14B depict a medical textile implant 1400, 1410 with a stamping marking indicator 1405 and a crimping marking indicator 1415 that can similarly be identified visibly and/or tactilely. In this embodiment, a "crimp" in a textile strand can be defined as the undulations or succession of waves or curls in the strand, induced either naturally during fiber growth, mechanically, or chemically. Crimp in a fiber can thus be considered as the degree of deviation from linearity of a non-straight fiber. Fiber crimp can be the waviness of a fiber expressed as waves or crimps per unit length or as a difference between the lengths of the straightened and crimped fiber.

The stamping and/or crimping of the medical textile fabric will desirably create a visibly and/or tactilely identifiable marking and/or other indicator without significantly affecting the structural integrity, flexibility and/or performance of the underlying medical textile material. In addition, the use of these and similar techniques may desirably avoid the inclusion of inks or other materials that may elute from the medical textile and/or require additional biocompatibility testing.

Figure 15:
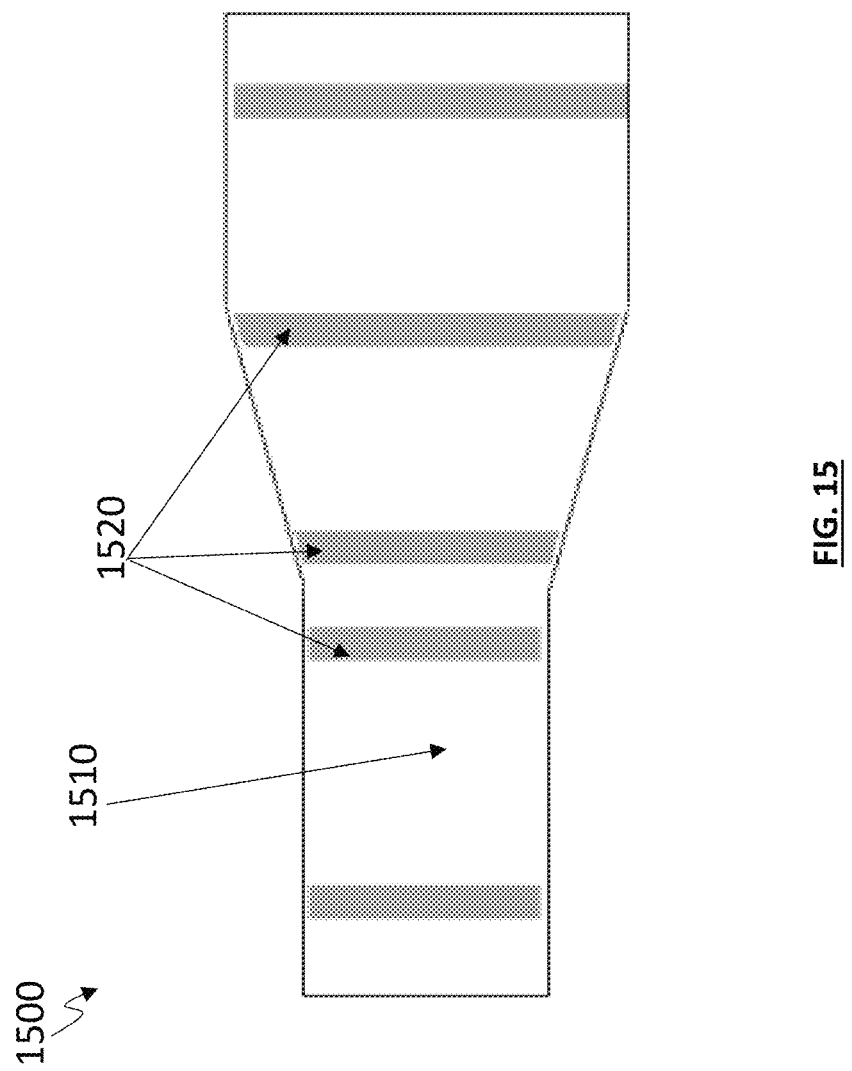
FIG. 15 depicts a magnified view of a medical textile with a colored yarn weave marking indicator(s)
Figure 17C:
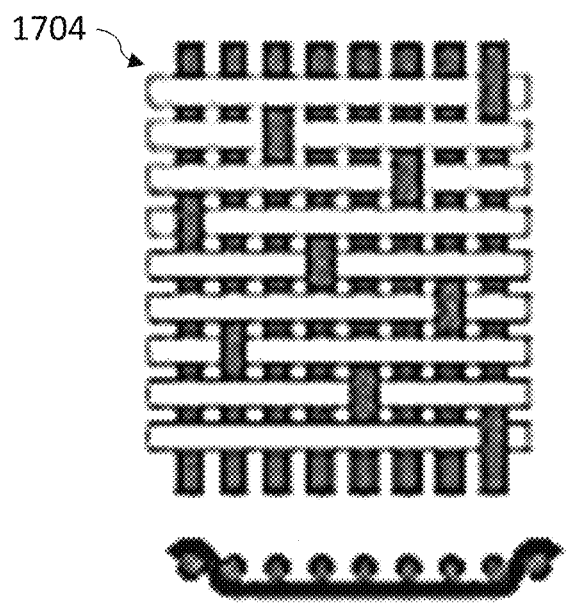
Figure 17D:
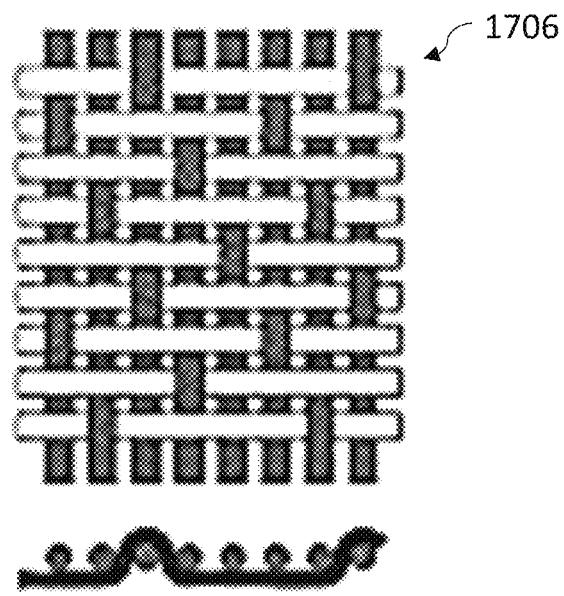
Figure 17E:
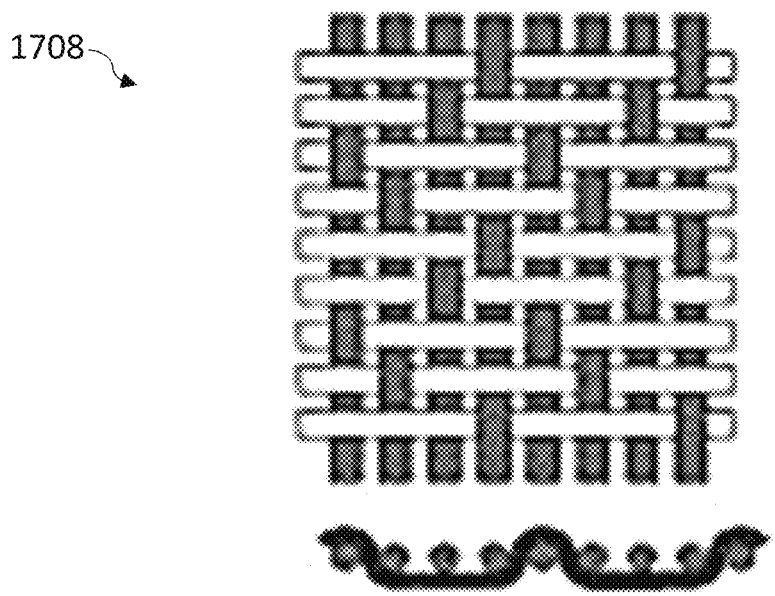

FIG. 15 depicts another exemplary embodiment of a medical textile 1500 comprising a marking indicator using colored yarn woven into the medical textile 1500. The colored yarn marking indicator may incorporate a longitudinal marking 1510 and circumferential marking 1520 and/or other indicators that are woven, non-woven, braided or knitted into the fabric of the medical textile. In this embodiment, a colored thread can be introduced into a machine, with the thread or threads knitted or woven into the medical textile. Desirably, the pattern and manufacturing techniques for this type of marking will desirably minimize skewing and/or other distortion of the markings during the 2-dimensional to 3-dimensional "opening" process. In this embodiment, a longitudinal marking 1510 and a series of circumferential bands 1520 are shown, with the longitudinal marking 1510 comprising a colored thread that is woven into the textile while the circumferential markings 1520 are ink-markings added later in the manufacturing process.

In various additional embodiments, supplemental marking techniques can be utilized to provide additional marking as required. For example, one exemplary embodiment of a medical textile fabric having markings and/or other indicators could include marking that are "printed" on the fabric with an externally visible ink formulation (not shown). In this embodiment, an inkjet or other type of printer can be used to apply an ink formulation to the external surface of the medical textile fabric, which can be applied in the 2-dimensional state, in the 3-dimensional state, and/or at various stages in both states, if desired. In various embodiments, a biocompatible ink or colorant formulation may be utilized, such as a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism In one exemplary embodiment, the ink formulations utilized herein may be, for example, carbon black, or green, cobalt blue or any colored line that is an FDA safe mixture. Commercially available inks may also be used. For example, TPR Ink manufactured by Marabuwerke GmbH & Co. (Tamm, Germany), is available from Autoroll Print Technologies, LLC (Middleton, Mass.; part number 3803 57 980). As a thinner for the TPR Ink, TPV Thinner, also manufactured by Marabuwerke GmbH & Co., is also available from Autoroll Print Technologies, LLC (part number 3501 97 046). Also, TPU ink, manufactured by Marabuwerke GmbH & Co., may be used. If desired, a suitable colorant could be compounded with virgin PET resin to produce colored fibers for conversion into threads and/or fabrics, including D&C Green #6, CAS #128-80-3 or D&C Blue #6, CAS #482-89-3.

In various embodiments, a medical textile may include various combinations of one or more of the marking techniques disclosed herein. For example, an ink-based textile marking technique may be used in combination with the disclosed minimal marking techniques using cold UV laser and/or ultrasound to provide a hybrid marking strategy, such as where medical grade inks and/or other colorants can be utilized to provide some of them markings and/or other indicators on the textile device. In some embodiments, the colorants and/or inks can be applied to one or more external surfaces of the textile and/or textile fibers in the 2-dimensional and/or 3-dimensional state, while in other embodiments the colorants and/or inks can be formulated and/or processed into the various fibers. It should be understood that virtually any combination of the disclosed marking techniques can be used herein, with varying results.

In various embodiments, a textile implantable device may include one or more markings and/or alignment guides that are integrally formed, printed and/or otherwise marked on an inner and/or outer surface of the medical textile, which could include a pair of longitudinally extending lines extending generally parallel to a central longitudinal axis of the medical textile (although in other embodiments the alignment guides could include one or three or more lines, or may include a different types of marking). Additional markings could be added in the 2-dimensional state, as desired, or could be added after the 3-dimensional state, if desired.

According to another aspect of the present invention, there is provided a medical textile including at least one marker or other indicia that can be integrated into and/or printed onto the medical textile. If desired, the marker could provide an indication of the part of the medical textile to which the marker is attached, such as denoting an "L", "R", "A" or "P" denoting, respectively, left, right, anterior and posterior. In addition to various alignment and/or processing markings, the various markings and/or other indicia described herein could include sizing, orientation, alignment and/or trim lines on various surfaces of the medical textile for use by the surgeon implanting the medical textile into a patient. In other embodiments, markings may be useful for aligning and/or placing stents or other structures within and/or outside of the medical textile, which may include attachment to the medical textile prior to and/or during the surgical procedure, if desired. The various markings could include indicia on a cuff to indicate to a surgeon the diameter size of the vein or vessel for each line. Numerical or other indicia could be provided to indicate that the surgeon should trim a certain amount and/or shape of medical textile material or similar instructions.

Marking Indicators Types and Characteristics

FIGS. 19A-19H depicts various embodiments of the types of marking indicators positioned on medical textiles. The marking indicator comprises characters or graphics. The characters comprise a symbol 1900, alphabet letters 1904, numbers 1902, alphanumeric characters 1906, and/or any combination thereof. The graphics comprises a logo (not shown), shapes (not shown), a photo (not shown), an image, 1D barcodes (not shown) geometric patterns 1912, 2D barcodes 1908, 1910, 3D barcodes 1914 and/or any combination thereof. The 2D barcodes may include linear barcodes, matrix barcode, and/or any combination thereof.

In another embodiment, the marking indicators comprises different characteristics. The characteristics include a size, a line thickness, a line spacing and a total thickness. The marking indicators comprises a size, the size may comprise a percentage of the area of the medical textile, which the percentage represents a maximum size before the mechanical performance is affected as compared to an unmarked medical textile. The size of the marking may include a range of 0.001% to 100% of the surface area of the medical textile, the size of the marking may include a range of 0.001% to 75% of the surface area of the medical textile, the size of the marking may include a range of 0.001% to 50% of the surface area of the medical textile, the size of the marking may include range of 0.001% to 25% of the surface area of the medical textile, the size of the marking may include range of 0.05% to 25% of the surface area of the medical textile, the size of the marking may include range of 0.5% to 10% of the surface area of the medical textile. The size of the marking may comprise 0.001% or greater of the surface area of the medical textile. In preferred embodiments, the size of the marking includes a range between 0.5% to 8.0% of the area of the medical textile. The size of the marking may include a range of 0.5% to 1% of the surface area of the medical textile, the size of the marking may include a range of 1% to 2% of the surface area of the medical textile, the size of the marking may include a range of 2% to 6% of the surface area of the medical textile, the size of the marking range may include a range of 6% to 8% of the surface area of the medical textile. Alternatively, the size of the marking range may include a range of 2% to 8% of the surface area of the medical textile, and the size of the marking may include a range of 4% to 8% of the surface area of the medical textile.

The marking indicators comprising a line thickness. Each character comprises a line beam, each line beam includes a line thickness is at least 0.005 mm. The line thickness may comprise a range of 0.005 mm to 50 mm, the line thickness may comprise a range of 0.005 mm to 40 mm, the line thickness may comprise a range of 0.005 mm to 20 mmm, the line thickness may comprise a range of 0.005 mm to 10 mm. The line thickness may be greater than 0.005 mm. In preferred embodiments, the line thickness may be greater than 0.005 mm. In preferred embodiments, the line thickness may comprise a range of 0.005 mm to 0.5 mm. The line thickness may comprise a range of 0.005 mm to 0.25 mm, the line thickness range may further comprise a range of 0.005 mm to 0.1 mm, the line thickness range may further comprise a range of 0.005 mm to 0.05 mm. Alternatively, each character comprises a plurality of line beams, the plurality of line beams are immediately adjacent, and/or the at least a portion of the plurality of line beams mate or contact or touch each other and/or the entirety of the plurality of line beams mate or contact or touch each other. Accordingly, each character comprises a plurality of line beams, the plurality of line beams are spaced apart, the spacing or spaced apart includes a range of 0.005 to 1 mm, the spacing or spaced apart includes a range of 0.0.005 mm to 1 mm, the spacing or spaced apart includes a range of 0.05 mm to 1 mm, the spacing or spaced apart includes a range of 0.1 mm to 1 mm, the spacing or spaced apart includes a range of 0.25 mm to 1 mm, the spacing or spaced apart includes a range of 0.5 mm to 1 mm. In addition, the spacing or spaced apart includes a range of 0.005 to 1 mm, which can be any spacing in 0.005 mm increments up to 1 mm.

In another embodiment, each character comprises a plurality of line beams, the plurality of line beams are spaced apart, the plurality of line beams creating a total width. The total width includes a range of 0.005 to 2 mm, the total width includes a range of 0.005 mm to 2 mm, the total width includes a range of 0.05 mm to 2 mm, the total width includes a range of 0.1 mm to 2 mm, the total width includes a range of 0.25 mm to 2 mm, the total width includes a range of 0.5 mm to 2 mm, and/or the total width includes 1 mm to 2 mm. In addition, the total width includes a range of 0.005 to 1 mm, which can be any spacing in 0.005 mm increments up to 2 mm.

In another embodiment, the one or more marking indicators may be disposed onto a medical textile and the one or more marking indicators can be aligned to a preferred direction of a textile structure to preserve mechanical performance of the medical textile. The one or more marking indicators may be aligned parallel to a preferred direction of the medical textile, the preferred direction comprises a longitudinal or vertical direction of a yarn; and/or a horizontal or latitudinal direction. The preferred direction may comprise a warp or weft, a course and/or a wale. Alternatively, the one or more marking indicators may be aligned perpendicular to a preferred direction of the medical textile, the preferred direction comprises a longitudinal or vertical direction of a yarn; and/or a horizontal or latitudinal direction. The preferred direction may comprise a warp or weft, a course and/or wale.

In another embodiment, the one or more marking indicators may be disposed onto a medical textile obliquely to a textile structure of the medical textile to preserve mechanical performance of the medical textile. The textile structure may comprise woven, non-woven, knit, and/or braided. The medical textile may comprise the same or different material properties throughout the length of the medical textile. Obliquely comprises at least 5 degrees from the medical textile axis. Obliquely may also comprise a range of 30 degrees to 60 degrees from the medical textile axis.

Specific Embodiments

Figures 20A, 20B:
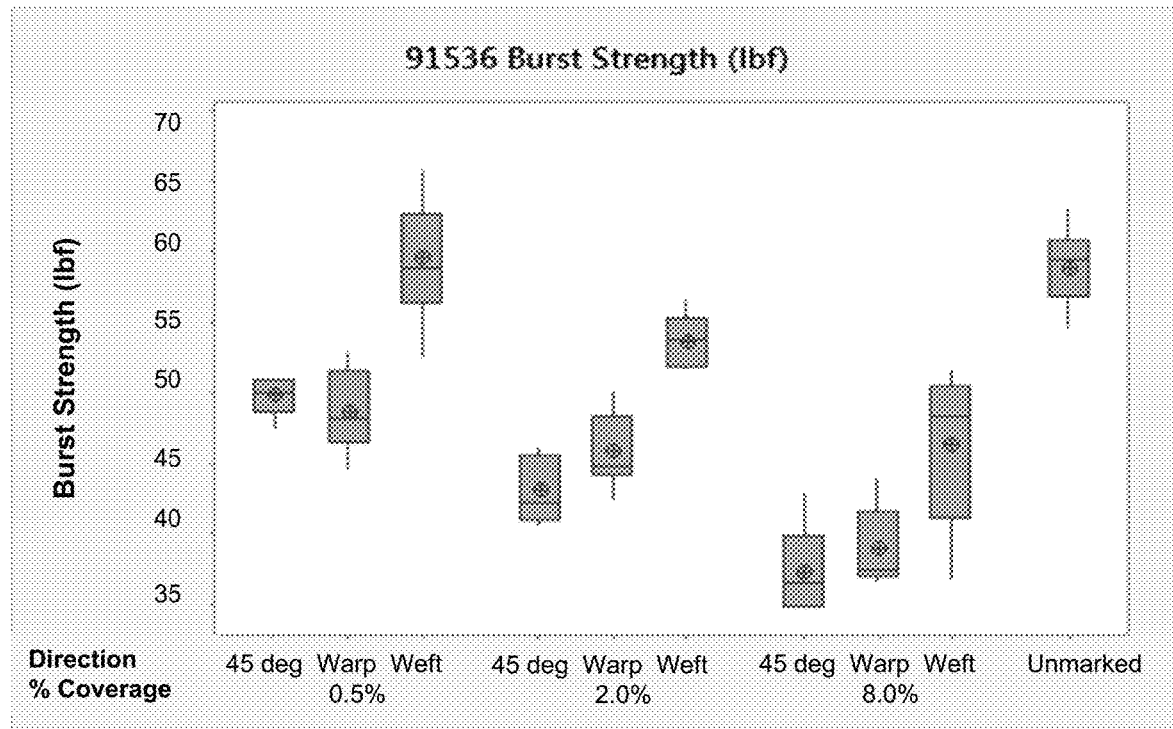
FIGS. 20A-20B depicts a graphical and data representation of burst strength testing for a woven medical textile with UV marking indicator(s)

FIGS. 20A-20B depict a graphical representation and data of a woven medical textile burst strength results using a UV marking indicator technique. The graphical representation comprises a boxplot of burst strength (lbf) comparing UV marked woven textiles with an unmarked woven textile. The woven medical textile comprises PET, a plain weave, with 250 ends per inch (EPI), 150 picks per inch/Inch (PPI), the PPI is the number of weft threads per inch of a woven fabric. A pick is a single weft thread. The yarn was 40 Denier and 6.5 turns per inch (TPI). The UV laser settings comprises 3C as shown in the UV setting grid within FIGS. 5A-5B. The boxplot summarizes marking indicators that had 0.5%, 2% and 8% size, that is expressed as a percentage of marking indicator coverage relative to the area of the textile. Several UV marking indicators were positioned and/or disposed to follow or align with a direction, the direction includes a direction parallel to the weft, direction parallel to the warp and/or 45 degrees across the weft and warp. The boxplot results indicate that aligning the UV marking indicators to the weft allows the burst strength to be comparable to the unmarked woven textile for all 0.5%, 2% and the 8.0% coverage. More specifically, the boxplot results indicate that aligning the UV marking indicator parallel to the weft allows the burst strength to be equal or substantially equal to the 0.5% marking indicator size (substantially is defined to be at least a 5% to 10% difference, higher or lower) compared to unmarked woven textile. In addition, the boxplot results for the 2% and 8% size coverage indicate that aligning the UV marking indicator parallel to the weft allows the burst strength to be lower than the unmarked woven textile. The lower amount is insignificant, which is approximately 20% to 33% lower than the unmarked woven textile. The lower amount is still readily acceptable to manufacturing specifications and/or customer specifications. Marking in the weft direction for this fabric is preferred since the density is lower in the weft direction. Furthermore, textiles with high density have fibers or filaments and/or yarns in closer proximity to the UV laser because the high-density filaments that are bundled together to form the yarn are raised relative to the lower density filaments. The raised yarns are raised away from the surface placing the yarns in closer proximity to the UV laser.

Figures 21A, 21B:
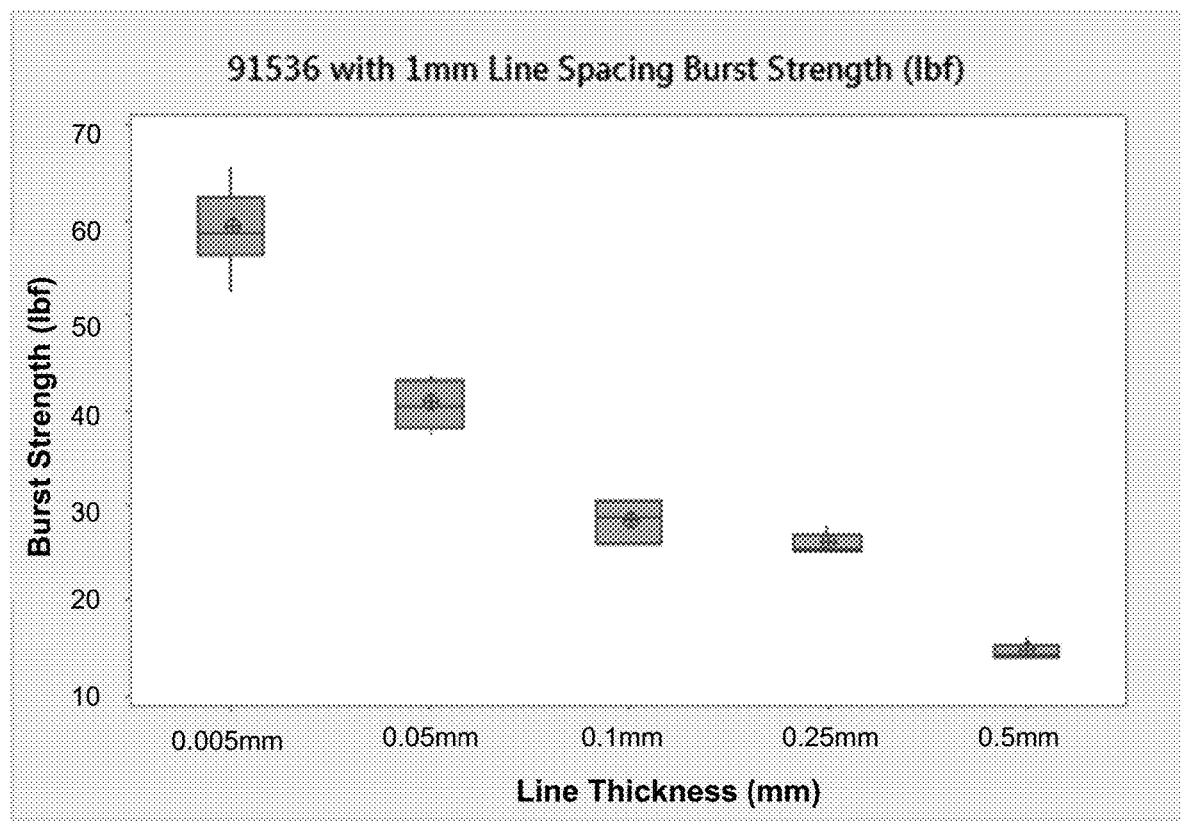
FIGS. 21A-21B depicts a graphical and data representation of burst strength testing for a woven medical textile with UV marking indicator(s)

FIGS. 21A-21B depict a graphical representation and data of a medical textile burst strength results using a UV marking indicator technique. The graphical representation comprises a boxplot of burst strength (lbf) comparing UV marked woven textiles with an unmarked woven textile. The woven medical textile comprises PET, a plain weave, with 250 ends per inch (EPI), 150 picks per inch/Inch (PPI), the PPI is the number of weft threads per inch of a woven fabric. The yarn was 40 Denier and 6.5 turns per inch (TPI). The UV laser settings comprises 3C as shown in the UV setting grid within FIGS. 5A-5B. Each of the marking indicator included a character, the character comprising a plurality of line beams, each of the plurality of line beams comprising a line thickness, each of the line beams were spaced apart and placed in parallel to the adjacent line beam. The plurality of line beams having a total line thickness or total thickness. The line spacing was equal to 1 mm spaced apart. The line thickness was set at 0.005 mm, 0.05 mm, 0.1 mm, 0.25 mm. The box plot summarizes marking indicators having at least one line beam with a line thickness of 0.005 mm has a burst strength equal to or substantially equal to an unmarked woven textile. All other line thicknesses of 0.05 mm, 0.1 mm, 0.25 mm, and 0.5 mm were 33% to 75% lower than the unmarked woven textile. However, the lower amount is still readily acceptable to manufacturing specifications and/or customer specifications.

Figures 22A, 22B:
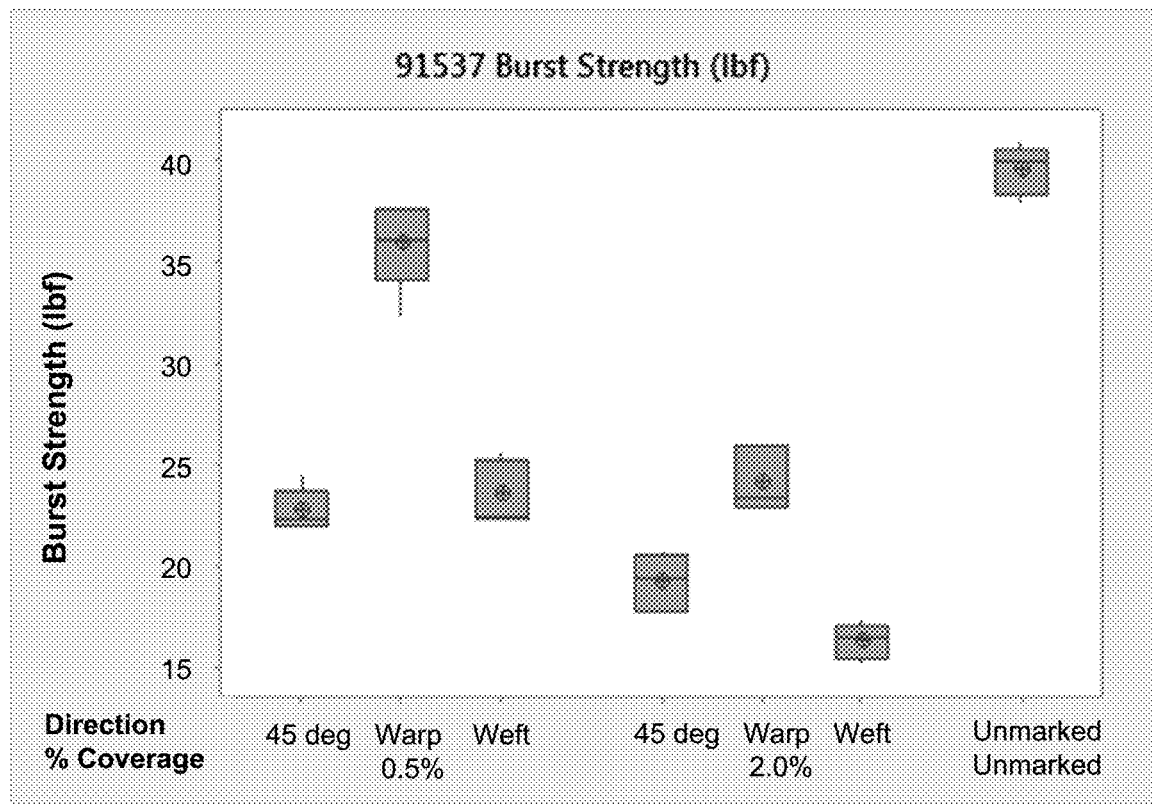
FIGS. 22A-22B depicts a graphical and data representation of burst strength testing for a woven medical textile with UV marking indicator(s)

FIGS. 22A-22B depict a graphical representation and data of a medical textile burst strength results using a UV marking indicator technique. The graphical representation comprises a boxplot of burst strength (lbf) comparing UV marked textiles with an unmarked woven textile. The woven medical textile comprises PET, a plain weave tape, with 245 ends per inch (EPI), 190 picks per inch (PPI), the PPI is the number of weft threads per inch of a woven fabric. The warp yarn was 20 Denier and 12 turns per inch (TPI), and the weft yarn was 20 denier and no twist. The UV laser settings comprises 3C as shown in the UV setting grid within FIGS. 5A-5B. The boxplot summarizes marking indicators that had 0.5% and 2% size, the size is expressed as a percentage of marking indicator coverage relative to the area of the textile. Several UV marking indicators were positioned and/or disposed to follow or align with a direction, the direction includes a weft, warp and/or 45 degrees across the weft and warp. The boxplot results indicate that aligning the UV marking indicator parallel to the warp allows the burst strength to be equal or substantially equal to the 0.5% marking indicator size (substantially is defined to be at least a 5% to 10% difference, higher or lower) compared to unmarked textile. In addition, the boxplot results for the 2% size coverage indicate that aligning the UV marking indicator parallel to the warp allows the burst strength to be lower than the unmarked woven textile. The lower amount is insignificant, which is approximately 38% to 59% lower than the unmarked woven textile. The lower amount is still readily acceptable to manufacturing specifications and/or customer specifications. Accordingly, aligning the UV marking indicator to the weft direction is also acceptable to manufacturing specifications and/or customer specifications. Marking in the warp direction for this textile is preferred since the warp yarns are twisted. The weft yarns are not twisted and marking in the weft direction allows for a lower burst strength, but comparable burst strength. Since the yarn is twisted, the mark is not cutting or damaging the yarn compared to an untwisted yarn. Instead, the mark is scoring or notching the yarn in the direction of a spiral, helix or coil.

Figures 23A, 23B:
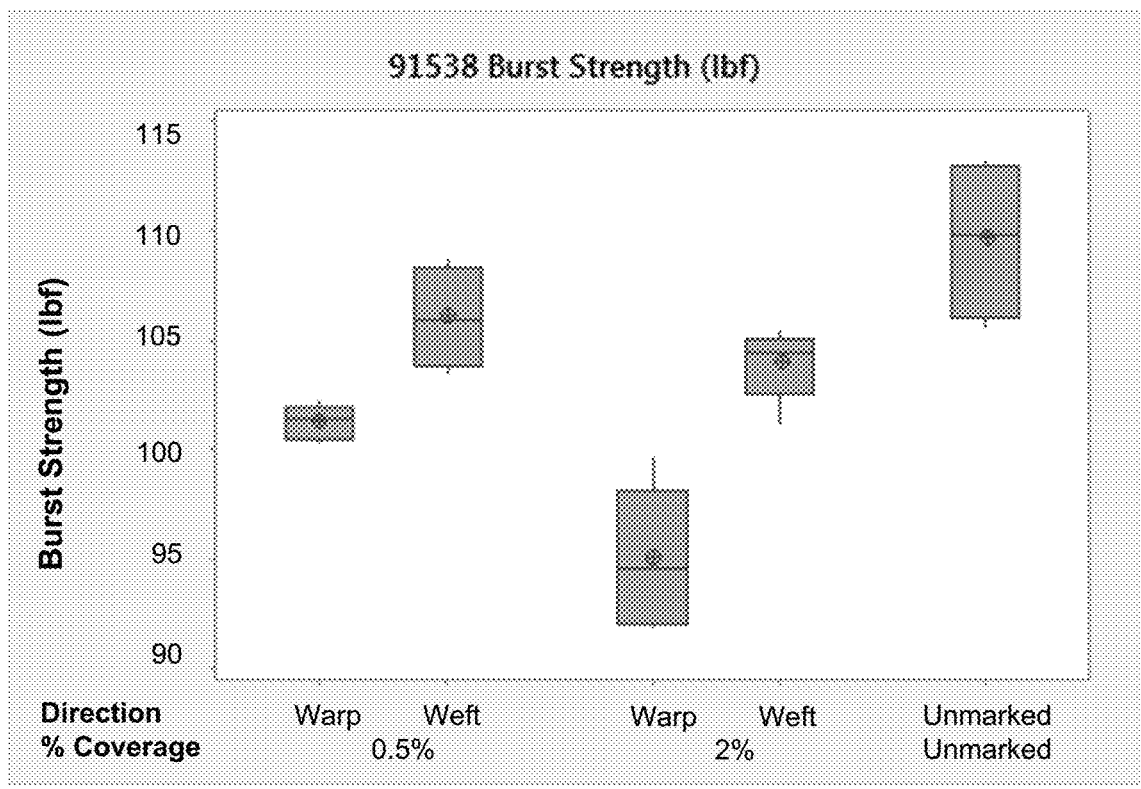
FIGS. 23A-23B depicts a graphical and data representation of burst strength testing for a woven medical textile with UV marking indicator(s)
Figure 24:
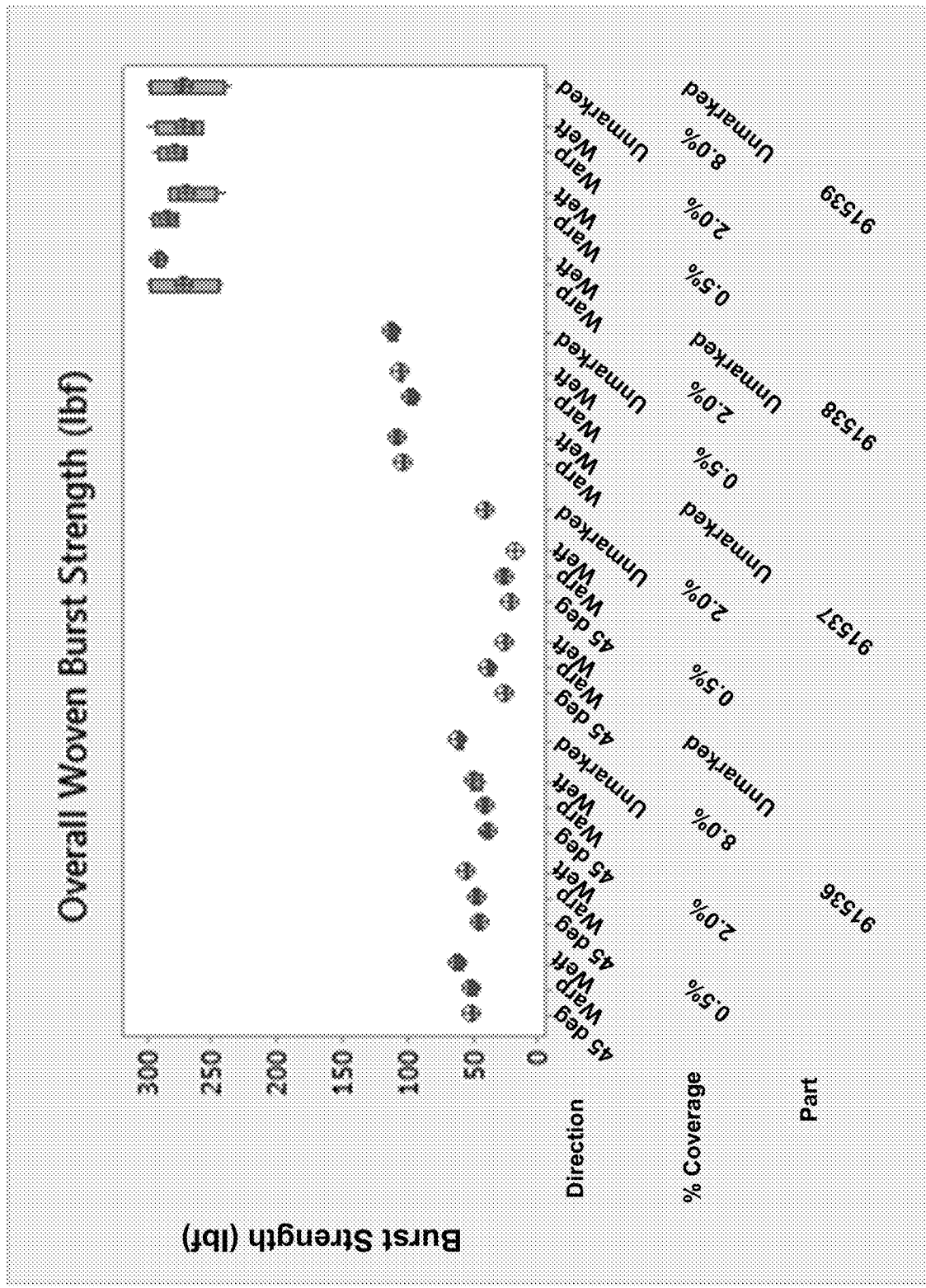
FIG. 24 depicts a graphical representation of burst strength testing for the woven medical textiles with UV marking indicator(s) of FIGS. 20A-20B, 21A-21B and 22A-22B.

FIGS. 23A-23B depict a graphical representation and data of a medical textile burst strength results using a UV marking indicator technique. The graphical representation comprises a boxplot of burst strength (lbf) comparing UV marked woven textiles with an unmarked woven textile. The woven medical textile comprises Velour weave, a plain weave, with 145 ends per inch (EPI), 140 picks per inch/Inch (PPI). The warp yarn was 2 ply, 40 Denier PET (80 Denier PET) and 7.5 turns per inch (TPI), a weft yarn no. 1 was 40 denier PET S-direction, and weft yarn no. 2 was 40 denier PET Z-direction. The UV laser settings comprises 3C as shown in the UV setting grid within FIGS. 5A-5B. The boxplot summarizes marking indicators that had 0.5% and 2% size, the size is expressed as a percentage of marking indicator coverage relative to the area of the textile. Several UV marking indicators were positioned and/or disposed to follow or align with a direction, the direction includes a weft and/or a warp. The boxplot results indicate that aligning the UV marking indicator to the weft or the warp is comparable burst strength to the unmarked woven textile. The boxplot results indicate that aligning the UV marking indicator parallel to the warp or weft allows the burst strength to be equal or substantially equal to the 0.5% and the 2% marking indicator size (substantially is defined to be at least a 3% to 13% difference higher or lower) compared to unmarked textile. Marking in either parallel to the warp or parallel to the weft or diagonal to the warp or weft is acceptable for this textile due to yarn balance—both PPI and EPI are balanced (i.e. 145:140) allowing equal strength in either the warp or weft direction and preserving burst strength relative to the unmarked textile. Furthermore, yarn balance increases the material flexibility. Yarn balance (PPI=EPI) allows for the materials to not lose strength after aligning the marking to weft, warp and/or oblique directions since the textile has a uniform weave pattern. Accordingly, aligning the UV marking indicator to the weft direction is also acceptable to manufacturing specifications and/or customer specifications. FIG. 24 depicts a graphical representation of all medical textile burst strength results for FIGS. 20A-20B, 21A-21B, 22A-22B, and 23A-23B together in one plot.

Figures 25A, 25B:
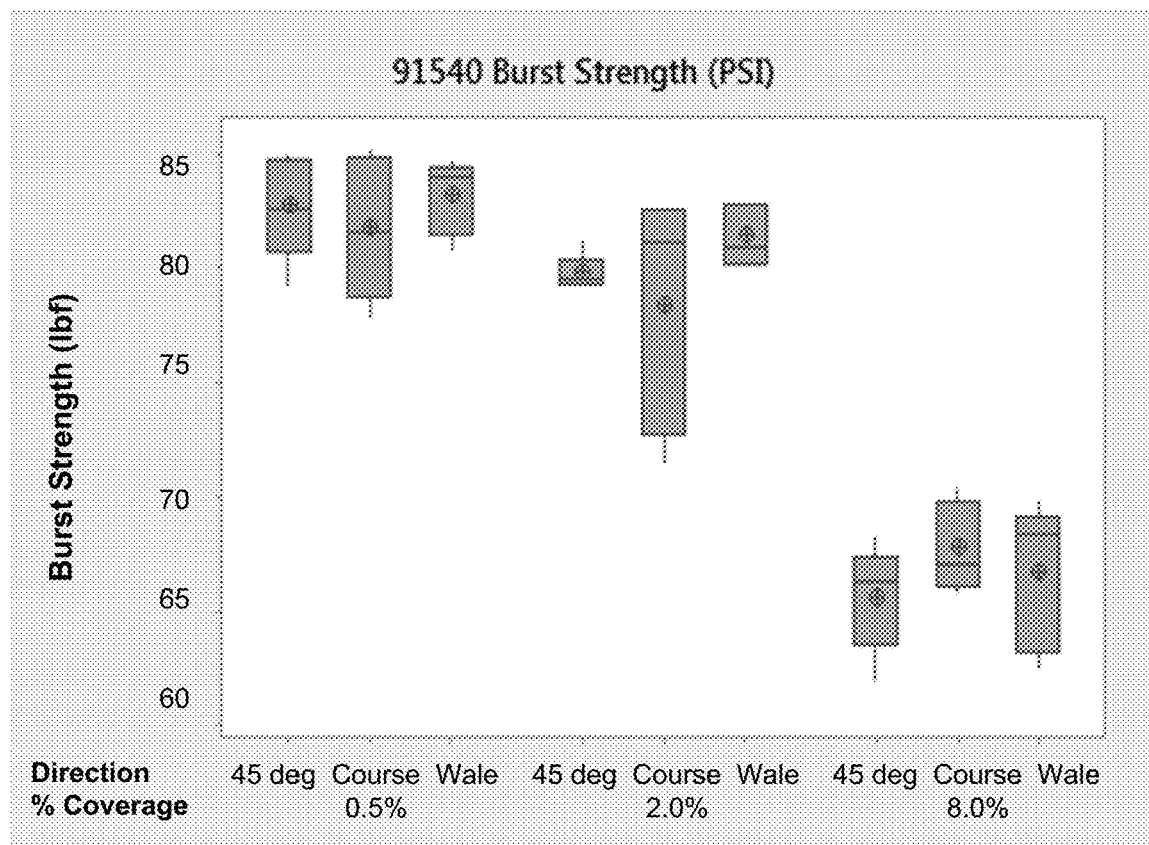
FIGS. 25A-25B depicts a graphical and data representation of burst strength testing for a knit medical textile with UV marking indicator(s)

FIGS. 25A-25B depict a graphical representation and data of a knit medical textile burst strength results using a UV marking indicator technique. The graphical representation comprises a boxplot of burst strength (lbf) comparing UV marked knit textiles with an unmarked knit textile. The knit medical textile comprises PET, a plain knit, with 86 courses per inch (CPI), 43 wales per inch/Inch (WPI). The yarn was 30 Denier PET and no twist or turns per inch (TPI). The boxplot summarizes marking indicators that had 0.5%, 2% and 8% size, the size is expressed as a percentage of marking indicator coverage relative to the area of the textile. Several UV marking indicators were positioned and/or disposed to follow or align with a direction, the direction includes a course or a wale and/or 45 degrees across the course and the wale. The boxplot results indicate that aligning the UV marking indicators to the either the course, wale and/or 45 degrees allows the burst strength to be comparable to the unmarked woven textile for all 0.5%, 2% and the 8.0% coverage. More specifically, the boxplot results indicate that aligning the UV marking indicator parallel to the either the course, wale and/or 45 degrees allows the burst strength to be equal or substantially equal to the 0.5% and 2% marking indicator size (substantially is defined to be at least a 5% to 10% difference, higher or lower) compared to unmarked knit textile. In addition, the boxplot results for the 8% size coverage indicate that aligning the UV marking indicator parallel to the course or wale allows the burst strength to be lower than the unmarked knit textile. The lower amount is insignificant, which is approximately 20% to 25% lower than the unmarked knit textile. The lower amount is still readily acceptable to manufacturing specifications and/or customer specifications.

Figures 26A, 26B:
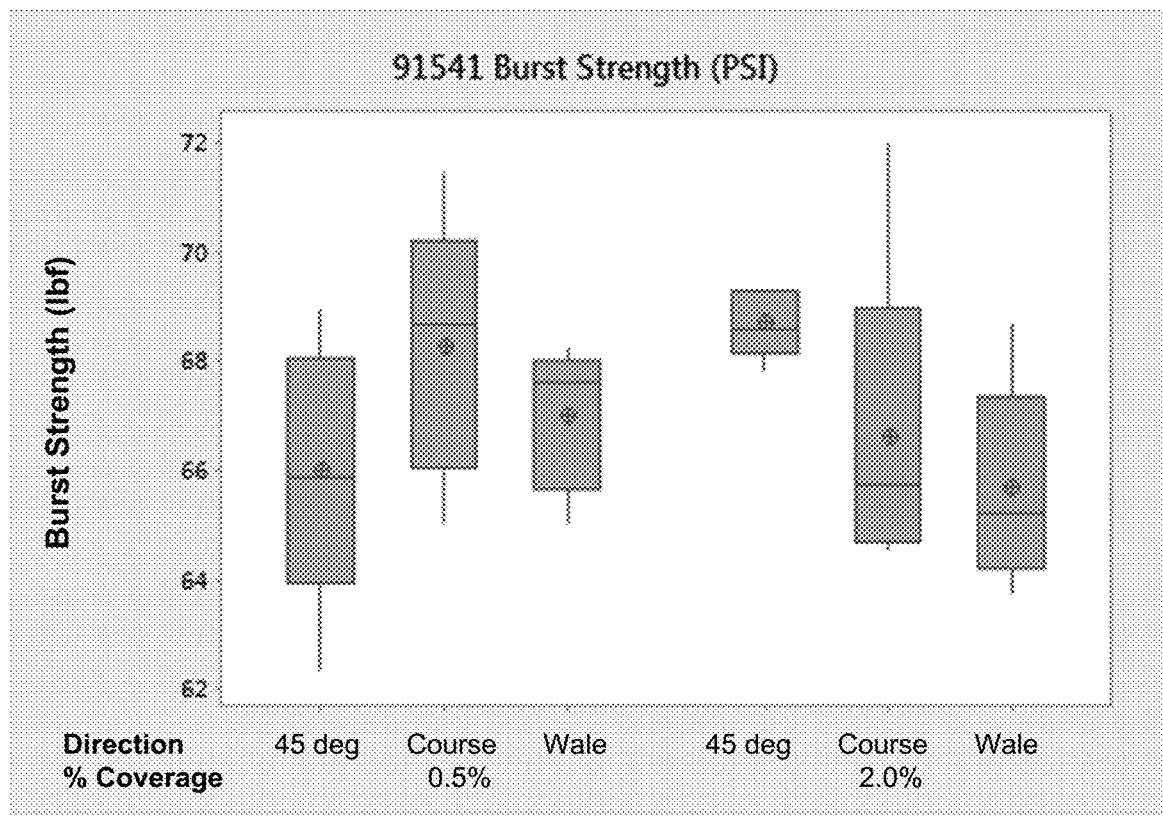
FIGS. 26A-26B depicts a graphical and data representation of burst strength testing for a knit medical textile with UV marking indicator(s)
Figure 27:
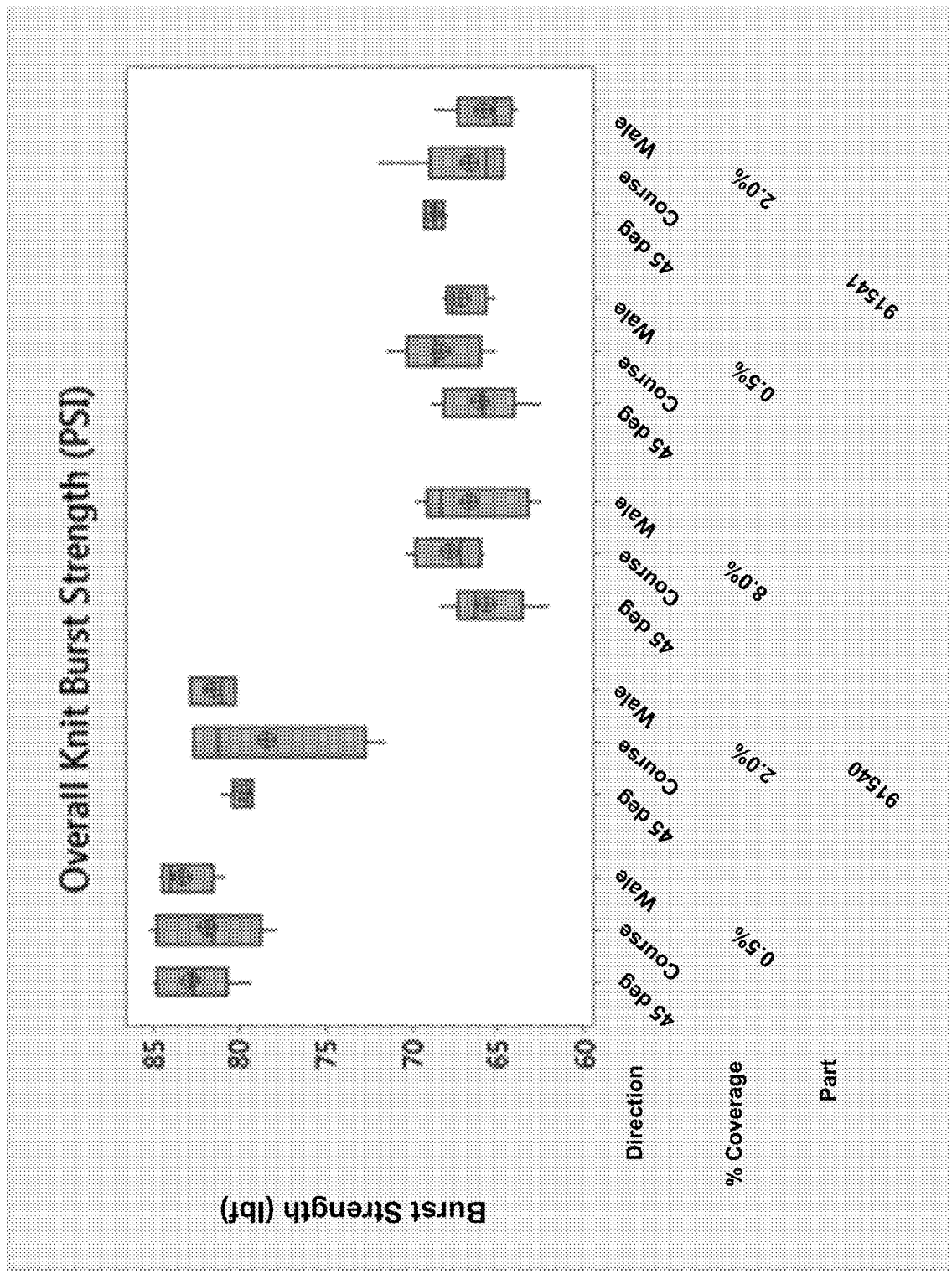
FIG. 27 depicts a graphical representation of burst strength testing for the knit medical textiles with UV marking indicator(s) of FIGS. 25A-25B and 26A-26B.

FIGS. 26A-26B depict a graphical representation and data of a knit medical textile burst strength results using a UV marking indicator technique. The graphical representation comprises a boxplot of burst strength (lbf) comparing UV marked knit textiles with an unmarked knit textile. The knit medical textile comprises PET, a plain knit, with 58 courses per inch (CPI), 45 wales per inch/Inch (WPI). The yarn no. 1 was 40 Denier textured PET in Z-direction, yarn no. 2 was 40 denier textured PET in S-direction, and yarn no. 3 was 40 denier textured PET with 5 twists per-inch (TPI). The UV laser settings comprises 3C as shown in the UV setting grid within FIGS. 5A-5B. The boxplot summarizes marking indicators that had 0.5%, 2% and 8% size, the size is expressed as a percentage of marking indicator coverage relative to the area of the textile. Several UV marking indicators were positioned and/or disposed to follow or align with a direction, the direction includes a course or a wale and/or 45 degrees across the course and the wale. The boxplot results indicate that aligning the UV marking indicators to the either the course, wale and/or 45 degrees allows the burst strength to be comparable to the unmarked knit textile for all 0.5%, 2% and the 8.0% coverage. More specifically, the boxplot results indicate that aligning the UV marking indicator parallel to the either the course, wale and/or 45 degrees allows the burst strength for the to be equal or substantially equal to the 0.5%, 2% and 8% marking indicator size (substantially is defined to be at least a 5% to 10% difference, higher or lower) compared to unmarked knit textile. FIG. 27 depicts a graphical representation of all knit medical textile burst strength results for FIGS. 25A-25B and 26A-26B together in one plot.

Figure 28A:
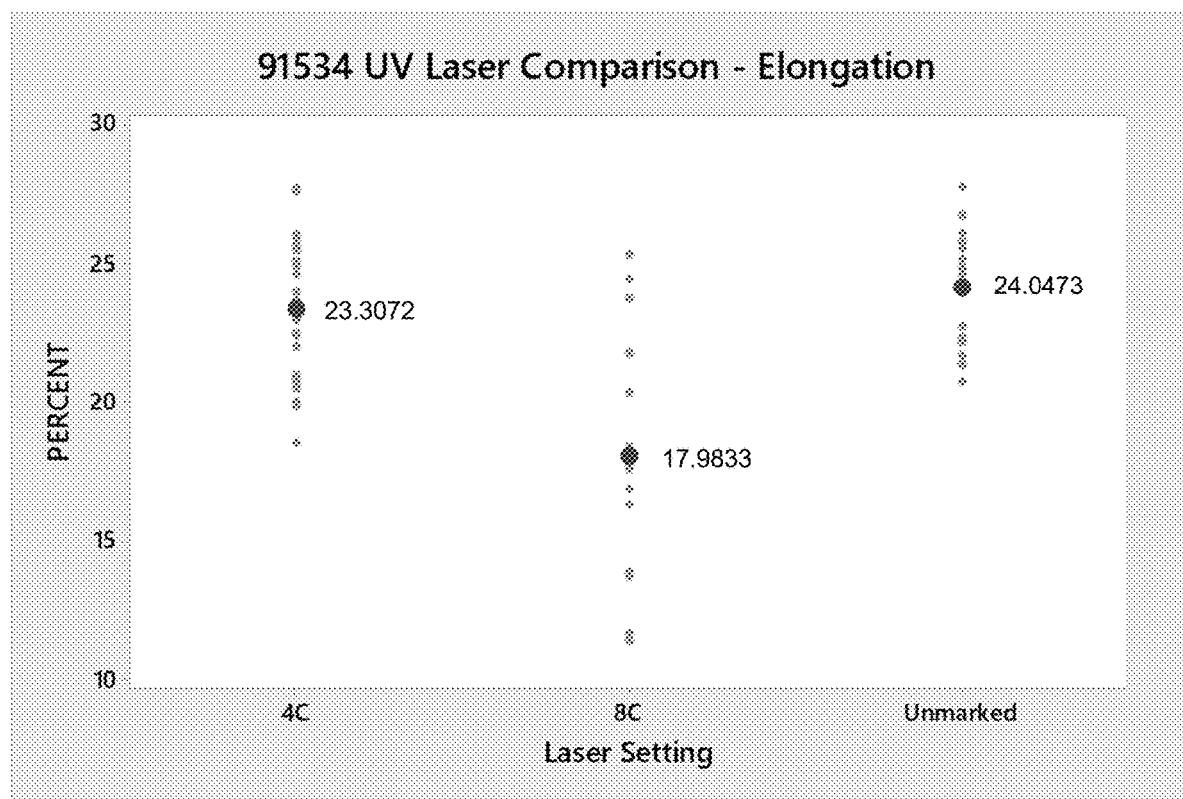
FIGS. 28A-28B depicts a graphical representation of mechanical performance testing for a yarn with UV marking indicator(s)
Figure 28B:
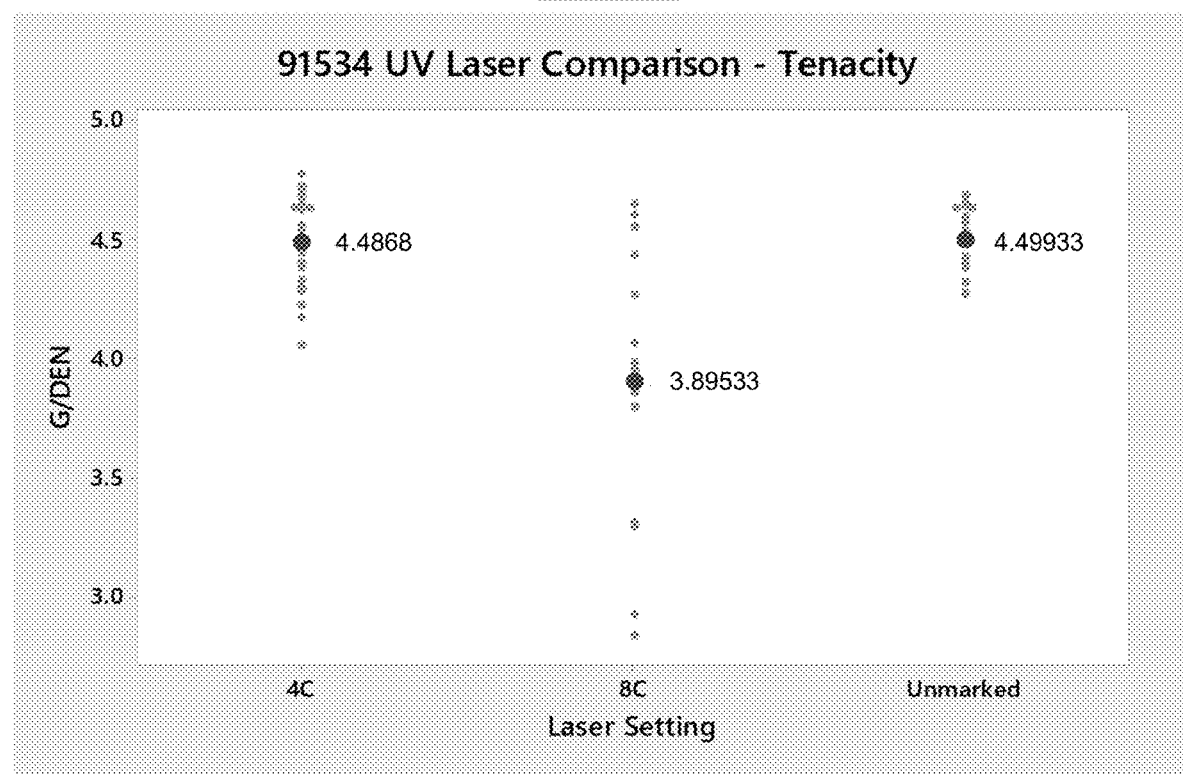

FIGS. 28A-28B depict a graphical representation of a yarn elongation and yarn tenacity results using a UV marking indicator technique. The graphical representation comprises an elongation % and tenacity g/denier graph comparing UV marked yarn with an unmarked yarn (e.g., the yarn was marked instead of the textile). The yarn comprises PET having a 40 denier, 27 filaments in a yarn strand, textured, 12 twists per inch (TPI). Tenacity was measured using ASTM D2256 as a reference standard. The UV laser settings comprises 4C and 8C as shown in the UV setting grid within FIGS. 5A-5B. The graph results indicate UV settings comprising 4C is equal or substantially equal (substantially is defined to be at least a 5% to 10% difference, higher or lower) compared to unmarked yarn. Accordingly, the graph results for the 8C settings indicate that elongation and tenacity is lower than the unmarked yarn. The lower amount is insignificant, which is approximately 11% to 25% lower than the unmarked yarn. The lower amount is still readily acceptable to manufacturing specifications and/or customer specifications.

Figure 29A:
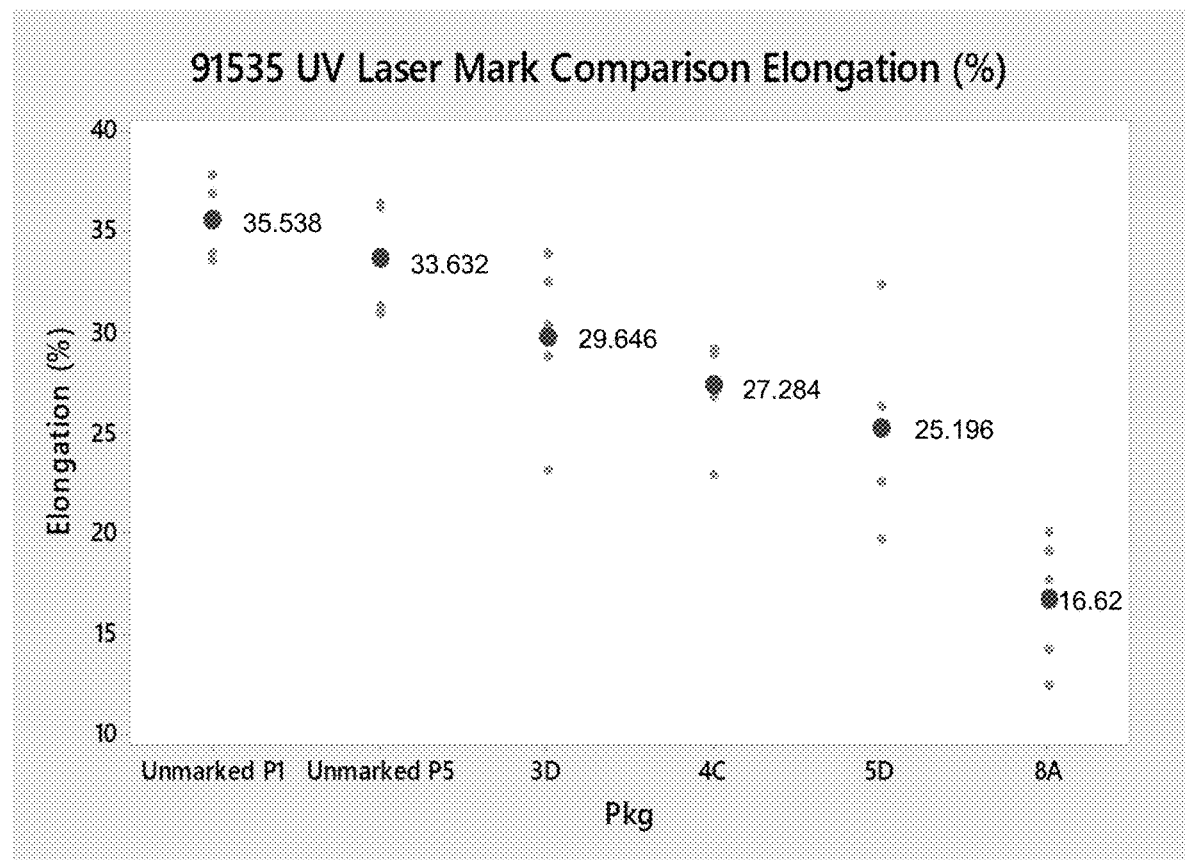
FIGS. 29A-29B depicts a graphical representation of mechanical performance testing for an alternate embodiment yarn with UV marking indicator(s)
Figure 29B:
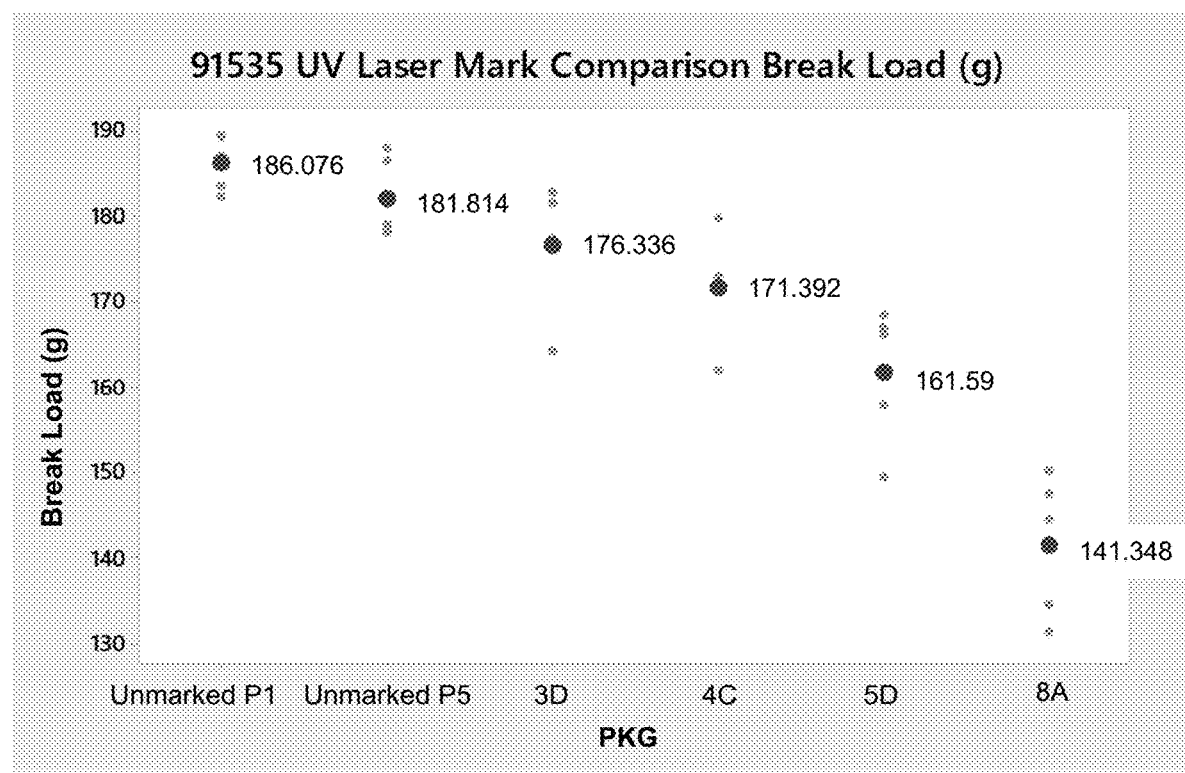
Figure 30A:
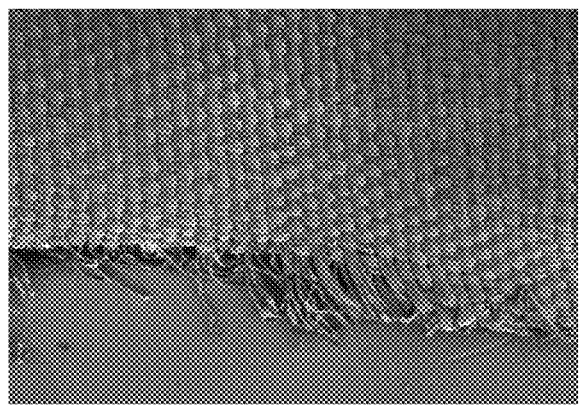
FIGS. 30A-30D depicts magnified views of a UHMWPE woven textile with UV marking indicator(s)
Figure 30B:
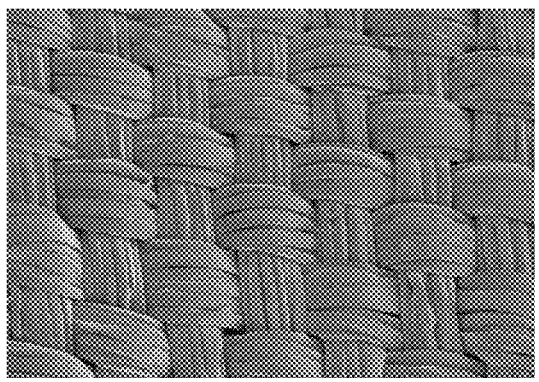
Figure 30C:
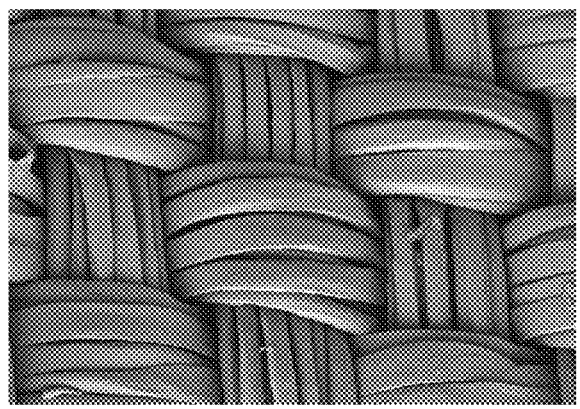
Figure 30D:
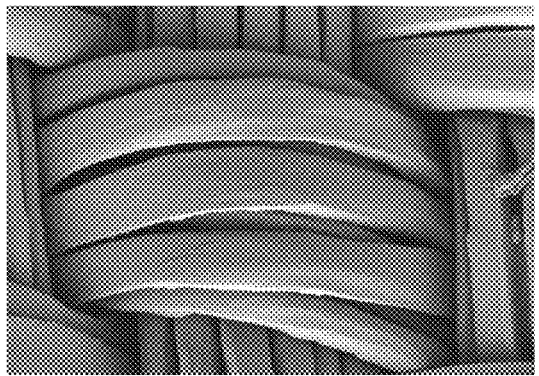

FIGS. 29A-29B depict a graphical representation of a yarn elongation and yarn tenacity results using a UV marking indicator technique. The graphical representation comprises an elongation % and break load (g) graph comparing UV marked yarn with an unmarked yarn (e.g., the yarn was marked instead of the textile). The yarn comprises PET having a 40 denier, 27 filaments in a yarn strand, textured, 6.5 twists per inch (TPI). The UV laser settings comprises 3D, 4C, 5D and 8A as shown in the UV setting grid within FIGS. 5A-5B. The graph results indicate that both elongation and break load was comparable to the unmarked yarn. More specifically, the graph results indicate UV settings comprising 3D is equal or substantially equal (substantially is defined to be at least a 5% to 16% difference, higher or lower) compared to unmarked yarn. Accordingly, the graph results for all other settings, 4C, 5D, and 8A indicate that elongation and break load is lower than the unmarked yarn. The lower amount is insignificant, which is approximately to 18% to 50% lower than the unmarked yarn. The lower amount is still readily acceptable to manufacturing specifications and/or customer specifications. Furthermore, the yarn with twists aids in retaining yarn strength in applications of UV laser marking.

Figure 31A:
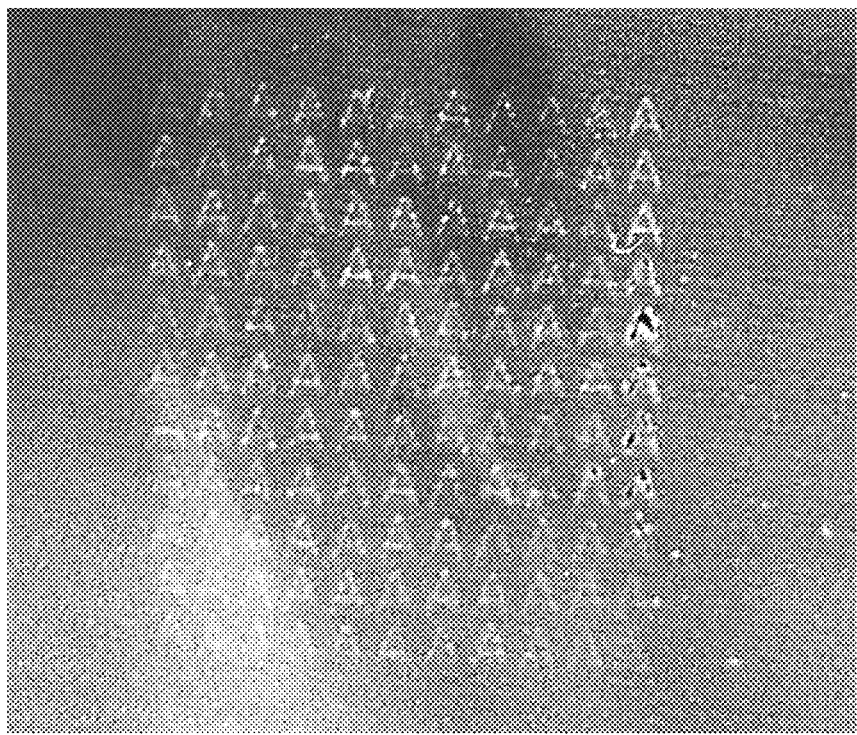
FIGS. 31A-31B depicts magnified views of the medical textile with UV marking indicator(s) of FIGS. 29A-29D under UV backlight and normal lighting, respectively.
Figure 31B:
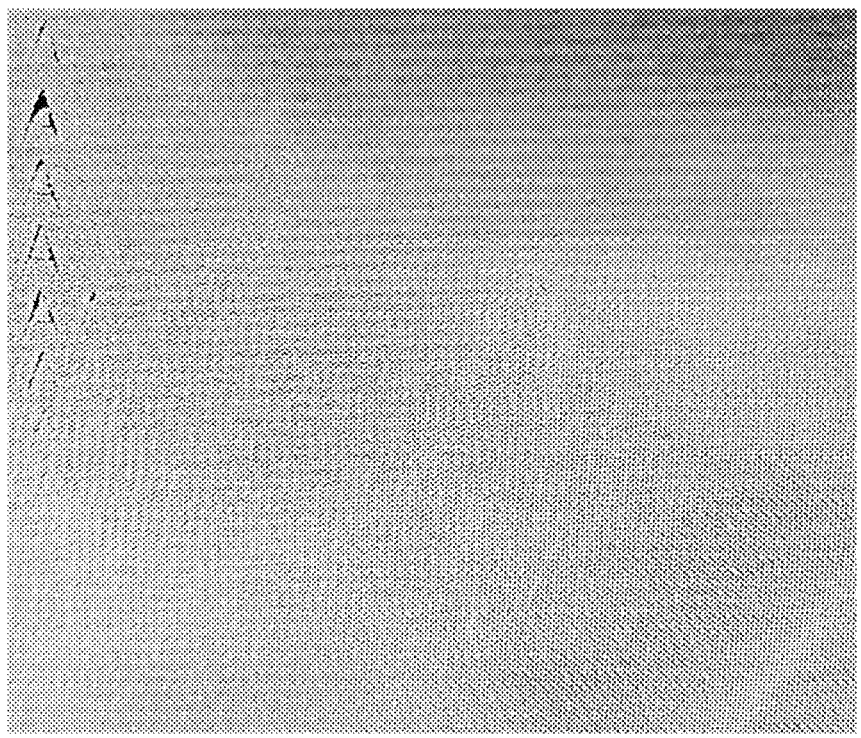

FIGS. 30A-30D and 31A-31B depict magnified views of a woven medical textile using UV marking indicator technique. The woven medical textile comprises an ultra-high molecular weight polyethylene (UHMWPE) in a plain weave pattern. The magnification is 30×, 150×, 300× and 600×, respectively. The magnified views how that the UHMWPE textile was marked with a plurality of characters using all settings from the UV setting grid within FIGS. 5A-5B. The magnified views resulted in a marked textile that is unable to detected with the naked eye as shown in FIG. 31B. In one embodiment, the marking indicator cannot be detected under naked eye, or in other words, the marking indicator may comprise a phosphorescent, transparent or translucent character or graphic. Phosphorescence is a process by which substances emit stored energy slowly, in the form of visible light within the ultraviolet (UV) light range. The marking indicator requires another form of visualization to highlight or detect the location of the "marked" area of the textile and/or to have the "marked" area fluorescent allowing the visualization technique used to be absorbed and re-emitted as visible light radiation, hence producing a visual mark able to be detected by the naked eye. For example, the visualization technique comprises UV backlight as shown in FIG. 31A or fluoroscopy, or x-ray. Alternatively, the marking indicator may comprise an opaque, or semi-opaque character or graphic.

Figures 32A, 32B:
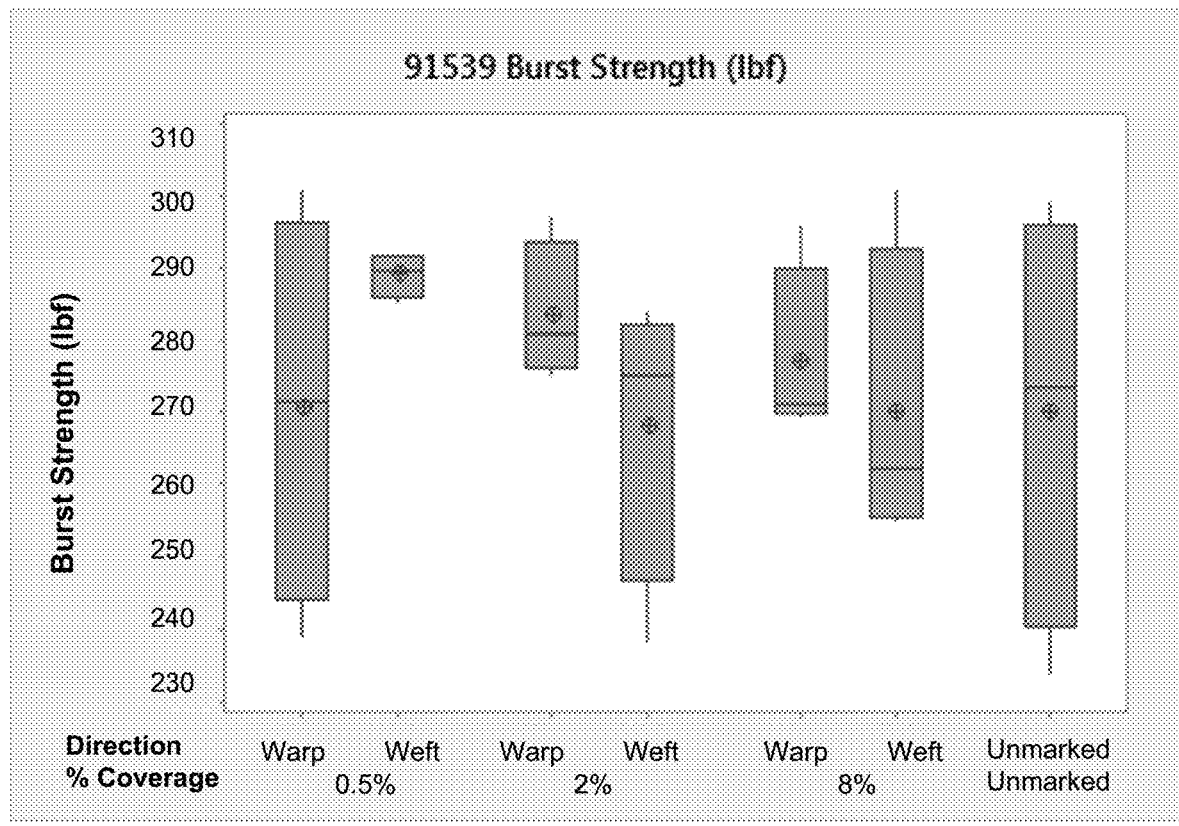
FIGS. 32A-32B depicts a graphical representation of burst strength testing for UHMWPE woven textile with UV marking indicator(s)

FIGS. 32A-32B depict a graphical representation and data of a UHMWPE medical textile burst strength results using a UV marking indicator technique. The graphical representation comprises a boxplot of burst strength (lbf) comparing UV marked UHMWPE textiles with an unmarked UHMWPE textile. The UHMWPE medical textile comprises, a plain weave tape, with 275 ends per inch (EPI), 200 picks per inch (PPI). The yarn was 20 Denier UHMWPE with 6.5 twists per-inch (TPI). The UV laser settings comprises 3C as shown in the UV setting grid within FIGS. 5A-5B. The boxplot summarizes marking indicators that had 0.5%, 2% and 8% size, the size is expressed as a percentage of marking indicator coverage relative to the area of the textile. Several UV marking indicators were positioned and/or disposed to follow or align with a direction, the direction includes a weft, warp and/or 45 degrees across the weft and the warp. The boxplot results indicate that aligning the UV marking indicators to the either the weft, warp and/or 45 degrees allows the burst strength to be comparable to the unmarked knit textile for all 0.5%, 2% and the 8.0% coverage. More specifically, the boxplot results indicate that aligning the UV marking indicator parallel to the either the weft, warp and/or 45 degrees allows the burst strength to be equal or substantially equal to the 0.5%, 2% and 8% marking indicator size (substantially is defined to be at least a 5% to 10% difference, higher or lower) compared to unmarked knit textile.

FIGS. 33A-33B depicts a graphical representation and data of a PET braided medical textile burst strength results using a UV marking indicator technique. The graphical representation comprises a boxplot of burst strength (lbf) comparing UV marked PET braided textiles with an unmarked PET braided textile. The PET braided medical textile comprises, a braid, 1×2 diamond full (this assumes a 45 degree angle of direction for the diamond pattern) with 27 picks per inch (PPI). The yarn was 100 Denier PET with 3 twists per-inch (TPI). The UV laser settings comprises 3C as shown in the UV setting grid within FIGS. 5A-5B. The boxplot summarizes marking indicators that had 0.5%, 2% and 8% size, the size is expressed as a percentage of marking indicator coverage relative to the area of the textile. Several UV marking indicators were positioned and/or disposed to follow or align with a preferred direction, the preferred direction includes a horizontal and vertical. The boxplot results indicate that aligning the UV marking indicators to the either the horizontal or vertical preferred direction allows the burst strength to be comparable to the unmarked knit textile for all 0.5%, 2% and the 8.0% coverage. More specifically, the boxplot results indicate that aligning the UV marking indicator parallel to the either the horizontal or vertical preferred direction allows the burst strength to be equal or substantially equal to the 0.5%, 2% and 8% marking indicator size (substantially is defined to be at least a 2% to 14% difference, higher or lower) compared to unmarked knit textile. Accordingly, the alignment of the UV marking indicator preferred direction is parallel to the braid pattern, which is 45 deg in this embodiment. The UV indicator marking aligns with the preferred direction of the oblique angle of the braid. The oblique angles include 15 to 75 degrees. Different braid patterns have different yarn oblique angles.

Accordingly, preserving the burst strength of medical textile comprising a UV marking indicator may be desirably accomplished by optimizing or modifying the textile structure and/or one or more textile material properties. Alternatively, two or more, three or more and/or four or more material properties may be modified or optimized to preserve mechanical strength of the marked medical textile. The preservation of the mechanical performance of the medical textile compared to an unmarked medical textile can be achieved. In one embodiment, the optimizing or modifying the one or more textile material properties comprising a lower density textile, yarn and/or filaments. The optimizing or modifying the one or more textile material properties comprising twists-per-inch, the twists-per-inch includes at least 3 twists-per-inch. The optimizing or modifying the one or more textile material properties comprising a larger filament diameter, the larger filament diameter includes at least 30 µm. The optimizing or modifying the one or more textile material properties comprising a high strength fabric or yarn. The optimizing or modifying the one or more textile material properties comprising balanced ends, the balanced ends are defined as a 1:1 ratio of PPI to EPI. The optimizing or modifying the one or more textile material properties may comprise a lower density textile, yarn or filaments; at least 5 twists-per-inch, a larger filament diameter comprising at least 30 µm, balanced ends, a high strength fabric, and/or any combination thereof.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. A marked medical textile comprises:
   a medical textile; the medical textile including a primary yarn and a secondary yarn; and
   a marking indicator, the marking indicator comprises a marking from a UV laser, the marking indicator being aligned parallel to a portion of the secondary yarn of the medical textile to preserve mechanical performance; wherein the preservation of mechanical performance of the marked medical textile comprises a burst strength substantially equal to an unmarked medical textile.

2. The marked medical textile of claim 1, wherein the medical textile comprises a woven medical textile or a knit medical textile.

3. The marked medical textile of claim 1, wherein the secondary yarn comprises a weft.

4. The marked medical textile of claim 1, wherein the medical textile comprises a plain weave.

5. The marked medical textile of claim 1, wherein the medical textile comprises polyethylene terephthalate (PET) or ultra-high weight molecular polyethylene (UHMWPE).

6. The marked medical textile of claim 1, wherein the marking indicator comprises characters or graphics.

7. The marked medical textile of claim 1, wherein the marking indicator comprises a size, the size is a range between 0.001% to 100% of area of medical textile.

8. The marked medical textile of claim 1, wherein the marking indicator being aligned parallel to a portion of the secondary yarn of the medical textile forms a marked surface, the marked surface is flush relative to an unmarked surface of the medical textile.

9. The marked medical textile of claim 1, wherein the marking indicator being aligned parallel to a portion of the secondary yarn of the medical textile forms a marked surface, the marked surface is raised relative to an unmarked surface of the medical textile.

10. The marked medical textile of claim 1, wherein the marking indicator being aligned parallel to a portion of the secondary yarn of the medical textile forms a marked surface, the marked surface is below the unmarked surface.

11. The marked medical textile of claim 1, wherein the secondary yarn is the course or wale.

12. A custom marked medical textile comprising:
    a medical textile; the medical textile including a primary yarn and a secondary yarn, the primary yarn being interlaced in a first direction with the secondary yarn in a second direction to create a textile structure, the textile structure including one or more material properties; and
    an ultra-violet (UV) marking indicator, the UV marking indicator being disposed onto a portion of the medical textile creating an marked portion of the medical textile and an unmarked portion of the medical textile, the marked portion of the medical textile including a burst strength that is equal to or greater than a burst strength of the unmarked portion of the medical textile.

13. The custom marked medical textile of claim 12, wherein the UV marking indicator is further aligned to at least one of the first direction or second direction of the textile structure of the medical textile.

14. The custom marked medical textile of claim 13, wherein the first direction or second direction is a weft.

15. The custom marked medical textile of claim 12, wherein the textile structure comprises a woven textile, a knit textile, or a braided textile.

16. The custom marked medical textile of claim 12, wherein the primary yarn or secondary yarn comprises twists, the twists include at least 1 twist-per-inch (TPI).

17. The custom marked medical textile of claim 12, wherein the one or more material properties comprises balanced ends, the balanced ends include ends-per-inch (EPI) equals the picks-per-inch (PPI).

18. The custom marked medical textile of claim 12, wherein the medical textile comprises a material, the material includes polyethylene terephthalate (PET) or ultra-high weight molecular polyethylene (UHMWPE).

19. The custom marked medical textile of claim 12, wherein the primary yarn or secondary yarn comprises one or more fiber diameters, the one or more fiber diameters being at least 30 µm.

* * * * *